US012749576B2

(12) United States Patent

Wang et al.

(10) Patent No.: US 12,749,576 B2
(45) Date of Patent: Sep. 29, 2026

(54) SYSTEM, METHOD AND COMPUTER READABLE MEDIUM FOR COMPRESSING CONTINUOUS GLUCOSE MONITOR DATA

(71) Applicant: University of Virginia Patent Foundation, Charlottesville, VA (US)

(72) Inventors: Ke Wang, Charlottesville, VA (US); Leon S. Farhi, Charlottesville, VA (US); Boris P. Kovatchev, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 782 days.

(21) Appl. No.: 17/776,056

(22) PCT Filed: Nov. 13, 2020

(86) PCT No.: PCT/US2020/060366

§ 371 (c)(1),
(2) Date: May 11, 2022

(87) PCT Pub. No.: WO2021/097178

PCT Pub. Date: May 20, 2021

(65) Prior Publication Data

US 2022/0392632 A1 Dec. 8, 2022

Related U.S. Application Data

(60) Provisional application No. 62/935,220, filed on Nov. 14, 2019.

(51) Int. Cl.
*G16H 40/67* (2018.01)
*G16H 10/60* (2018.01)
(Continued)

(52) U.S. Cl.
CPC ............ *G16H 40/67* (2018.01); *G16H 10/60* (2018.01); *G16H 20/17* (2018.01); *G16H 50/30* (2018.01)

(58) Field of Classification Search
None
See application file for complete search history.

(56) References Cited

U.S. PATENT DOCUMENTS 6,923,763 B1 8/2005 Kovatchev et al.
7,025,425 B2 4/2006 Kovatchev et al.
(Continued)

FOREIGN PATENT DOCUMENTS

WO 2001013786 A1 3/2001
WO 2001072208 A2 10/2001
(Continued)

OTHER PUBLICATIONS

Miller, Lachlan: Machine Learning week 1: Cost Function, Gradient Descent, and Univariate Linear Regression. (Year: 2018).*
(Continued)

*Primary Examiner* — Katherine Kolosowski-Gager
(74) *Attorney, Agent, or Firm* — Robert J. Decker

(57) ABSTRACT

A system or method for compressing continuous glucose monitor (CGM) data for a subject and/or a technician, clinician, or for use with an interventional device. The system or method configures the CGM data to allow the subject, technician, clinician, or interventional device to take a physical action in response to receiving a transmission to improve the safety and/or efficacy of therapy for the subject.

63 Claims, 26 Drawing Sheets

(51) Int. Cl.
*G16H 20/17* (2018.01)
*G16H 50/30* (2018.01)

(56) References Cited

U.S. PATENT DOCUMENTS

| | | | | |
|---|---|---|---|---|
| 7,761,144 | B2 | 7/2010 | Cox | |
| 7,815,569 | B2 | 10/2010 | Kovatchev et al. | |
| 7,874,985 | B2 | 1/2011 | Kovatchev et al. | |
| 8,135,548 | B2 | 3/2012 | Breton et al. | |
| 8,538,703 | B2 | 9/2013 | Kovatchev et al. | |
| 8,562,587 | B2 | 10/2013 | Kovatchev et al. | |
| 8,585,593 | B2 | 11/2013 | Kovatchev et al. | |
| 8,718,958 | B2 | 5/2014 | Breton et al. | |
| 9,317,657 | B2 | 4/2016 | Breton et al. | |
| 9,398,869 | B2 | 7/2016 | Kovatchev et al. | |
| 9,430,022 | B2 | 8/2016 | Kovatchev et al. | |
| 9,750,438 | B2 | 9/2017 | Kovatchev et al. | |
| 9,882,660 | B2 | 1/2018 | Breton et al. | |
| 10,169,544 | B2 | 1/2019 | Breton et al. | |
| 10,176,580 | B2 | 1/2019 | Pauly | |
| 10,194,850 | B2 | 2/2019 | Kovatchev et al. | |
| 10,291,268 | B1 | 5/2019 | Migliori et al. | |
| 10,328,204 | B2 | 6/2019 | Davis et al. | |
| 10,332,615 | B2 | 6/2019 | Kovatchev et al. | |
| 10,420,489 | B2 | 9/2019 | Kovatchev et al. | |
| 10,431,342 | B2 | 10/2019 | Kovatchev et al. | |
| 10,438,700 | B2 | 10/2019 | Ortiz et al. | |
| 10,445,323 | B2 | 10/2019 | Wang et al. | |
| 10,565,499 | B2 | 2/2020 | Bourdev et al. | |
| 10,583,842 | B1 | 3/2020 | Gunaratne et al. | |
| 10,672,504 | B2 | 6/2020 | Kennedy et al. | |
| 10,699,407 | B2 | 6/2020 | Isgum et al. | |
| 10,743,809 | B1 | 8/2020 | Kamousi et al. | |
| 10,748,448 | B2 | 8/2020 | Knott et al. | |
| 2002/0052557 | A1 | 5/2002 | Griffin et al. | |
| 2005/0214892 | A1 | 9/2005 | Kovatchev et al. | |
| 2008/0154513 | A1 | 6/2008 | Kovatchev et al. | |
| 2008/0269714 | A1 | 10/2008 | Mastrototaro et al. | |
| 2008/0314395 | A1 | 12/2008 | Kovatchev et al. | |
| 2009/0171589 | A1 | 7/2009 | Kovatchev | |
| 2010/0179768 | A1 | 7/2010 | Kovatchev et al. | |
| 2010/0198520 | A1 | 8/2010 | Breton et al. | |
| 2012/0004512 | A1 | 1/2012 | Kovatchev et al. | |
| 2012/0130698 | A1 | 5/2012 | Kovatchev et al. | |
| 2012/0245556 | A1 | 9/2012 | Kovatchev et al. | |
| 2013/0116649 | A1 | 5/2013 | Breton et al. | |
| 2014/0066735 | A1 | 3/2014 | Engelhardt et al. | |
| 2014/0073892 | A1* | 3/2014 | Randloev | G16H 50/50 600/365 |
| 2014/0304204 | A1* | 10/2014 | Cameron | G16H 50/70 706/21 |
| 2015/0018633 | A1 | 1/2015 | Kovatchev et al. | |
| 2015/0190098 | A1 | 7/2015 | Patek et al. | |
| 2015/0347698 | A1* | 12/2015 | Soni | G16H 50/30 706/11 |
| 2016/0012204 | A1 | 1/2016 | Booth et al. | |
| 2016/0331310 | A1 | 11/2016 | Kovatchev | |
| 2017/0220751 | A1* | 8/2017 | Davis | A61M 5/14244 |
| 2017/0273607 | A1* | 9/2017 | Facchinetti | A61B 5/725 |
| 2017/0293670 | A1 | 10/2017 | Wang et al. | |
| 2017/0311897 | A1* | 11/2017 | Faccioli | A61B 5/7203 |
| 2017/0337348 | A1 | 11/2017 | Kovatchev et al. | |
| 2018/0285424 | A1 | 10/2018 | Wang et al. | |
| 2018/0313815 | A1 | 11/2018 | Kovatchev et al. | |
| 2018/0314985 | A1* | 11/2018 | O'Shea | G06N 3/08 |
| 2018/0323882 | A1 | 11/2018 | Breton et al. | |
| 2018/0366223 | A1 | 12/2018 | Breton et al. | |
| 2019/0019571 | A1 | 1/2019 | Breton et al. | |
| 2019/0254595 | A1 | 8/2019 | Breton et al. | |
| 2019/0318801 | A1 | 10/2019 | Kovatchev et al. | |
| 2019/0374137 | A1 | 12/2019 | Kovatchev et al. | |
| 2020/0012938 | A1* | 1/2020 | Malhotra | G06N 3/088 |
| 2020/0066410 | A1 | 2/2020 | Kovatchev et al. | |

FOREIGN PATENT DOCUMENTS

| | | | |
|---|---|---|---|
| WO | 2002067776 | A1 | 9/2002 |
| WO | 2004015539 | A2 | 2/2004 |
| WO | 2005089431 | A2 | 9/2005 |
| WO | 2005106017 | A2 | 11/2005 |
| WO | 2007027691 | A1 | 3/2007 |
| WO | 2007081853 | A2 | 7/2007 |
| WO | 2008052199 | A2 | 5/2008 |
| WO | 2008067284 | A2 | 6/2008 |
| WO | 2008157781 | A1 | 12/2008 |
| WO | 2009009528 | A2 | 1/2009 |
| WO | 2010062898 | A1 | 6/2010 |
| WO | 2010099313 | A1 | 9/2010 |
| WO | 2010138848 | A1 | 12/2010 |
| WO | 2010151834 | A1 | 12/2010 |
| WO | 2011028731 | A1 | 3/2011 |
| WO | 2011028925 | A1 | 3/2011 |
| WO | 2011112974 | A1 | 9/2011 |
| WO | 2011119832 | A1 | 9/2011 |
| WO | 2012178113 | A1 | 12/2012 |
| WO | 2012178134 | A2 | 12/2012 |
| WO | 2013032965 | A1 | 3/2013 |
| WO | 2013177565 | A1 | 11/2013 |
| WO | 2014022864 | A1 | 2/2014 |
| WO | 2014130841 | A1 | 8/2014 |
| WO | 2015003124 | A2 | 1/2015 |
| WO | 2015103543 | A1 | 7/2015 |
| WO | 2016025874 | A1 | 2/2016 |
| WO | 2016200970 | A1 | 12/2016 |
| WO | 2016201120 | A1 | 12/2016 |
| WO | 2017070553 | A1 | 4/2018 |
| WO | 2020089656 | A1 | 5/2020 |
| WO | 2020113128 | A1 | 6/2020 |

OTHER PUBLICATIONS

Makino, Masaki et al., "Artificial intelligence predicts the progression of diabetic kidney disease using big data machine learning", Scientific reports, vol. 9, No. 1, 11862, 2019 (Published online Aug. 14, 2019), https://doi.org/10.1038/s41598-019-48263-5, 9 pages.

Asiri, Norah et al., "Deep learning based computer-aided diagnosis systems for diabetic retinopathy: A survey", Artificial intelligence in medicine, vol. 99, 101701, Aug. 2019, https://doi.org/10.1016/j.artmed.2019.07.009, pp. 1-35.

Katsuki, Takayuki et al., "Risk prediction of diabetic nephropathy via interpretable feature extraction from EHR using convolutional autoencoder", Building continents of knowledge in oceans of data: the future of co-created eHealth, IOS Press, 2018, https://doi.org/10.3233/978-1-61499-852-5-106, pp. 106-110.

Eltanboly, Ahmed et al., "A computer-aided diagnostic system for detecting diabetic retinopathy in optical coherence tomography images", Medical physics, vol. 44, No. 3, Mar. 2017, https://doi.org/10.1002/mp.12071, pp. 914-923.

Acciaroli, Giada et al., "Diabetes and prediabetes classification using glycemic variability indices from continuous glucose monitoring data", Journal of diabetes science and technology, vol. 12, No. 1, 2018, https://doi.org/10.1177/1932296817710478, pp. 105-113.

Longato, Enrico et al., "Simple linear support vector machine classifier can distinguish impaired glucose tolerance versus type 2 diabetes using a reduced set of CGM-based glycemic variability indices", Journal of diabetes science and technology, vol. 14, No. 2, 2020, pp. 297-302.

Oviedo, Silvia et al., "Risk-based postprandial hypoglycemia forecasting using supervised learning", International journal of medical informatics, vol. 126, 2019, https://doi.org/10.1016/j.ijmedinf.2019.03.008, pp. 1-8.

Kushner, Taisa et al., "Multi-hour blood glucose prediction in type 1 diabetes: A patient-specific approach using shallow neural network models", Diabetes Technology & Therapeutics, vol. 22, No. 12, 2020, https://doi.org/10.1089/dia.2020.0061, pp. 883-891.

Kovatchev, Boris P. et al., "Symmetrization of the blood glucose measurement scale and its applications", Diabetes care, vol. 20, No. 11, Nov. 1997, https://doi.org/10.2337/diacare.20.11.1655, pp. 1655-1658.

(56) References Cited

OTHER PUBLICATIONS

Kovatchev, Boris P. et al., “Risk analysis of blood glucose data: a quantitative approach to optimizing the control of insulin dependent diabetes”, Journal of Theoretical Medicine, vol. 3, No. 1, 2000, https://doi.org/10.1080/10273660008833060, pp. 1-10.

Kovatchev, Boris P., “Metrics for glycaemic control—from Habic to continuous glucose monitoring”, Nature Reviews Endocrinology, vol. 13, No. 7, Jul. 2017 (published online Mar. 17, 2017), https://doi.org/10.1038/nrendo.2017.3, pp. 425-436.

Design U.S. Appl. No. 29/467,039, entitled “Alarm Clock Display of Personal Blood Glucose Level”, filed Sep. 13, 2013, 4 pages.

WIPO, “International Search Report and Written Opinion of the International Searching Authority”, International Patent Application No. PCT/US2020/060366, mailed Feb. 4, 2021, 16 pages.

* cited by examiner

SYSTEM, METHOD AND COMPUTER READABLE MEDIUM FOR COMPRESSING CONTINUOUS GLUCOSE MONITOR DATA

CROSS REFERENCE TO RELATED APPLICATIONS

On Page 1, delete the paragraph entitled "CROSS REFERENCE TO RELATED APPLICATIONS" (lines 6-10) and substitute for it the following replacement paragraph:

The present application is a national stage filing of International Application No. PCT/US2020/060366, filed Nov. 13, 2020, which claims benefit of priority under 35 U.S.C § 119 (e) from U.S. Provisional Application Ser. No. 62/935,220, filed Nov. 14, 2019, entitled" "System and Method for Compact Representations and Clustering of Continuous Glucose Monitor Profiles"; the disclosures of which are hereby incorporated by reference herein in their entirety.

FIELD OF INVENTION

The present disclosure relates generally to compressing continuous glucose monitor (CGM) data for a subject and/or a technician, clinician, or interventional device. More particularly, the present disclosure relates to configuring the CGM data to allow the subject, technician, clinician, or interventional device to take a physical action in response to receiving said transmission to improve the safety and/or efficacy of therapy for said subject.

BACKGROUND

Introduction. Physicians monitor blood glucose (BG) levels to optimize insulin dosing schedules for patients with insulin-dependent diabetes. Traditional metrics, such as HbA1c and fasting BG, represent overall glucose control and can not predict variations in BG throughout the day. (See Kovatchev, B P, "Metrics for Glycaemic Control—from HbA1c to Continuous Glucose Monitoring", Nature Reviews Endocrinology. 2017; 13 (7): 425-436. http://doi.org/10/1038/nrendo.2017.3; of which is hereby incorporated by reference herein in its entirety.) Continuous glucose monitors (CGM) were recently developed to capture detailed, daily fluctuations in BG. These devices can measure the concentration of BG as frequently as every minute, opening the door for more sophisticated assessments of temporal changes in BG and their association with patient behavior (i.e. medication, diet, etc.). This allows for further optimization of treatment decision-making for patients with insulin-dependent diabetes.

However, raw CGM data is difficult to analyze via machine learning methods because it is highly-dimensional and inherently noisy. Conventional Lempel-Ziv based compression and decompression algorithms are not effective with CGM data, as they do not effectively filter noise. Therefore, there is a need for a more efficient approach to compress and decompress CGM data. An aspect of an embodiment of the present invention provides, but is not limited thereto, a novel method and system to optimize the reconstruction of CGM data, utilizing knowledge of diabetes (glycemic risk profile) with advances in machine learning (unsupervised neural networks).

Neural Networks. A neural network is a computational model designed to solve problems such as character identification and image recognition. A typical neural network consists of at least two layers—an input and output layer—of neurons, mathematical functions consisting of an activation function and a corresponding weight. Through a process called "training," a neural network can determine the proper connection weight of every neuron to recognize a desired pattern.

There are three important types of neural networks: Artificial Neural Networks (ANNs), Recurrent Neural Networks (RNNs), and Convolution Neural Networks (CNNs). While ANNs are capable of learning any nonlinear function and mapping any input to the output, ANNs cannot capture sequential information in the input data. RNNs try to solve this problem by introducing a looping constraint on intermediary, or "hidden," layers of ANNs. By keeping some internal state, RNNs can capture the sequential information in the input dataset. CNNs, on the other hand, are used to process spatial data such as images. CNNs differ from both ANNs and RNNs in that they have unique layers called "convolution layers," which transform the inputs before passing them to the next layer.

CNNs. CNNs' convolution and maxpooling layers make them ideal, in most cases, for use in autoencoders designed to reduce data dimension in an unsupervised manner. Autoencoders generally consist of three layers—encoder, code, and decoder (See FIG. 1). The encoder encodes the input data as a compressed representation in a reduced dimension. The code represents the compressed input which is fed to the decoder. The decoder decodes the encoded data back to the original dimension. The decoded data is a lossy reconstruction of the original data, reconstructed from the latent space representation.

SUMMARY OF ASPECTS OF EMBODIMENTS OF THE INVENTION

Physicians regularly monitor blood glucose (BG) levels to optimize insulin dosing schedules for patients with insulin-dependent diabetes. Traditional metrics (HbA1c, mean BG, etc.) measure average glycemic control over the past 2-3 months and represent overall risk, whereas continuous glucose monitor (CGM) data captures detailed, daily fluctuations in BG. A CGM measures the concentration of BG as frequently as every 5 minutes (288 times per day), opening the door for more sophisticated assessments of temporal changes in BG. However, raw CGM data is difficult to analyze via machine learning methods because it is highly-dimensional and inherently noisy.

Extracting useful features while suppressing the uncertainty introduced by device noise from CGM profiles is a required first step before feeding CGM data to any machine learning algorithm. In this regard, Acciaroli et al. (See Acciaroli G., et al., "Diabetes and Prediabetes Classification Using Glycemic Variability Indices from Continuous Glucose Monitoring Data", Journal of Diabetes Science and Technology. 2018; 12 (1): 105-113. https://doi.org/10.1177/1932296817710478; of which is hereby incorporated by reference herein in its entirety) extended the feature set to 25 glycemic variability (GV) indices and established a binary logistic regression model to classify subjects into classes of impaired glucose tolerance (IGT) and type 2 diabetes (T2D). Longato et al. (See Longato E, et al., "Simple Linear Support Vector Machine Classifier Can Distinguish Impaired Glucose Tolerance Versus Type 2 Diabetes Using a Reduced Set of CGM-Based Glycemic Variability Indices", Journal of Diabetes Science and Technology. 2020; 14 (2): 297-302. https://doi.org/10.1177/1932296819838856; of which is hereby incorporated by reference herein in its entirety) further extended the feature set to 37 GV indices and four individual parameters and trained a polynomial-kernel support vector machine (SVM) model to classify IGT and T2D. Oviedo et al. (See Oviedo S, et al., "Risk-Based Postprandial Hypoglycemia Forecasting Using Supervised Learning", International Journal of Medical Informatics. 2019; 126: 1-8. https://doi.org/10.1016/j.ijmedinf.2019.03.008; of which is hereby incorporated by reference herein in its entirety) defined a feature set that includes the raw CGM data, differential and cumulative features from recent 2-hour historical CGM, insulin, and carbohydrate intake, as well as the pre-programmed basal insulin delivery for the next 4 hours. Then the features were utilized to train a SVM classifier for predicting hypoglycemia. However, the CGM features extracted in these works are not able to capture and predict the trend of BG change. (See Kusher T, Breton M D, Sankaranarayanan S, "Multi-Hour Blood Glucose Prediction in T1D: A Patient-Specific Approach Using Shallow Neural Network Models", Diabetes Technology & Therapeutics. 2020 [preprint]. https://doi.org/10.1089/dia.2020/0061; of which is hereby incorporated by reference herein in its entirety.) In short, machine learning features derived from raw CGM data by Acciaroli, Longato, Oviedo, and other researchers are not able to accurately model the rate of BG change. To address this issue, the present inventor has developed a system and method for a diabetic-specific, unsupervised, feature learning approach to remove noise, create a compact representation of daily CGM profiles, and ultimately optimize treatment decision-making for patients with insulin-dependent diabetes.

First, in an aspect of an embodiment the present inventor trained an autoencoder with data from the International Diabetes Closed Loop (iDCL) Trial, a clinical trial testing two CGMs. The autoencoder applied a mean squared error cost function (weighted with hypoglycemia risk, specifically low blood glucose index (LBGI), to the power of 0.5, 0.75, and 1) on the iDCL-1 data to extract low-dimensional temporal features from daily CGM profiles. Pertaining to an embodiment the present inventor then performed a K-means clustering analysis on this low-dimensional dataset, yielding four separable clusters among the daily CGM profiles. Second, in an aspect of an embodiment the present inventor tested their trained autoencoder on daily CGM profiles from iCDL-3 data. To validate the efficacy of their autoencoder approach, the present inventor in an aspect of an embodiment compared their results with four well-established methods for generating compact representations: two data-driven approaches, principal component analysis (PCA) and independent component analysis (ICA), and two non-data-driven approaches, native subsampling (SS) and discrete cosine transformation (DCT). While the PCA and ICA achieve the best overall reconstruction performance, the risk-weighted autoencoder gives the most natural separation of the glucose profiles.

An aspect of an embodiment of the present invention provides, among other things, a system, method and computer readable medium for compact representations and clustering of daily continuous glucose monitor (CGM) profiles.

An aspect of an embodiment of the present invention provides, among other things, a system, method and computer readable medium for deriving compact representations of daily continuous glucose monitor (CGM) profiles.

An aspect of an embodiment of the present invention provides, among other things, a system, method and computer readable medium for clustering and stratification of continuous glucose monitor (CGM) daily profiles in the international diabetes closed-loop (iDCL) trial.

An aspect of an embodiment of the present invention provides, among other things, a system, method and computer readable medium for a feature-learning technique for temporal feature extraction trained on iDCL-1 and applied to iDCL-3 data classifies daily CGM profiles into four separable clusters which distinct CGM patterns between different times of the day, 3 am to noon vs. noon to 3 am. The classifier is sensitive to treatment and differentiates between control and experimental group.

An aspect of an embodiment of the present invention provides, among other things, a system, method and computer readable medium for feature-learning approach for analysis of CGM daily profiles in the iDCL trial that is applicable (but not limited thereto) to future treatment optimization and decision-making support.

It shall be noted that this disclosure shall include, but is not limited thereto, neural network autoencoder, principle component analysis (PCA) and independent component analysis (ICA). In an embodiment, the present inventor may emphasize the advantages of the autoencoder method over the other methods, but PCA and ICA are also innovative methods and are included as part of this disclosure, and implementations thereof.

An aspect of an embodiment of the present invention provides, among other things, a computer-implemented method for compressing continuous glucose monitor (CGM) data of a subject. The method may comprise: receiving CGM data profiles of said subject; extracting glycemic risk profiles from the CGM data profiles; compressing the CGM data profiles into low-dimensional representations using a trained neural network encoder via a cost function weighted by said extracted glycemic risk profiles; and transmitting said low-dimensional representations of CGM profiles to a secondary source, or reconstructing said low-dimensional representations of CGM profiles to full-dimensional CGM profiles via a trained neural network decoder and transmitting said reconstructed full-dimensional CGM profiles via said trained neural network decoder to a secondary source. In an embodiment, the transmitted low-dimensional representations of CGM profiles, which optionally are configured to be reconstructed to full-dimensional CGM profiles, are configured to allow: a) said subject, a technician, or a clinician to take a physical action in response to receiving said transmission to improve the safety and/or efficacy of therapy for said subject, or b) an interventional device to operationally take action in response to receiving said transmission to improve the safety and/or efficacy of therapy for said subject. In an embodiment, said transmitted reconstructed full-dimensional CGM profiles are configured to allow: a) said subject, a technician, or a clinician to take a physical action in response to receiving said transmission to improve the safety and/or efficacy of therapy for said subject, or b) an interventional device to operationally take action in response to receiving said transmission to improve the safety and/or efficacy of therapy for said subject.

An aspect of an embodiment of the present invention provides, among other things, a system configured for compressing continuous glucose monitor (CGM) data of a subject. The system may comprise: a computer processor; a memory configured to store instructions that are executable by the computer processor. The processor is configured to execute the instructions to: receive CGM data profiles of said subject; extract glycemic risk profiles from the CGM data profiles; compress the CGM data profiles into low-dimensional representations using a trained neural network encoder via a cost function weighted by said extracted corresponding glycemic risk profiles; and transmit said low-dimensional representations of CGM profiles to a secondary source, or reconstruct said low-dimensional representations of CGM profiles to full-dimensional CGM profiles via a trained neural network decoder and transmit said reconstructed full-dimensional CGM profiles via said trained neural network decoder to a secondary source. In an embodiment, the transmitted low-dimensional representations of CGM profiles, which optionally are configured to be reconstructed to full-dimensional CGM profiles, are configured to allow: a) said subject, a technician, or a clinician to take a physical action in response to receiving said transmission to improve the safety and/or efficacy of therapy for said subject, or b) an interventional device to operationally take action in response to receiving said transmission to improve the safety and/or efficacy of therapy for said subject. In an embodiment, the transmitted reconstructed full-dimensional CGM profiles are configured to allow: a) said subject, a technician, or a clinician to take a physical action in response to receiving said transmission to improve the safety and/or efficacy of therapy for said subject, or b) an interventional device to operationally take action in response to receiving said transmission to improve the safety and/or efficacy of therapy for said subject.

An aspect of an embodiment of the present invention provides, among other things, a computer program product, comprising a non-transitory computer-readable storage medium containing computer-executable instructions for compressing continuous glucose monitor (CGM) data of a subject. The instructions causing the computer to: receive CGM data profiles of said subject; extract glycemic risk profiles from the CGM data profiles; compress the CGM data profiles into low-dimensional representations using a trained neural network encoder via a cost function weighted by said glycemic risk profiles; and transmit said low-dimensional representations of CGM profiles to a secondary source or reconstruct said low-dimensional representations of CGM profiles to full-dimensional CGM profiles via a trained neural network decoder and transmit said reconstructed full-dimensional CGM profiles via said trained neural network decoder to a secondary source. In an embodiment, the transmitted low-dimensional representations of CGM profiles, which optionally are configured to be reconstructed to full-dimensional CGM profiles, are configured to allow: a) said subject, a technician, or a clinician to take a physical action in response to receiving said transmission to improve the safety and/or efficacy of therapy for said subject, or b) an interventional device to operationally take action in response to receiving said transmission to improve the safety and/or efficacy of therapy for said subject. In an embodiment, the transmitted reconstructed full-dimensional CGM profiles are configured to allow: a) said subject, a technician, or a clinician to take a physical action in response to receiving said transmission to improve the safety and/or efficacy of therapy for said subject, or b) an interventional device to operationally take action in response to receiving said transmission to improve the safety and/or efficacy of therapy for said subject.

An aspect of an embodiment of the present invention provides, among other things, a computer-implemented method for compressing continuous glucose monitor (CGM) data of a subject. The method may comprise: receiving CGM data profiles of said subject; extracting glycemic risk profiles from the CGM data profiles; compressing the CGM data profiles into low-dimensional representations using a trained neural network encoder via a cost function weighted by said extracted glycemic risk profiles; analyzing said low-dimensional representations of CGM data profiles to obtain analyzed low-dimensional results; and transmitting said analyzed results of said low-dimensional representations of CGM data profiles to a secondary source. The transmitted analyzed results of said low-dimensional representations of CGM profiles, which optionally are configured to be reconstructed to full-dimensional CGM profiles, are configured to allow: a) said subject, a technician, or a clinician to take a physical action in response to receiving said transmitted analyzed results to improve the safety and/or efficacy of therapy for said subject, or b) an interventional device to operationally take action in response to receiving said transmitted analyzed results to improve the safety and/or efficacy of therapy for said subject.

An aspect of an embodiment of the present invention provides, among other things, a system configured for compressing continuous glucose monitor (CGM) data of a subject. The system may comprise: a computer processor; a memory configured to store instructions that are executable by the computer processor. The processor may be configured to execute the instructions to: receive CGM data profiles of said subject; extract glycemic risk profiles from the CGM data profiles; compress the CGM data profiles into low-dimensional representations using a trained neural network encoder via a cost function weighted by said extracted glycemic risk profiles; analyze said low-dimensional representations of CGM data profiles to obtain analyzed low-dimensional results; and transmit said analyzed results of said low-dimensional representations of CGM data profiles to a secondary source. The said transmitted analyzed results of said low-dimensional representations of CGM profiles, which optionally are configured to be reconstructed to full-dimensional CGM profiles, are configured to allow: a) said subject, a technician, or a clinician to take a physical action in response to receiving said transmitted analyzed results to improve the safety and/or efficacy of therapy for said subject, or b) an interventional device to operationally take action in response to receiving said transmitted analyzed results to improve the safety and/or efficacy of therapy for said subject.

An aspect of an embodiment of the present invention provides, among other things, a computer program product, comprising a non-transitory computer-readable storage medium containing computer-executable instructions for compressing continuous glucose monitor (CGM) data of a subject. The instructions causing the computer to: receive CGM data profiles of said subject; extract glycemic risk profiles from the CGM data profiles; compress the CGM data profiles into low-dimensional representations using a trained neural network encoder via a cost function weighted by said extracted glycemic risk profiles; analyze said low-dimensional representations of CGM data profiles to obtain analyzed low-dimensional results; and transmit said analyzed results of said low-dimensional representations of CGM data profiles to a secondary source. The transmitted analyzed results of said low-dimensional representations of CGM profiles, which optionally are configured to be reconstructed to full-dimensional CGM profiles, are configured to allow: a) said subject, a technician, or a clinician to take a physical action in response to receiving said transmitted analyzed results to improve the safety and/or efficacy of therapy for said subject, or b) an interventional device to operationally take action in response to receiving said transmitted analyzed results to improve the safety and/or efficacy of therapy for said subject.

An aspect of an embodiment of the present invention provides, among other things, a system or method for compressing continuous glucose monitor (CGM) data for a subject and/or a technician, clinician, or for use with an interventional device. The system or method configures the CGM data to allow the subject, technician, clinician, or interventional device to take a physical action in response to receiving the transmission to improve the safety and/or efficacy of therapy for the subject.

FIG. 2 is a high-level functional block diagram of an embodiment of the present invention, or an aspect of an embodiment of the present invention. As shown in FIG. 2, a processor or controller 102 communicates with the glucose monitor or device 101 (or other interventional or diagnostic device), and optionally the insulin device 100 or an artificial pancreas. The glucose monitor or device 101 (or other interventional or diagnostic device) communicates with the subject 103 to monitor glucose levels of the subject 103. The processor or controller 102 is configured to perform the required calculations. Optionally, the insulin device 100 (or artificial pancreas) communicates with the subject 103 to deliver insulin to the subject 103. The processor or controller 102 is configured to perform the required calculations. The glucose monitor 101 (or other interventional or diagnostic device) and the insulin device 100 (or artificial pancreas) may be implemented as a separate device or as a single device. The processor 102 can be implemented locally in the glucose monitor 101, the insulin device 100, or a standalone device (or in any combination of two or more of the glucose monitor, insulin device, interventional device, diagnostic device or a stand along device). The processor 102 or a portion of the system can be located remotely such that the device is operated as a telemedicine device.

Referring to FIG. 3A, in its most basic configuration, computing device 144 typically includes at least one processing unit 150 and memory 146. Depending on the exact configuration and type of computing device, memory 146 can be volatile (such as RAM), non-volatile (such as ROM, flash memory, etc.) or some combination of the two.

Additionally, device 144 may also have other features and/or functionality. For example, the device could also include additional removable and/or non-removable storage including, but not limited to, magnetic or optical disks or tape, as well as writable electrical storage media. Such additional storage is the figure by removable storage 152 and non-removable storage 148. Computer storage media includes volatile and nonvolatile, removable and non-removable media implemented in any method or technology for storage of information such as computer readable instructions, data structures, program modules or other data. The memory, the removable storage and the non-removable storage are all examples of computer storage media. Computer storage media includes, but is not limited to, RAM, ROM, EEPROM, flash memory or other memory technology CDROM, digital versatile disks (DVD) or other optical storage, magnetic cassettes, magnetic tape, magnetic disk storage or other magnetic storage devices, or any other medium which can be used to store the desired information and which can accessed by the device. Any such computer storage media may be part of, or used in conjunction with, the device.

The device may also contain one or more communications connections 154 that allow the device to communicate with other devices (e.g. other computing devices). The communications connections carry information in a communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode, execute, or process information in the signal. By way of example, and not limitation, communication medium includes wired media such as a wired network or direct-wired connection, and wireless media such as radio, RF, infrared and other wireless media. As discussed above, the term computer readable media as used herein includes both storage media and communication media.

In addition to a stand-alone computing machine, embodiments of the invention can also be implemented on a network system comprising a plurality of computing devices that are in communication with a networking means, such as a network with an infrastructure or an ad hoc network. The network connection can be wired connections or wireless connections. As a way of example, FIG. 3B illustrates a network system in which embodiments of the invention can be implemented. In this example, the network system comprises computer 156 (e.g. a network server), network connection means 158 (e.g. wired and/or wireless connections), computer terminal 160, and PDA (e.g. a smart-phone) 162 (or other handheld or portable device, such as a cell phone, laptop computer, tablet computer, GPS receiver, MP3 player, handheld video player, pocket projector, etc. or handheld devices (or non-portable devices) with combinations of such features). In an embodiment, it should be appreciated that the module listed as 156 may be a glucose monitor device, artificial pancreas, and/or an insulin device (or other interventional or diagnostic device). Any of the components shown or discussed with FIG. 3B may be multiple in number. The embodiments of the invention can be implemented in anyone of the devices of the system. For example, execution of the instructions or other desired processing can be performed on the same computing device that is any one of 156, 160, and 162. Alternatively, an embodiment of the invention can be performed on different computing devices of the network system. For example, certain desired or required processing or execution can be performed on one of the computing devices of the network (e.g. server 156 and/or insulin device, artificial pancreas, or glucose monitor device (or other interventional or diagnostic device)), whereas other processing and execution of the instruction can be performed at another computing device (e.g. terminal 160) of the network system, or vice versa. In fact, certain processing or execution can be performed at one computing device (e.g. server 156 and/or insulin device, artificial pancreas, or glucose monitor device (or other interventional or diagnostic device)); and the other processing or execution of the instructions can be performed at different computing devices that may or may not be networked. For example, the certain processing can be performed at terminal 160, while the other processing or instructions are passed to device 162 where the instructions are executed. This scenario may be of particular value especially when the PDA 162 device, for example, accesses to the network through computer terminal 160 (or an access point in an ad hoc network). For another example, software to be protected can be executed, encoded or processed with one or more embodiments of the invention. The processed, encoded or executed software can then be distributed to customers. The distribution can be in a form of storage media (e.g. disk) or electronic copy.

FIG. 4 is a block diagram that illustrates a system 130 including a computer system 140 and the associated Internet 11 connection upon which an embodiment may be implemented. Such configuration is typically used for computers (hosts) connected to the Internet 11 and executing a server or a client (or a combination) software. A source computer such as a laptop, an ultimate destination computer and relay servers, for example, as well as any computer or processor described herein, may use the computer system configuration and the Internet connection shown in FIG. 4. The system 140 may be used as a portable electronic device such as a notebook/laptop computer, a media player (e.g., MP3 based or video player), a cellular phone, a Personal Digital Assistant (PDA), a glucose monitor device, an artificial pancreas, an insulin delivery device (or other interventional or diagnostic device), an image processing device (e.g., a digital camera or video recorder), and/or any other handheld computing devices, or a combination of any of these devices. Note that while FIG. 4 illustrates various components of a computer system, it is not intended to represent any particular architecture or manner of interconnecting the components; as such details are not germane to the present invention. It will also be appreciated that network computers, handheld computers, cell phones and other data processing systems which have fewer components or perhaps more components may also be used. The computer system of FIG. 4 may, for example, be an Apple Macintosh computer or PowerBook, or an IBM compatible PC. Computer system 140 includes a bus 137, an interconnect, or other communication mechanism for communicating information, and a processor 138, commonly in the form of an integrated circuit, coupled with bus 137 for processing information and for executing the computer executable instructions. Computer system 140 also includes a main memory 134, such as a Random Access Memory (RAM) or other dynamic storage device, coupled to bus 137 for storing information and instructions to be executed by processor 138.

Main memory 134 also may be used for storing temporary variables or other intermediate information during execution of instructions to be executed by processor 138. Computer system 140 further includes a Read Only Memory (ROM) 136 (or other non-volatile memory) or other static storage device coupled to bus 137 for storing static information and instructions for processor 138. A storage device 135, such as a magnetic disk or optical disk, a hard disk drive for reading from and writing to a hard disk, a magnetic disk drive for reading from and writing to a magnetic disk, and/or an optical disk drive (such as DVD) for reading from and writing to a removable optical disk, is coupled to bus 137 for storing information and instructions. The hard disk drive, magnetic disk drive, and optical disk drive may be connected to the system bus by a hard disk drive interface, a magnetic disk drive interface, and an optical disk drive interface, respectively. The drives and their associated computer-readable media provide non-volatile storage of computer readable instructions, data structures, program modules and other data for the general purpose computing devices. Typically computer system 140 includes an Operating System (OS) stored in a non-volatile storage for managing the computer resources and provides the applications and programs with an access to the computer resources and interfaces. An operating system commonly processes system data and user input, and responds by allocating and managing tasks and internal system resources, such as controlling and allocating memory, prioritizing system requests, controlling input and output devices, facilitating networking and managing files. Non-limiting examples of operating systems are Microsoft Windows, Mac OS X, and Linux.

The term "processor" is meant to include any integrated circuit or other electronic device (or collection of devices) capable of performing an operation on at least one instruction including, without limitation, Reduced Instruction Set Core (RISC) processors, CISC microprocessors, Microcontroller Units (MCUs), CISC-based Central Processing Units (CPUs), and Digital Signal Processors (DSPs). The hardware of such devices may be integrated onto a single substrate (e.g., silicon "die"), or distributed among two or more substrates. Furthermore, various functional aspects of the processor may be implemented solely as software or firmware associated with the processor.

Computer system 140 may be coupled via bus 137 to a display 131, such as a Cathode Ray Tube (CRT), a Liquid Crystal Display (LCD), a flat screen monitor, a touch screen monitor or similar means for displaying text and graphical data to a user. The display may be connected via a video adapter for supporting the display. The display allows a user to view, enter, and/or edit information that is relevant to the operation of the system. An input device 132, including alphanumeric and other keys, is coupled to bus 137 for communicating information and command selections to processor 138. Another type of user input device is cursor control 133, such as a mouse, a trackball, or cursor direction keys for communicating direction information and command selections to processor 138 and for controlling cursor movement on display 131. This input device typically has two degrees of freedom in two axes, a first axis (e.g., x) and a second axis (e.g., y), that allows the device to specify positions in a plane.

The computer system 140 may be used for implementing the methods and techniques described herein. According to one embodiment, those methods and techniques are performed by computer system 140 in response to processor 138 executing one or more sequences of one or more instructions contained in main memory 134. Such instructions may be read into main memory 134 from another computer-readable medium, such as storage device 135. Execution of the sequences of instructions contained in main memory 134 causes processor 138 to perform the process steps described herein. In alternative embodiments, hard-wired circuitry may be used in place of or in combination with software instructions to implement the arrangement. Thus, embodiments of the invention are not limited to any specific combination of hardware circuitry and software.

The term "computer-readable medium" (or "machine-readable medium") as used herein is an extensible term that refers to any medium or any memory, that participates in providing instructions to a processor, (such as processor 138) for execution, or any mechanism for storing or transmitting information in a form readable by a machine (e.g., a computer). Such a medium may store computer-executable instructions to be executed by a processing element and/or control logic, and data which is manipulated by a processing element and/or control logic, and may take many forms, including but not limited to, non-volatile medium, volatile medium, and transmission medium. Transmission media includes coaxial cables, copper wire and fiber optics, including the wires that comprise bus 137. Transmission media can also take the form of acoustic or light waves, such as those generated during radio-wave and infrared data communications, or other form of propagated signals (e.g., carrier waves, infrared signals, digital signals, etc.). Common forms of computer-readable media include, for example, a floppy disk, a flexible disk, hard disk, magnetic tape, or any other magnetic medium, a CD-ROM, any other optical medium, punch-cards, paper-tape, any other physical medium with patterns of holes, a RAM, a PROM, and EPROM, a FLASH- EPROM, any other memory chip or cartridge, a carrier wave as described hereinafter, or any other medium from which a computer can read.

Various forms of computer-readable media may be involved in carrying one or more sequences of one or more instructions to processor 138 for execution. For example, the instructions may initially be carried on a magnetic disk of a remote computer. The remote computer can load the instructions into its dynamic memory and send the instructions over a telephone line using a modem. A modem local to computer system 140 can receive the data on the telephone line and use an infra-red transmitter to convert the data to an infra-red signal. An infra-red detector can receive the data carried in the infra-red signal and appropriate circuitry can place the data on bus 137. Bus 137 carries the data to main memory 134, from which processor 138 retrieves and executes the instructions. The instructions received by main memory 134 may optionally be stored on storage device 135 either before or after execution by processor 138.

Computer system 140 also includes a communication interface 141 coupled to bus 137. Communication interface 141 provides a two-way data communication coupling to a network link 139 that is connected to a local network 111. For example, communication interface 141 may be an Integrated Services Digital Network (ISDN) card or a modem to provide a data communication connection to a corresponding type of telephone line. As another non-limiting example, communication interface 141 may be a local area network (LAN) card to provide a data communication connection to a compatible LAN. For example, Ethernet based connection based on IEEE802.3 standard may be used such as 10/100BaseT, 1000BaseT (gigabit Ethernet), 10 gigabit Ethernet (10 GE or 10 GbE or 10 GigE per IEEE Std 802.3ae-2002 as standard), 40 Gigabit Ethernet (40 GbE), or 100 Gigabit Ethernet (100 GbE as per Ethernet standard IEEE P802.3ba), as described in Cisco Systems, Inc. Publication number 1-587005-001-3 (6/99), "Internetworking Technologies Handbook", Chapter 7: "Ethernet Technologies", pages 7-1 to 7-38, which is incorporated in its entirety for all purposes as if fully set forth herein. In such a case, the communication interface 141 typically include a LAN transceiver or a modem, such as Standard Microsystems Corporation (SMSC) LAN91C111 10/100 Ethernet transceiver described in the Standard Microsystems Corporation (SMSC) data-sheet "LAN91C111 10/100 Non-PCI Ethernet Single Chip MAC+PHY" Data-Sheet, Rev. 15 (02-20-04), which is incorporated in its entirety for all purposes as if fully set forth herein.

Wireless links may also be implemented. In any such implementation, communication interface 141 sends and receives electrical, electromagnetic or optical signals that carry digital data streams representing various types of information. Network link 139 typically provides data communication through one or more networks to other data devices. For example, network link 139 may provide a connection through local network 111 to a host computer or to data equipment operated by an Internet Service Provider (ISP) 142. ISP 142 in turn provides data communication services through the world wide packet data communication network Internet 11. Local network 111 and Internet 11 both use electrical, electromagnetic or optical signals that carry digital data streams. The signals through the various networks and the signals on the network link 139 and through the communication interface 141, which carry the digital data to and from computer system 140, are exemplary forms of carrier waves transporting the information.

A received code may be executed by processor 138 as it is received, and/or stored in storage device 135, or other non-volatile storage for later execution. In this manner, computer system 140 may obtain application code in the form of a carrier wave.

The concepts of a) compressing and clustering of daily continuous glucose monitor (CGM) profiles or b) compressing continuous glucose monitor (CGM) data of a subject have been developed by the present inventor, and may be implemented and utilized with the related processors, networks, computer systems, internet, and components and functions according to the schemes disclosed herein.

FIG. 5 illustrates a system in which one or more embodiments of the invention can be implemented using a network, or portions of a network or computers. Although the present invention glucose monitor, artificial pancreas or insulin device (or other interventional or diagnostic device) may be practiced without a network.

FIG. 5 diagrammatically illustrates an exemplary system in which examples of the invention can be implemented. In an embodiment the glucose monitor, artificial pancreas or insulin device (or other interventional or diagnostic device) may be implemented by the subject (or patient) locally at home or other desired location. However, in an alternative embodiment it may be implemented in a clinic setting or assistance setting. For instance, referring to FIG. 5, a clinic setup 158 provides a place for doctors (e.g. 164) or clinician/assistant to diagnose patients (e.g. 159) with diseases related with glucose and related diseases and conditions. A glucose monitoring device 10 can be used to monitor and/or test the glucose levels of the patient—as a standalone device. It should be appreciated that while only glucose monitor device 10 is shown in the figure, the system of the invention and any component thereof may be used in the manner depicted by FIG. 5. The system or component may be affixed to the patient or in communication with the patient as desired or required. For example the system or combination of components thereof—including a glucose monitor device 10 (or other related devices or systems such as a controller, and/or an artificial pancreas, an insulin pump (or other interventional or diagnostic device), or any other desired or required devices or components)—may be in contact, communication or affixed to the patient through tape or tubing (or other medical instruments or components) or may be in communication through wired or wireless connections. Such monitor and/or test can be short term (e.g. clinical visit) or long term (e.g. clinical stay or family). The glucose monitoring device outputs can be used by the doctor (clinician or assistant) for appropriate actions, such as insulin injection or food feeding for the patient, or other appropriate actions or modeling. Alternatively, the glucose monitoring device output can be delivered to computer terminal 168 for instant or future analyses. The delivery can be through cable or wireless or any other suitable medium. The glucose monitoring device output from the patient can also be delivered to a portable device, such as PDA 166. The glucose monitoring device outputs with improved accuracy can be delivered to a glucose monitoring center 172 for processing and/or analyzing. Such delivery can be accomplished in many ways, such as network connection 170, which can be wired or wireless.

In addition to the glucose monitoring device outputs, errors, parameters for accuracy improvements, and any accuracy related information can be delivered, such as to computer 168, and/or glucose monitoring center 172 for performing error analyses. This can provide a centralized accuracy monitoring, modeling and/or accuracy enhancement for glucose centers, due to the importance of the glucose sensors.

Examples of the invention can also be implemented in a standalone computing device associated with the target glucose monitoring device, artificial pancreas, and/or insulin device (or other interventional or diagnostic device). An exemplary computing device (or portions thereof) in which examples of the invention can be implemented is schematically illustrated in FIG. 3A.

FIG. 6 is a block diagram illustrating an example of a machine upon which one or more aspects of embodiments of the present invention can be implemented. FIG. 6 illustrates a block diagram of an example machine 400 upon which one or more embodiments (e.g., discussed methodologies) can be implemented (e.g., run).

Examples of machine 400 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 400) and software architectures that can be deployed in example embodiments.

In an example, the machine 400 can operate as a standalone device or the machine 400 can be connected (e.g., networked) to other machines.

In a networked deployment, the machine 400 can operate in the capacity of either a server or a client machine in server-client network environments. In an example, machine 400 can act as a peer machine in peer-to-peer (or other distributed) network environments. The machine 400 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 400. Further, while only a single machine 400 is illustrated, the term "machine" shall also be taken to include any collection of machines that individually or jointly execute a set (or multiple sets) of instructions to perform any one or more of the methodologies discussed herein.

Example machine (e.g., computer system) 400 can include a processor 402 (e.g., a central processing unit (CPU), a graphics processing unit (GPU) or both), a main memory 404 and a static memory 406, some or all of which can communicate with each other via a bus 408. The machine 400 can further include a display unit 410, an alphanumeric input device 412 (e.g., a keyboard), and a user interface (UI) navigation device 411 (e.g., a mouse). In an example, the display unit 410, input device 412 and UI navigation device 414 can be a touch screen display. The machine 400 can additionally include a storage device (e.g., drive unit) 416, a signal generation device 418 (e.g., a speaker), a network interface device 420, and one or more sensors 421, such as a global positioning system (GPS) sensor, compass, accelerometer, or other sensor.

The storage device 416 can include a machine readable medium 422 on which is stored one or more sets of data structures or instructions 424 (e.g., software) embodying or utilized by any one or more of the methodologies or functions described herein. The instructions 424 can also reside, completely or at least partially, within the main memory 404, within static memory 406, or within the processor 402 during execution thereof by the machine 400. In an example, one or any combination of the processor 402, the main memory 404, the static memory 406, or the storage device 416 can constitute machine readable media.

While the machine readable medium 422 is illustrated as a single medium, the term "machine readable medium" can include a single medium or multiple media (e.g., a centralized or distributed database, and/or associated caches and servers) that configured to store the one or more instructions 424. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 424 can further be transmitted or received over a communications network 426 using a transmission medium via the network interface device 420 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

It should be appreciated that any of the components or modules referred to with regards to any of the present invention embodiments discussed herein, may be integrally or separately formed with one another. Further, redundant functions or structures of the components or modules may be implemented. Moreover, the various components may be communicated locally and/or remotely with any user/clinician/patient or machine/system/computer/processor. Moreover, the various components may be in communication via wireless and/or hardwire or other desirable and available communication means, systems and hardware. Moreover, various components and modules may be substituted with other modules or components that provide similar functions.

It should be appreciated that the device and related components discussed herein may take on all shapes along the entire continual geometric spectrum of manipulation of x, y and z planes to provide and meet the anatomical, environmental, and structural demands and operational requirements. Moreover, locations and alignments of the various components may vary as desired or required.

It should be appreciated that various sizes, dimensions, contours, rigidity, shapes, flexibility and materials of any of the components or portions of components in the various embodiments discussed throughout may be varied and utilized as desired or required.

It should be appreciated that while some dimensions are provided on the aforementioned figures, the device may constitute various sizes, dimensions, contours, rigidity, shapes, flexibility and materials as it pertains to the components or portions of components of the device, and therefore may be varied and utilized as desired or required.

Although example embodiments of the present disclosure are explained in some instances in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" may be any applicable human, animal, or other organism, living or dead, or other biological or molecular structure or chemical environment, and may relate to particular components of the subject, for instance specific tissues or fluids of a subject (e.g., human tissue in a particular area of the body of a living subject), which may be in a particular location of the subject, referred to herein as an "area of interest" or a "region of interest."

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. All references cited and discussed in this specification are incorporated herein by reference in their entireties and to the same extent as if each reference was individually incorporated by reference.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, 4.24, and 5). Similarly, numerical ranges recited herein by endpoints include subranges subsumed within that range (e.g. 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

Additional descriptions of aspects of the present disclosure will now be provided with reference to the accompanying drawings. The drawings form a part hereof and show, by way of illustration, specific embodiments or examples. In referring to the drawings, like numerals represent like elements throughout the several figures.

BRIEF DESCRIPTION OF THE DRAWINGS

The foregoing and other objects, features and advantages of the present invention, as well as the invention itself, will be more fully understood from the following description of preferred embodiments, when read together with the accompanying drawings The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF EXEMPLARY EMBODIMENTS

Figure 1:
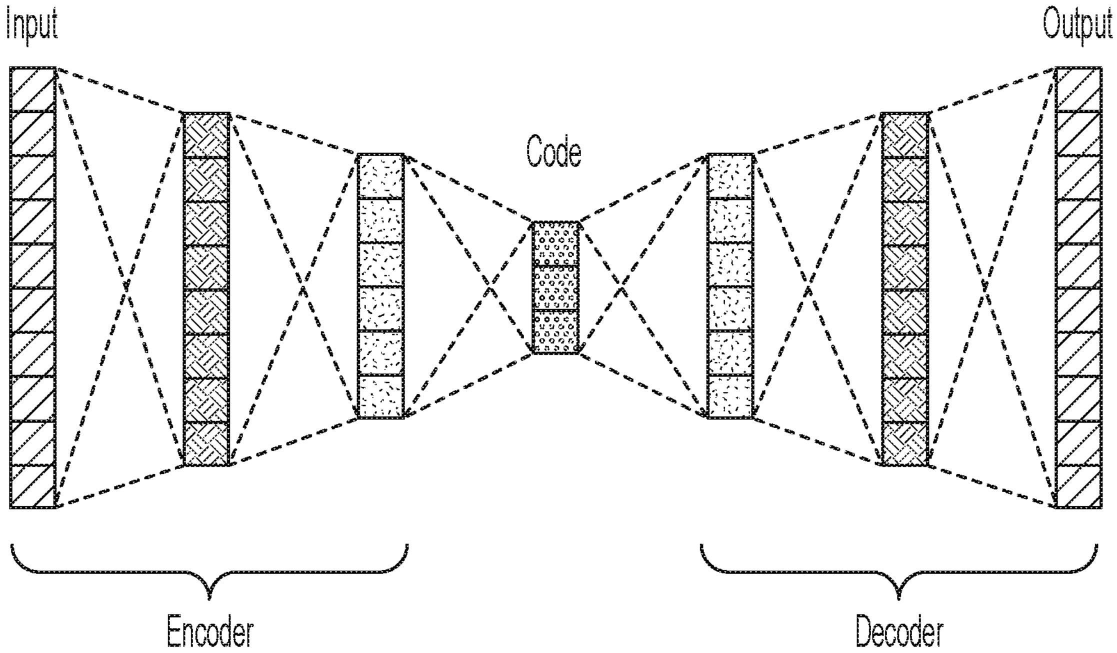
FIG. 1 schematically represents the structure of a neural network.
Figure 2:
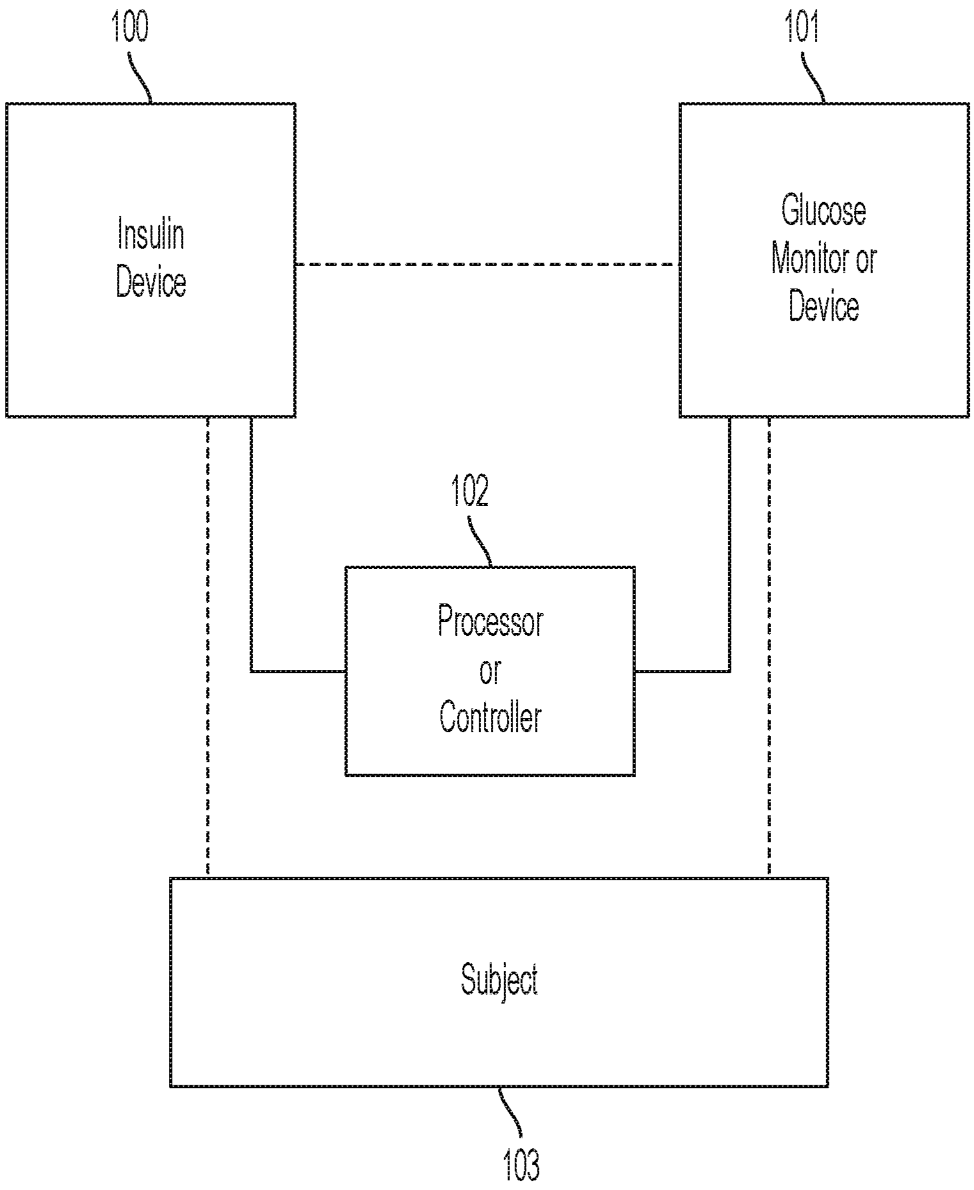
FIG. 2 is a high-level functional block diagram of an embodiment of the present invention.
Figure 3A:
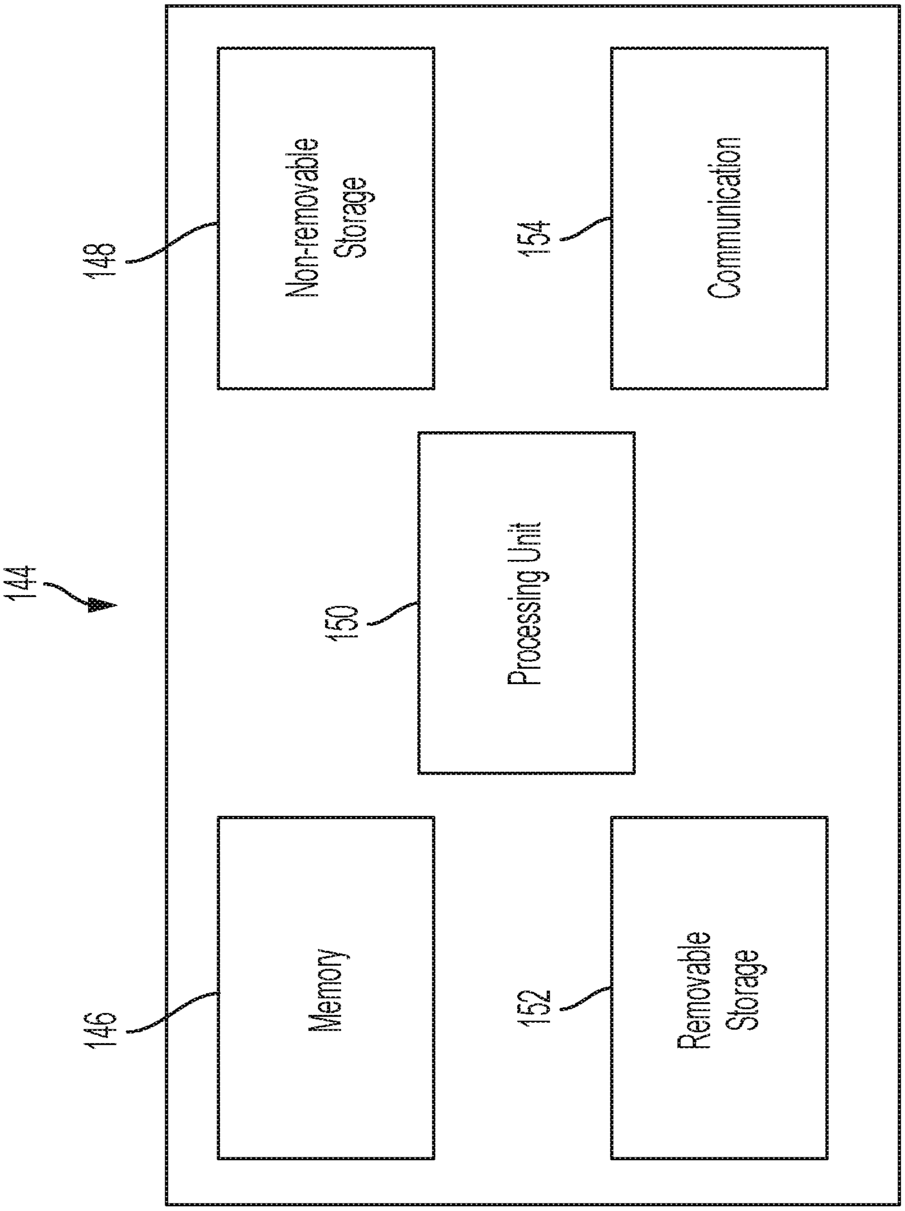
FIG. 3A is a basic configuration of an embodiment of the present invention, including a computing device with typically at least one processing unit and memory storage.
Figure 3B:
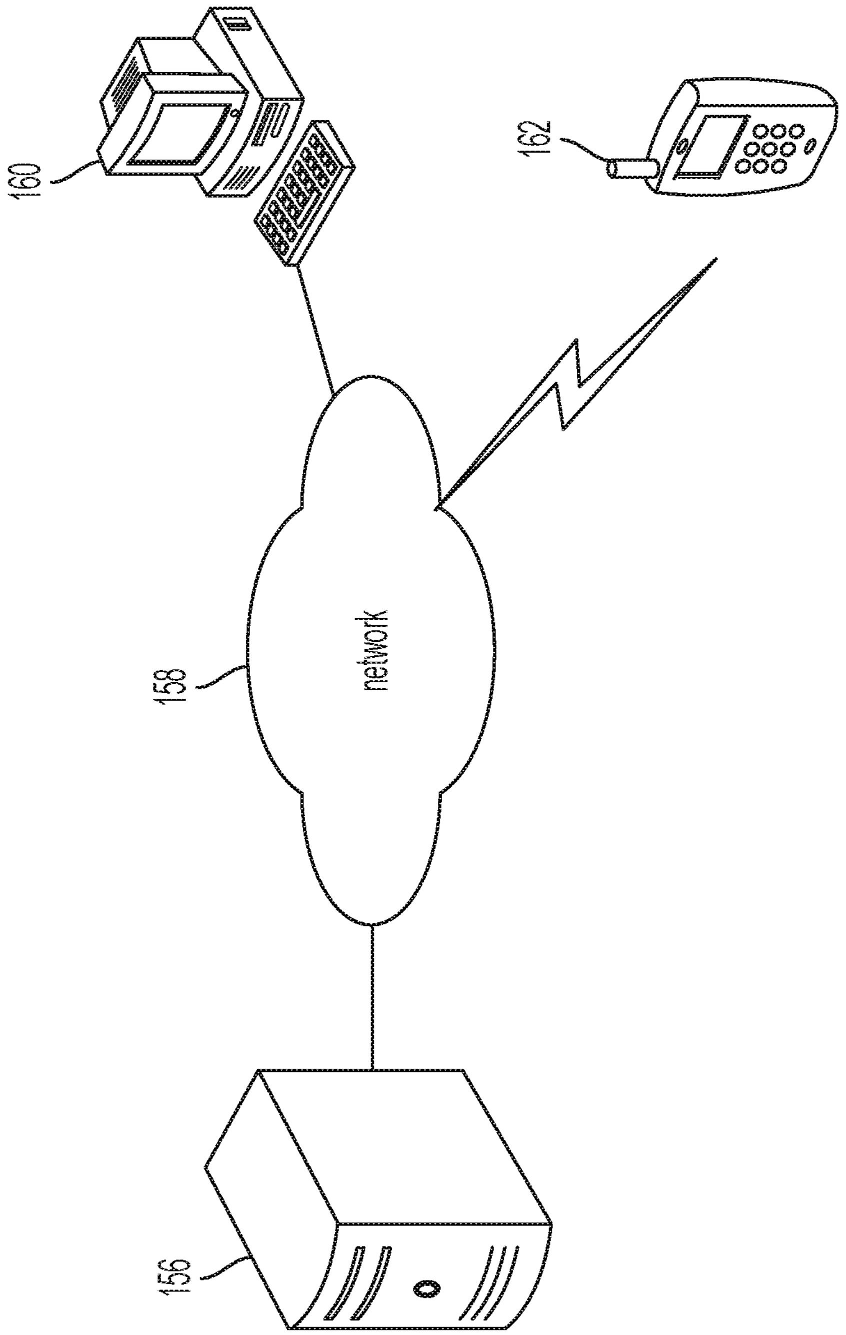
FIG. 3B illustrates a network system in which embodiments of the invention can be implemented.
Figure 4:
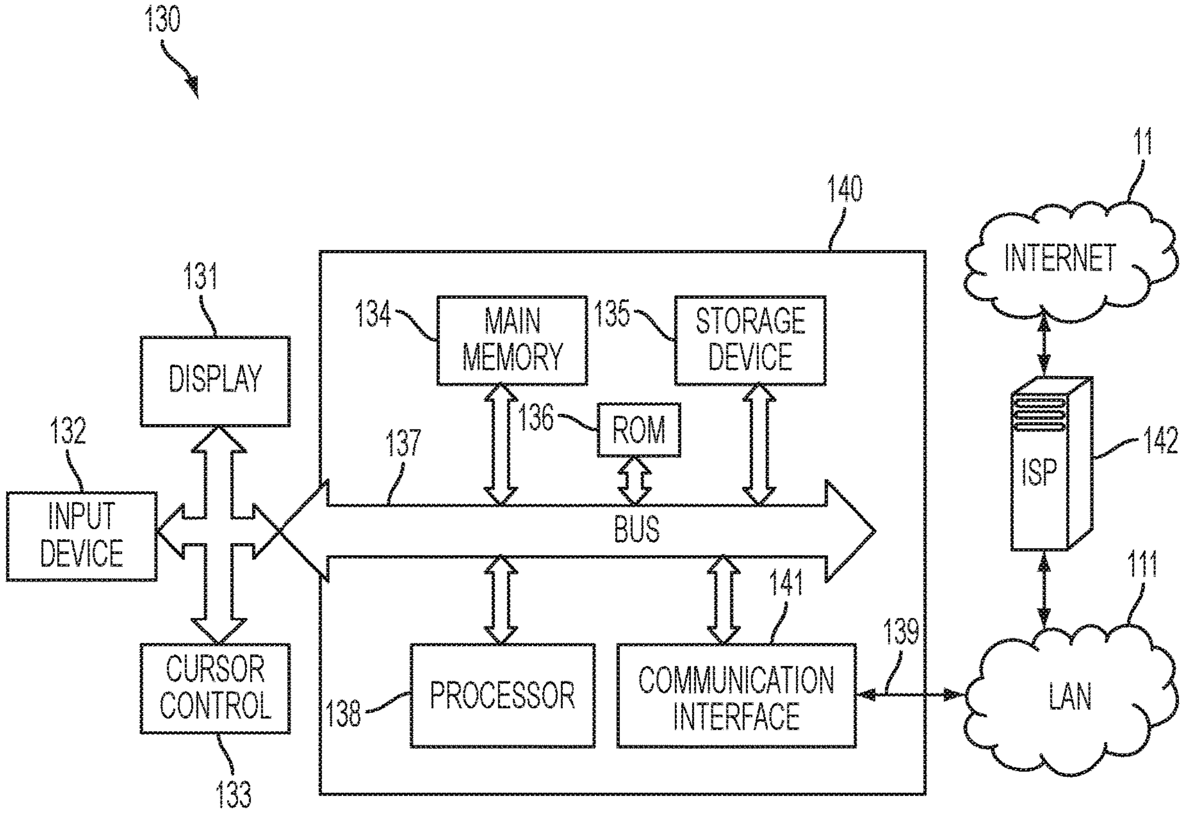
FIG. 4 is a block diagram that illustrates a system, including a computer system and the associated internet connection upon which an embodiment may be implemented.
Figure 5:
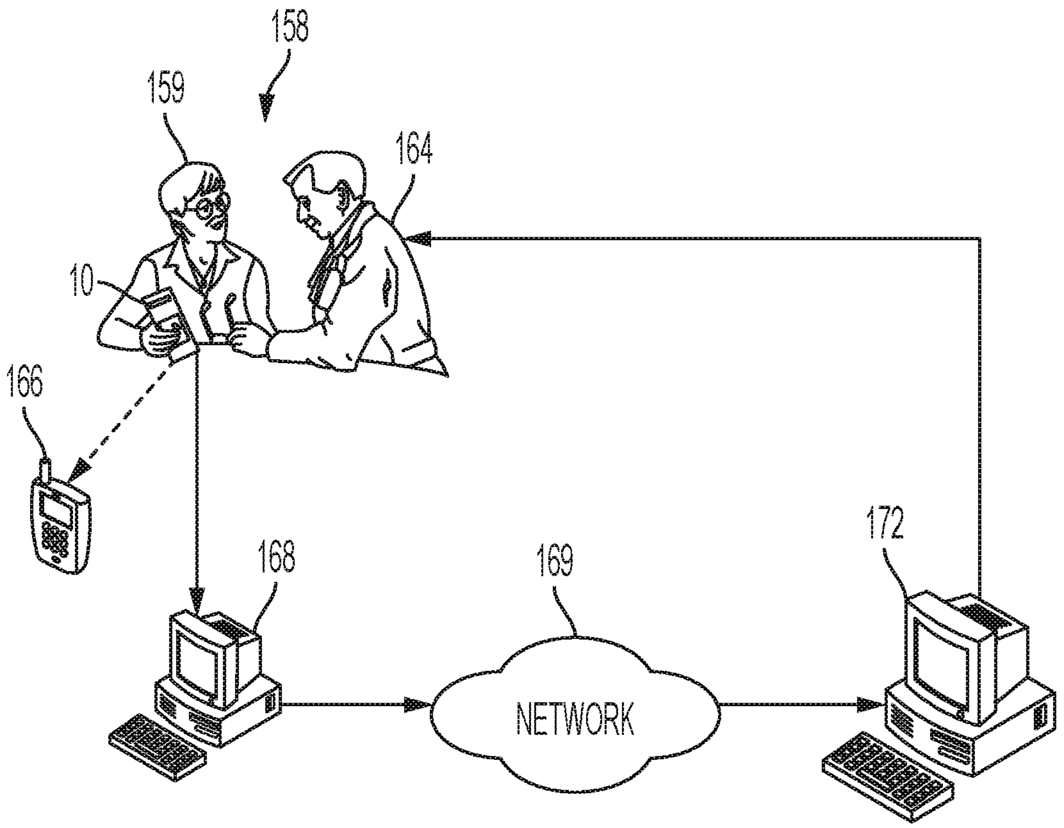
FIG. 5 illustrates a system in which one or more embodiments of the invention can be implemented using a network, or portions of a network or computers.
Figure 6:
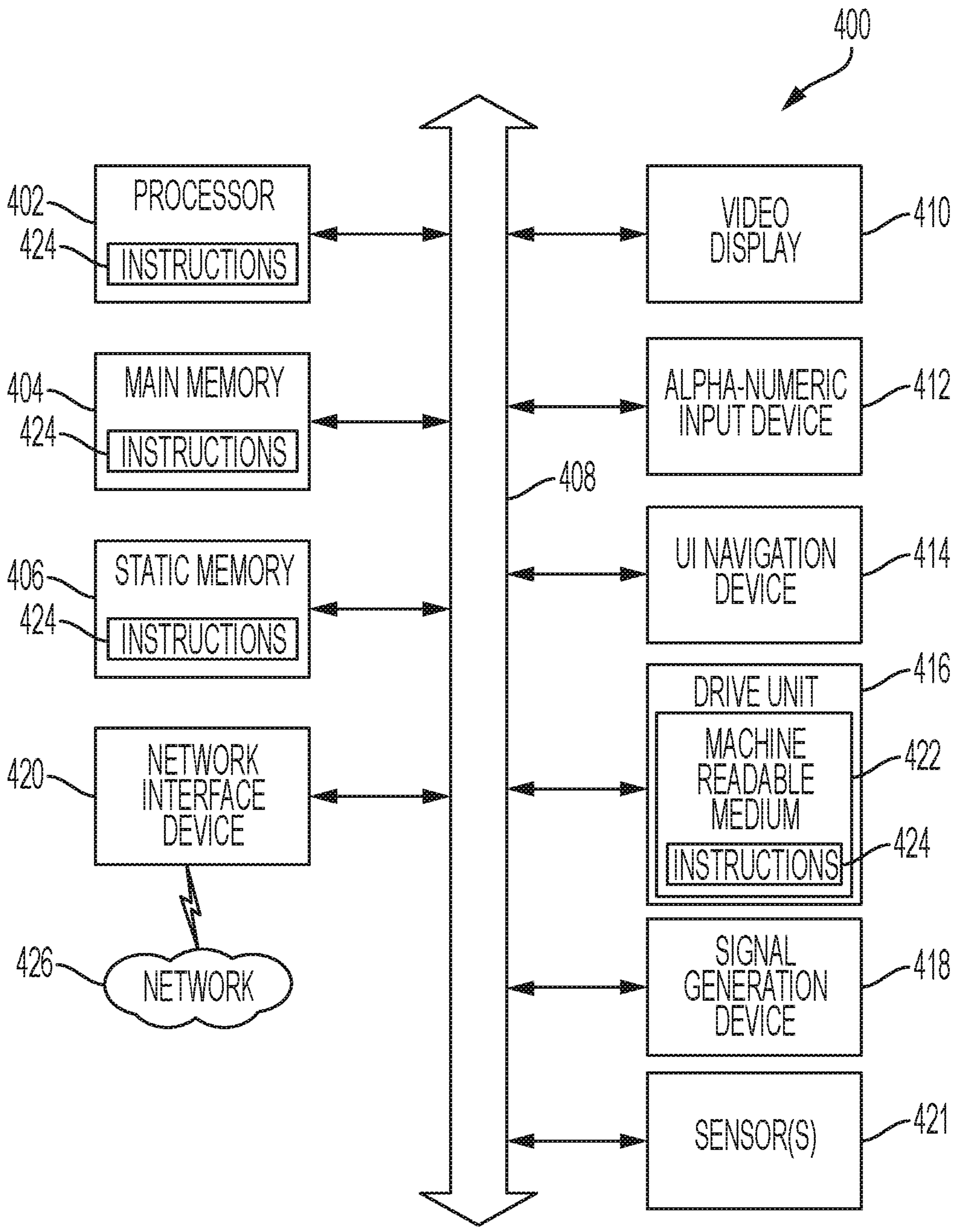
FIG. 6 is a block diagram illustrating an example of a machine upon which one or more aspects of embodiments of the present invention can be implemented.

A major problem common for common BG measures is their insensitivity to hypoglycemia and their inherent bias towards hyperglycemic readings, which is reflected by the historically poor prediction of hypoglycemic episodes (8 to 18% as reviewed in the previous section). In previous studies we have found that the basis for that poor prediction appeared to be mathematical, rather than clinical: it lies in the fact that the Blood Glucose (BG) measurement scale is substantially asymmetric and skewed towards hyperglycemia. (See Kovatchev B P, et al., "Symmetrization of the Blood Glucose Measurement Scale and its Applications", Diabetes Care. 1997; 20 (11): 1655-1658. https:doi.org/10.2337/diacare.20.11.1655; of which is hereby incorporated by reference herein in its entirety; See Kovatchev, B P, "Metrics for Glycaemic Control—from HbA1c to Continuous Glucose Monitoring", Nature Reviews Endocrinology. 2017; 13 (7): 425-436. http://doi.org/10/1038/nrendo.2017.3, of which is hereby incorporated by reference herein in its entirety; and See U.S. Utility patent application Ser. No. 12/159,891, entitled "Method, System and Computer Program Product for Evaluation of Blood Glucose Variability in Diabetes from Self-Monitoring Data", filed Jul. 2, 2008; Publication No. 2009/0171589, Jul. 2, 2009; of which is hereby incorporated by reference herein in its entirety.) In other words, the "numerical center" of the data is substantially separated from its "clinical center." Thus, clinical conclusions, based on numerical methods, will be less accurate for the constricted hypoglycemic range and will be biased towards hyperglycemia. Thus, the standard deviation (SD) of BG, the M-values and MAGE are mostly correlated to hyperglycemic episodes. The LI is very similar to our previously reported absolute BG rate of change the difference is the squared denominator in the formula. Because it is a differential statistic, it puts more emphasis on hypoglycemia than traditional BG-based statistics. Thus, the LI correlates better than SD of BG, M-value and MAGE with future significant hypoglycemic episodes. However, it is still substantially less accurate that our risk-based methods (introduced in this disclosure) in predicting hypoglycemic episodes.

In order to correct the numerical problem created by the asymmetry of the BG scale we have introduced a mathematical transformation that summarizes the BG scale (See Kovatchev B P, et al., "Symmetrization of the Blood Glucose Measurement Scale and its Applications", Diabetes Care. 1997; 20 (11): 1655-1658. https://doi.org/10.2337/diacare.20.11.1655, of which is hereby incorporated by reference herein) and, based on this transformation, we developed our theory of risk analysis of BG data. (See Kovatchev, B P, "Metrics for Glycaemic Control—from HbA1c to Continuous Glucose Monitoring", Nature Reviews Endocrinology. 2017; 13 (7): 425-436. http://doi.org/10/1038/nrendo.2017.3, of which is hereby incorporated by reference herein in its entirety; and See U.S. Utility patent application Ser. No. 12/159,891, entitled "Method, System and Computer Program Product for Evaluation of Blood Glucose Variability in Diabetes from Self-Monitoring Data", filed Jul. 2, 2008; Publication No. 2009/0171589, Jul. 2, 2009, of which is hereby incorporated by reference herein in its entirety.)

Figure 7:
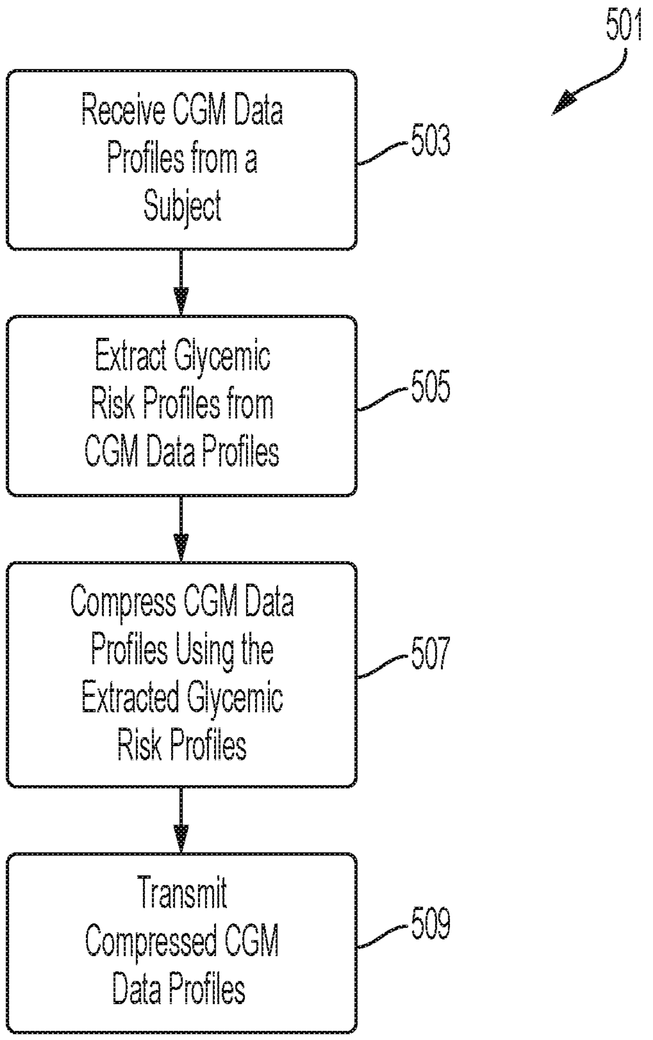
FIG. 7 is a flow diagram of a method for compressing continuous glucose monitor (CGM) profiles of a subject.

FIG. 7 is a flow diagram of a method 501 for compressing continuous glucose monitor (CGM) profiles of a subject. The method 501 can be performed by a system of one or more appropriately-programmed computers in one or more locations. At step 503, the system receives CGM data profiles of said subject. At step 505, the system extracts glycemic risk profiles from the CGM data profiles. At step 507, the system compresses the CGM data profiles into low-dimensional representations using a trained neural network encoder via a cost function weighted by said extracted glycemic risk profiles. The neural networks at step 507 can include one or more artificial neural networks (ANNs), convolutional neural networks (CNNs), or recurrent neural networks (RNNs). More specifically, the CNN can be an autoencoder. The cost function at step 507 can include a maximum likelihood cost function, an absolute deviation cost function, or a mean squared error cost function where the glycemic risk profile is weighted with an exponent from 0 to any positive number, and in an embodiment the exponent may be from 0 to 1. At step 509, the system transmits said low-dimensional representations of CGM profiles to a secondary source, which can include one or more local memory, remote memory, or a display or graphical user interface. Afterward, the transmitted low-dimensional representations of CGM profiles are configured to allow a clinician or an interventional device to take an action in response to receiving said transmission to improve the safety and/or efficacy of therapy for said subject.

For example, in an embodiment the improvement of the safety and/or efficacy of therapy for the subject may include one or more of the following: preventing a hypoglycemic event(s) from occurring in said subject; preventing a hyperglycemic event(s) from occurring in said subject; reducing excessive glucose variability occurring in said subject; reducing postprandial glucose excursions occurring in said subject; reducing the risk for hypoglycemia; reducing the risk for hyperglycemia; optimizing delivery of antidiabetic drugs/compounds (including, insulin); or lowering glycated hemoglobin (HbA1c).

In embodiment, the interventional device may include one or more of anyone of the following: insulin pump device; decision support system; low glucose suspend system; connected insulin pens; automated insulin delivery systems; or intelligent patch or intelligent transplant (as well as any other available interventional devices).

For example, the mean squared error cost function can be represented by the following formula:

$$\sum_{i=1}^{n} w_i^{[0,1]}(Y_i - \hat{Y}_i)^2$$

wherein $Y_i$=observed result, $\hat{Y}_i$=predicted result, $w_i$=the weight of the $i^{th}$ glycemic risk profile, and n=number of profiles. The mean squared error cost function is weighted by the corresponding glycemic risk profile or a function of the corresponding glycemic risk profile. In an embodiment the sum of weights equals 1, wherein $$\sum_{i=1}^{n} w_i = 1$$

and the glycemic risk profile is weighted with an exponent from 0 to 1.

In an embodiment, the received CGM data profiles can be preprocessed prior to the extraction. For example, such preprocessing can include discarding a specified percentage of incomplete CGM data profiles, wherein the specified percentage of incomplete CGM data profiles includes one of the following: range of 0 percent and less than about 50 percent; range of 0 percent and less than about 40 percent; range of 0 percent and less than about 30 percent; range of 0 percent and less than about 20 percent; range of 0 percent and less than about 10 percent; or about 10 percent.

Figure 8:
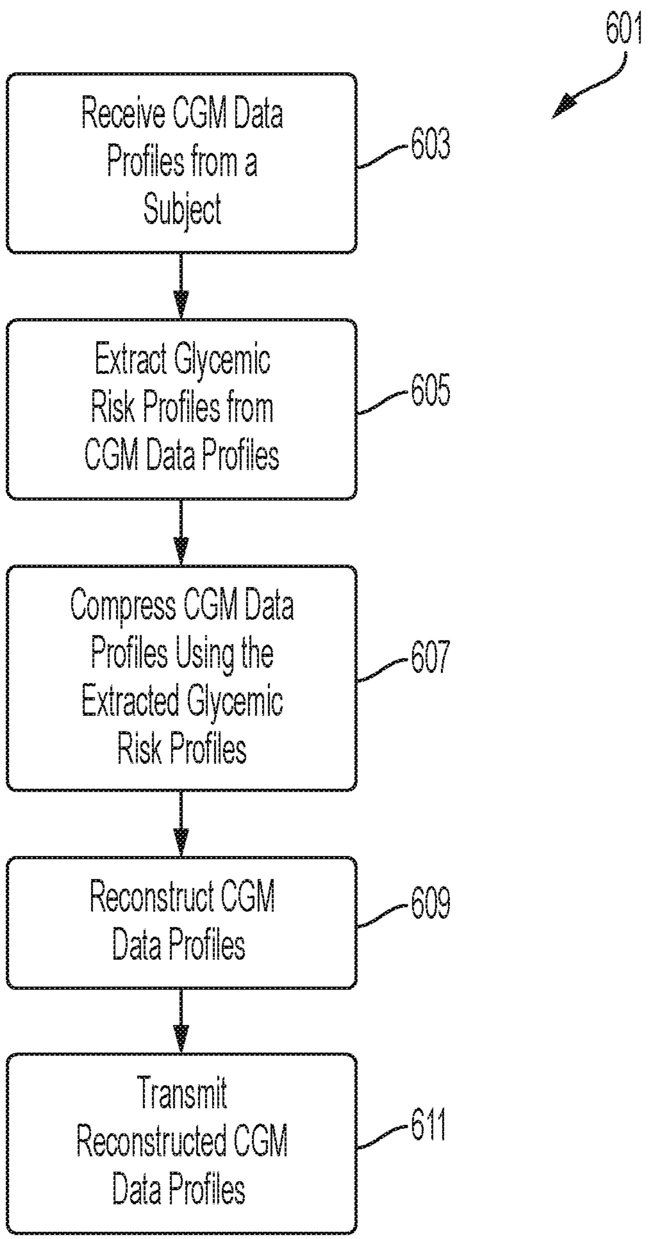
FIG. 8 is a flow diagram of an alternative method for compressing CGM profiles of a subject.

FIG. 8 is a flow diagram of a method 601 for compressing continuous glucose monitor (CGM) profiles. The method 601 can be performed by a system of one or more appropriately-programmed computers in one or more locations. At step 603, the system receives CGM data profiles of said subject. At step 605, the system extracts glycemic risk profiles from the CGM data profiles. At step 607, the system compresses the CGM data profiles into low-dimensional representations using a trained neural network encoder via a cost function weighted by said extracted glycemic risk profiles. The neural networks at step 607 can include one or more artificial neural networks, convolutional neural networks, or recurrent neural networks. More specifically, the CNN can be an autoencoder. The cost function at step 607 can include a maximum likelihood cost function, an absolute deviation cost function, or a mean squared error cost function where the glycemic risk profile is weighted with an exponent from 0 to any positive number, and in an embodiment the exponent may be from 0 to 1. At step 609, the system reconstructs said low-dimensional representations of CGM profiles to full-dimensional CGM profiles. At step 611, the system transmits said reconstructed full-dimensional CGM profiles to a secondary source, which can include one or more local memory, remote memory, or display/graphical user interface. Afterward, the transmitted reconstructed full-dimensional representations of CGM profiles are configured to allow a clinician or an interventional device to take an action in response to receiving said transmission to improve the safety and/or efficacy of therapy for said subject.

Figure 9:
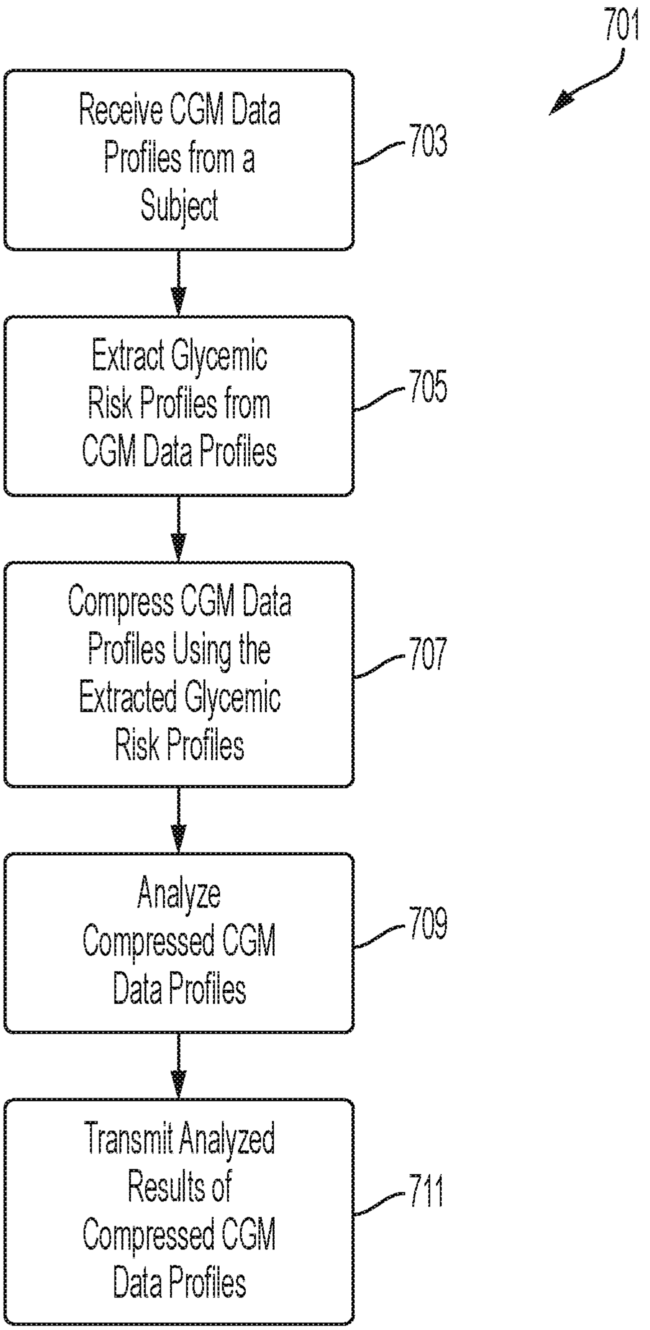
FIG. 9 is a flow diagram of another alternative method for compressing CGM profiles of a subject.

FIG. 9 is a flow diagram of a method 701 for compressing continuous glucose monitor (CGM) profiles. The method 701 can be performed by a system of one or more appropriately-programmed computers in one or more locations. At step 703, the system receives CGM data profiles of said subject. At step 705, the system extracts glycemic risk profiles from the CGM data profiles. At step 707, the system compresses the CGM data profiles into low-dimensional representations using a trained neural network encoder via a cost function weighted by said extracted glycemic risk profiles. The neural networks at step 707 can include one or more artificial neural networks, convolutional neural networks, or recurrent neural networks. More specifically, the CNN can be an autoencoder. The cost function at step 707 can include a maximum likelihood cost function, an absolute deviation cost function, or a mean squared error cost function where the glycemic risk profile is weighted with an exponent from 0 to any positive number, and in an embodiment the exponent may be from 0 to 1. At step 709, the system analyzes said low-dimensional representations of CGM data profiles to obtain analyzed low-dimensional results. The analysis at step 709 can include one or more methods such as k-mean clustering, t-distributed stochastic neighbor embedding, principal component analysis, or independent component analysis. At step 711, the system transmits said analyzed results of said low-dimensional representations of CGM data profiles to a secondary source, which can include one or more local memory, remote memory, or display/graphical user interface. Afterward, the transmitted analyzed results of said low-dimensional representations of CGM profiles are configured to allow a clinician or an interventional device to take an action in response to receiving said transmission to improve the safety and/or efficacy of therapy for said subject.

EXAMPLES

Practice of an aspect of an embodiment (or embodiments) of the invention will be still more fully understood from the following examples and experimental results, which are presented herein for illustration only and should not be construed as limiting the invention in any way.

Example and Experimental Results Set No. 1

Clinical Data and Data Preparation. In this study the present inventor used CGM data from the recently completed International Diabetes Closed Loop (iDCL) Trial. As part of the trial, two randomized controlled trials comparing a Closed Loop Control (CLC) system vs. Sensor Augmented Pump (SAP) at home were performed: protocols iDCL-1 (NCT02985866) and iDCL-3 (NCT03563313). In these two studies (iDCL-1/iDCL-3), N=125/N=168 participants were randomized 1:1/2:1 to CLC or SAP for 3/6 months. iDCL-1 data was used to develop the different feature learning techniques (below) extracting low dimensional temporal features from daily CGM profiles further used to extracted clusters from these features using the K-means method. With the trained feature extractor and clusters, the daily CGM profiles in iDCL3 were also classified for testing purposes. To prepare the data for analysis, the present inventor discarded CGM daily profiles which have more than 10% of missing data. In the remaining profiles we reconstruct the missing values by linear interpolation. About 10% of the CGM data was discarded.

Feature Extraction: Non-Data-Driven Methods.

Baseline A. Subsampling: Given a fixed number of features N, a subsampling method is implemented by splitting a 24-hour CGM profile into N equal-spaced interval and calculate the mean of glucose of each interval as a feature. The reconstruction of CGM profiles is achieved by linearly interpolating the features from subsampling.

Baseline B. Discrete Cosine Transform approximate: Any signal of time (t) on a finite period (P) can be represent as a Discrete Fourier series as follow:

$$X_k = \sum_{n=0}^{N-1} x_n \cos\left[\frac{\pi}{N}\left(n + \frac{1}{2}\right)k\right] \quad k = 0, \ldots , N - 1$$

Feature Extraction: Data-Driven Methods.

Autoencoder: An autoencoder is a framework of artificial neural networks used to reduce data dimension in an unsupervised manner. An autoencoder neural network (AutoNN) was adopted to compress and denoise data and boosted the performance of a following supervised learning.

Figure 10:
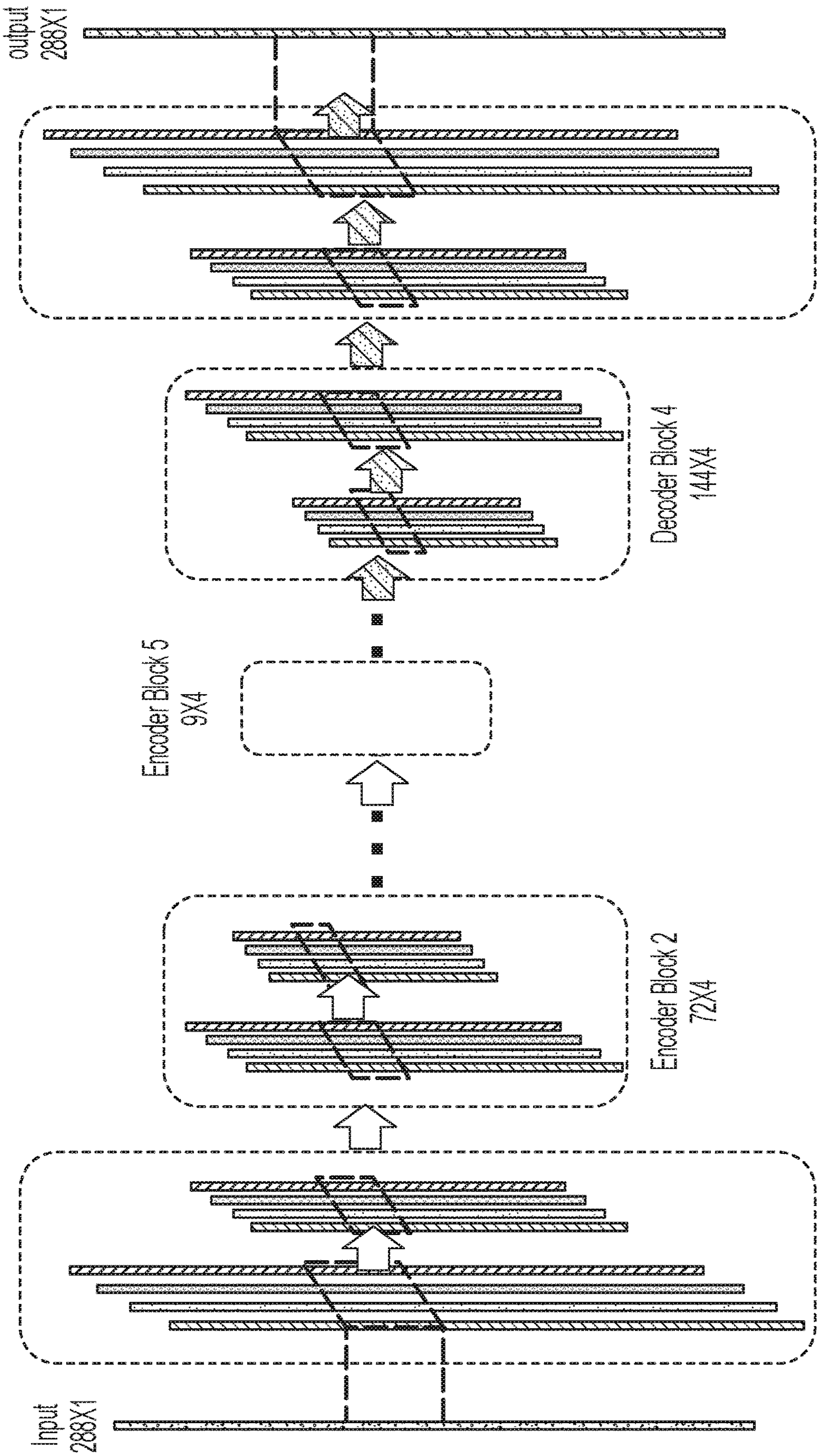
FIG. 10 describes the structure of a neural network analyzing CGM data.

In this work, the present inventor adopted the framework of AutoNN and utilized the structure of one-dimensional convolution neural work for each layer. The structure of the neural network is described in FIG. 10. The left half of this flowchart shows the "encoder" structure. The input of raw CGM data is injected from the left—most side of the encoder and passed through several encoder blocks. Each encoder block contains a nonlinear Convolution layer and a Maxpooling layer to reduce the dimension to half. Output of the last encoder block is flattened to a vector with length N. The "decoder" structure in the right side applies the opposite operations. Each decoder block contains a nonlinear Convolution layer and an Upsampling layer to double the dimension of the input. Output of the last decoder block is flattened to a vector with length 288 which is the same dimension of raw CGM data.

The present inventor adopted four different cost functions which lead to three variants of the Autoencoder algorithm:

Auto-origin, cost function: mean squared error

Auto-risk050, cost function: mean squared error weighted with hypoglycemia risk to the power of 0.50

Auto-risk075, cost function: mean squared error weighted with hypoglycemia risk to the power of 0.75

Auto-risk100, cost function: mean squared error weighted with hypoglycemia risk

Principal Component Analysis and Independent Component Analysis: We also applied standard principal component analysis (PCA) and independent Component Analysis (ICA) as data-driven unsupervised feature learning methods. In PCA and ICA methods, the data matrix is established in such a way that each row is the vector of a daily CGM profile in the corresponding dataset.

Comparing Different Compact Representations

With a fixed feature number N, all methods are compared by the following three ways:

Point-to-point reconstruction error

Glycemic metrics error

Clustering and Visualization

Based on the features extracted from CGM daily profiles, the present inventor performed a K-means clustering. The present inventor displays each cluster with an envelop plot, plotting the mean curve with a closure area bounded by ±δ. To visualize the distribution of each cluster, we also applied the t-Distributed Stochastic Neighbor Embedding (t-SNE) technique. This technique helps to, among other things, reduce the feature dimension N into a 2-D space while maintaining local relative distances between points.

Results

Figure 11:
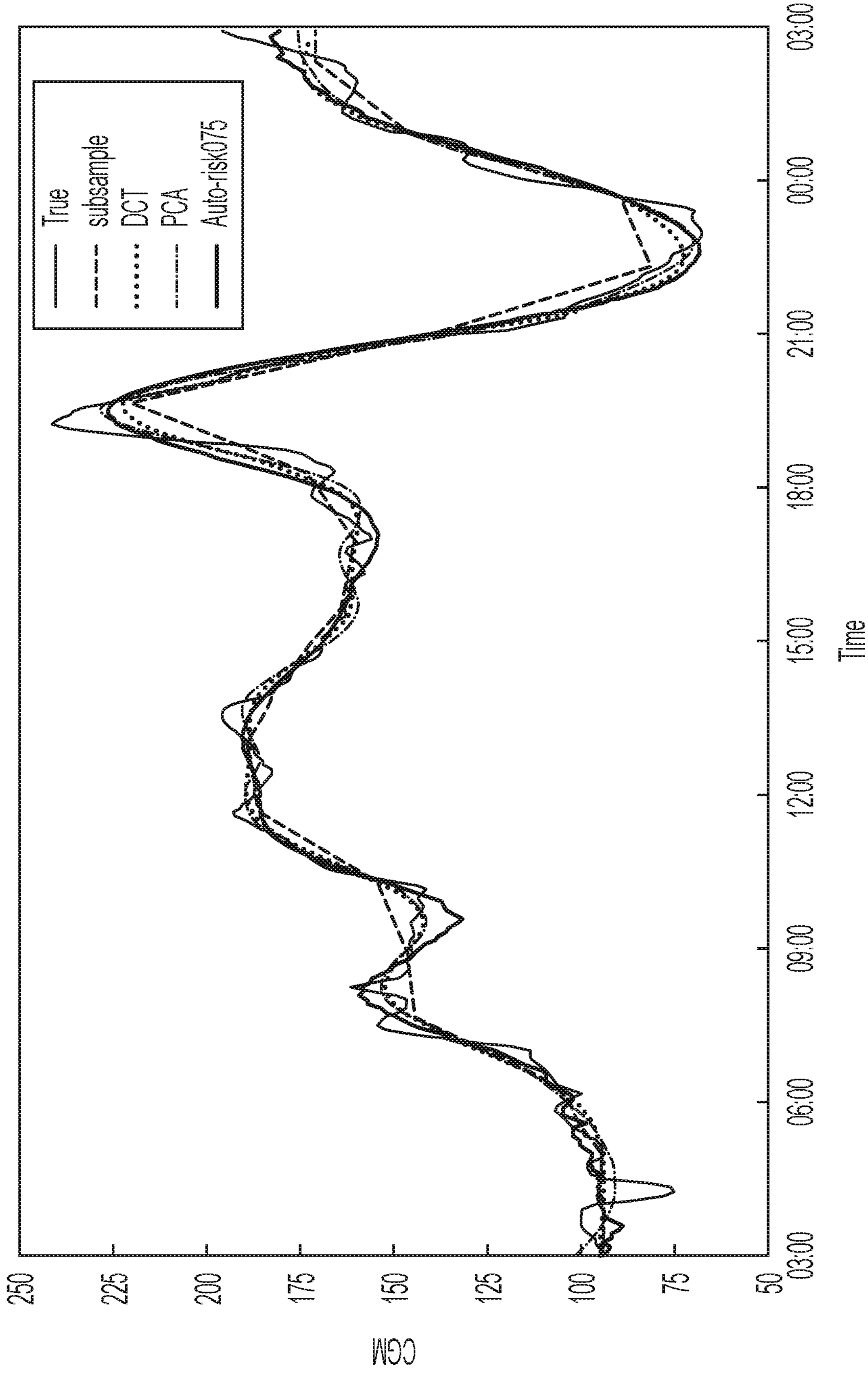
FIG. 11 graphically shows an example of reconstructing CGM data from the features learned with different algorithms.
Figure 12:
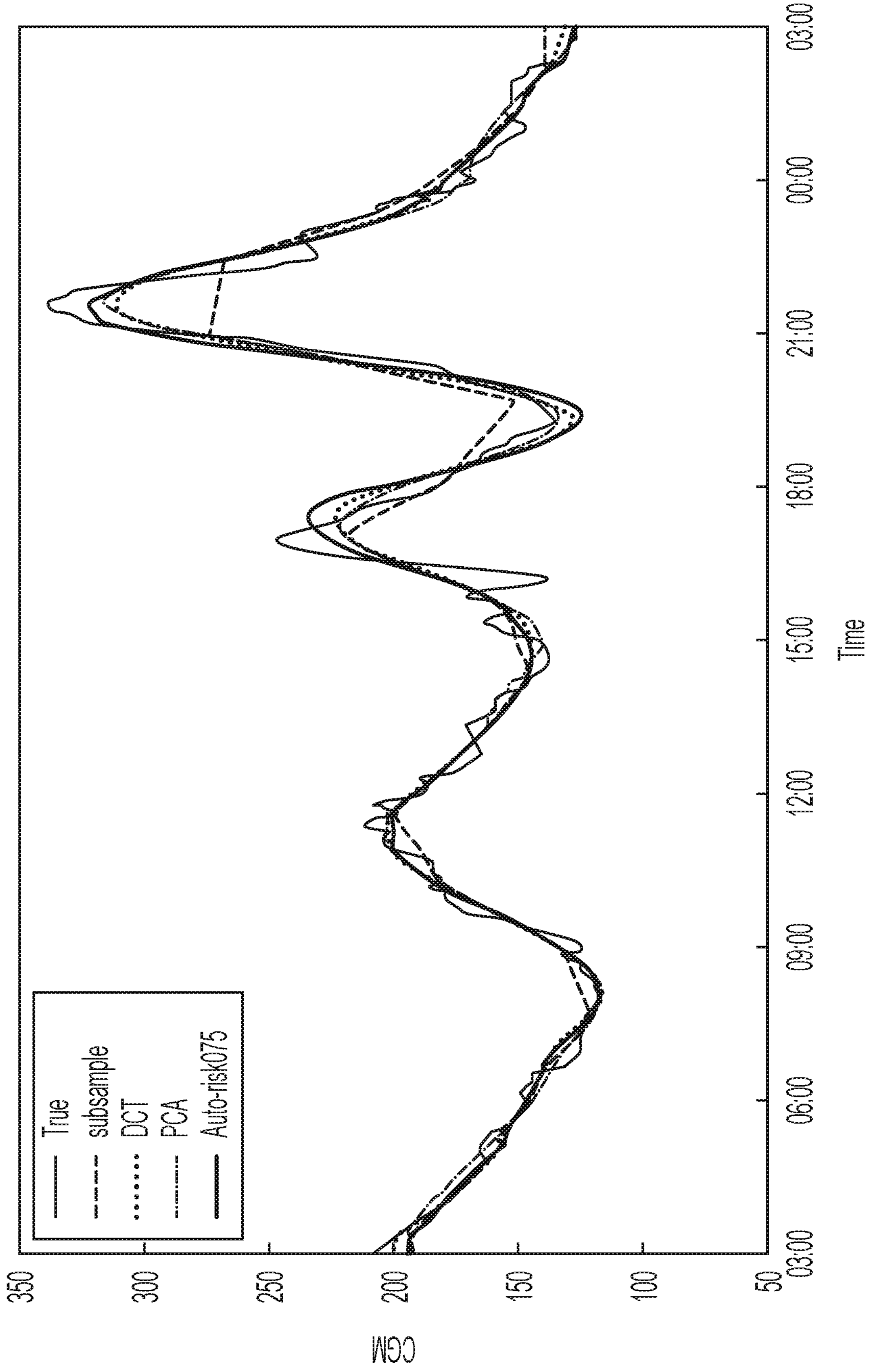
FIG. 12 graphically shows another example of reconstructing CGM data from the features learned with different algorithms.

Reconstruction Error. FIGS. 11 and 12 graphically show two typical examples (having both hyperglycemia and hypoglycemia regions) of reconstructing CGM from the features learned with different algorithms. FIG. 11 shows a comparison of reconstructed CGM data for Day #2500. FIG. 12 graphically shows a comparison of reconstructed CGM data for Day #3002.

Figure 13A:
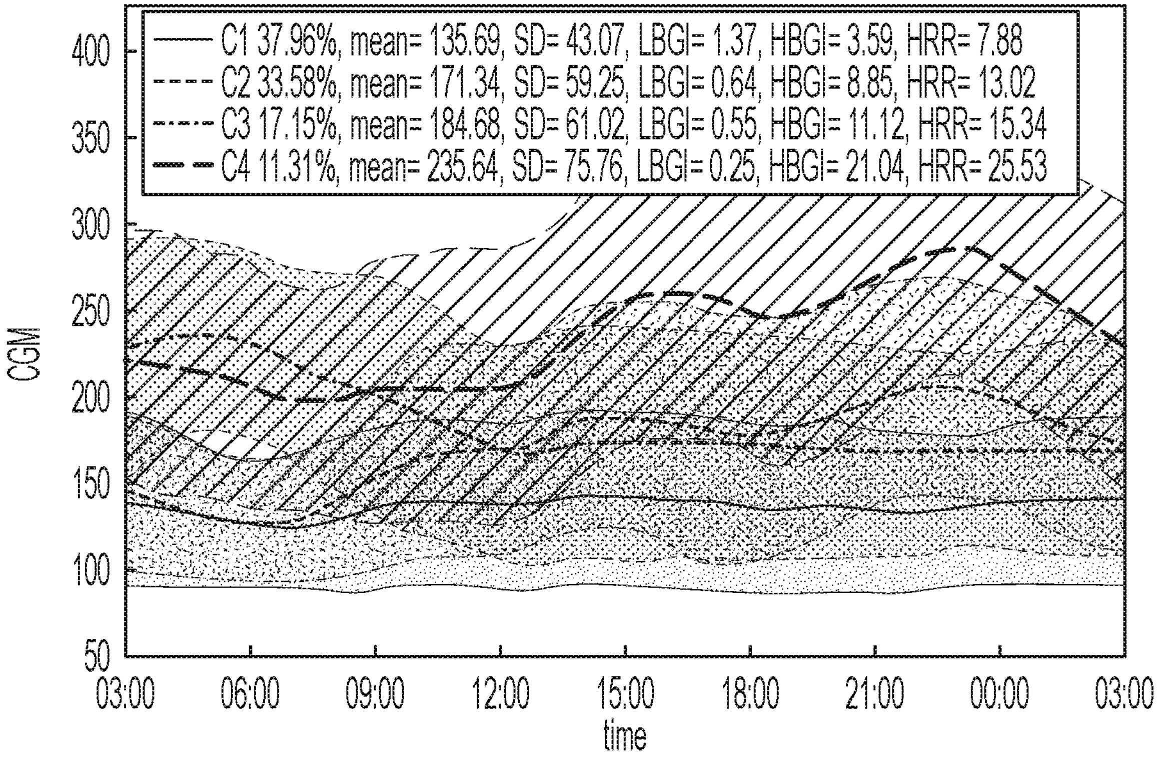
FIG. 13 graphically shows an envelop plot of clusters for the training dataset: non-data-driven methods.
Figure 13B:
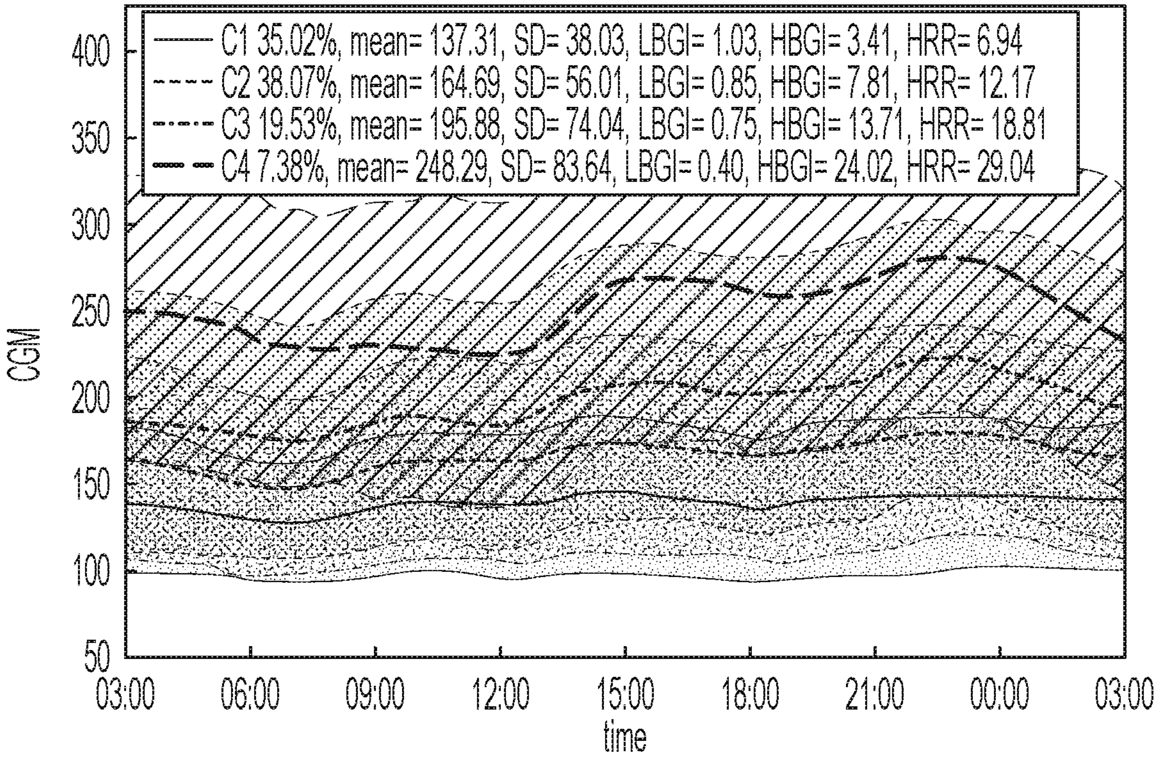
Figure 13C:
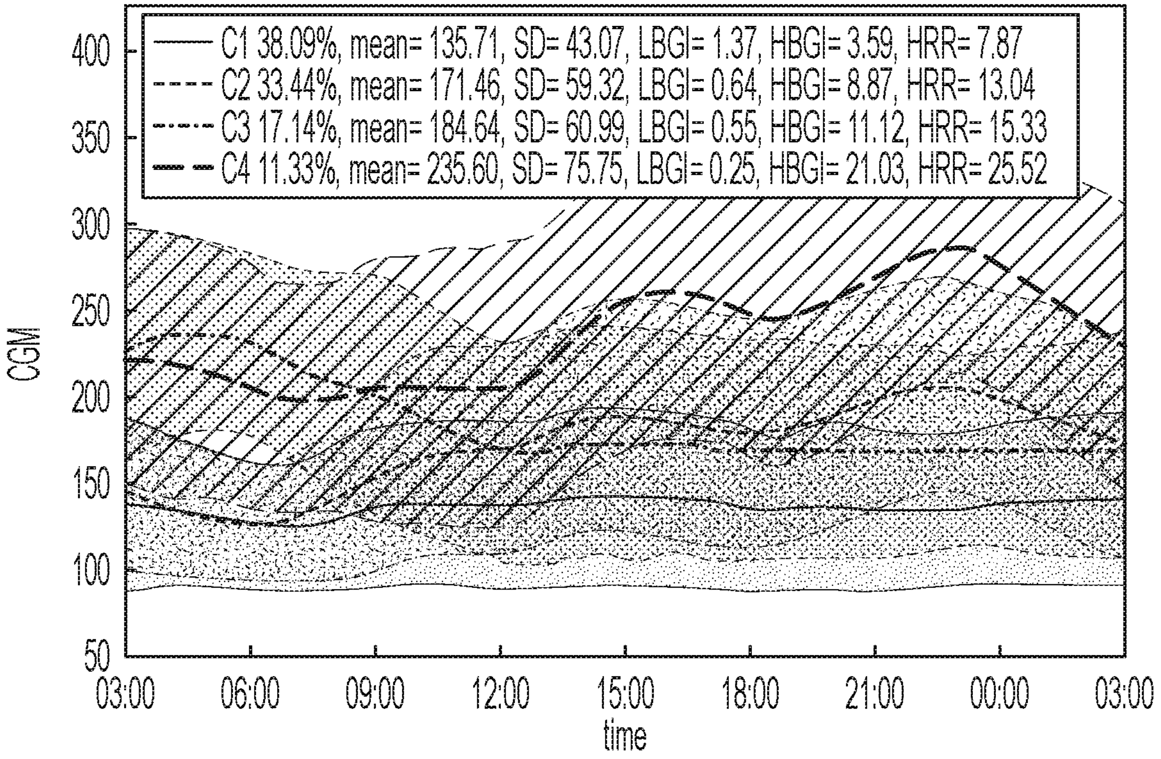
Figure 13D:
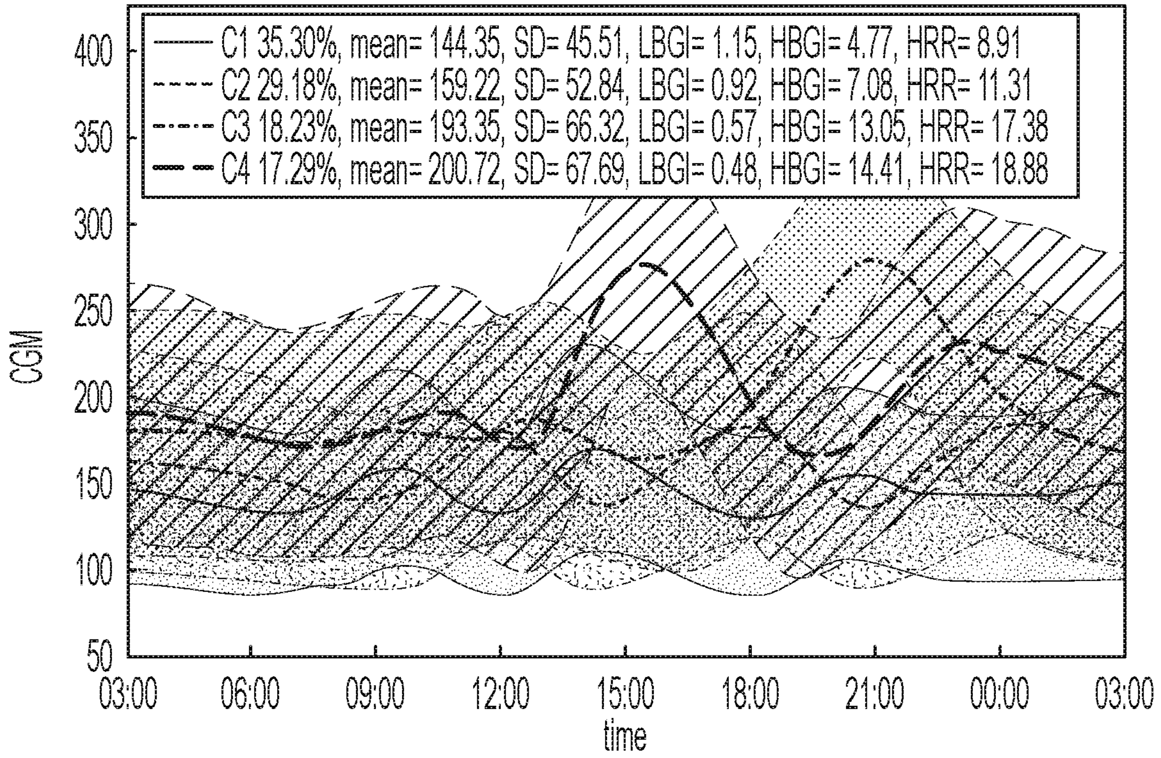
Figure 14A:
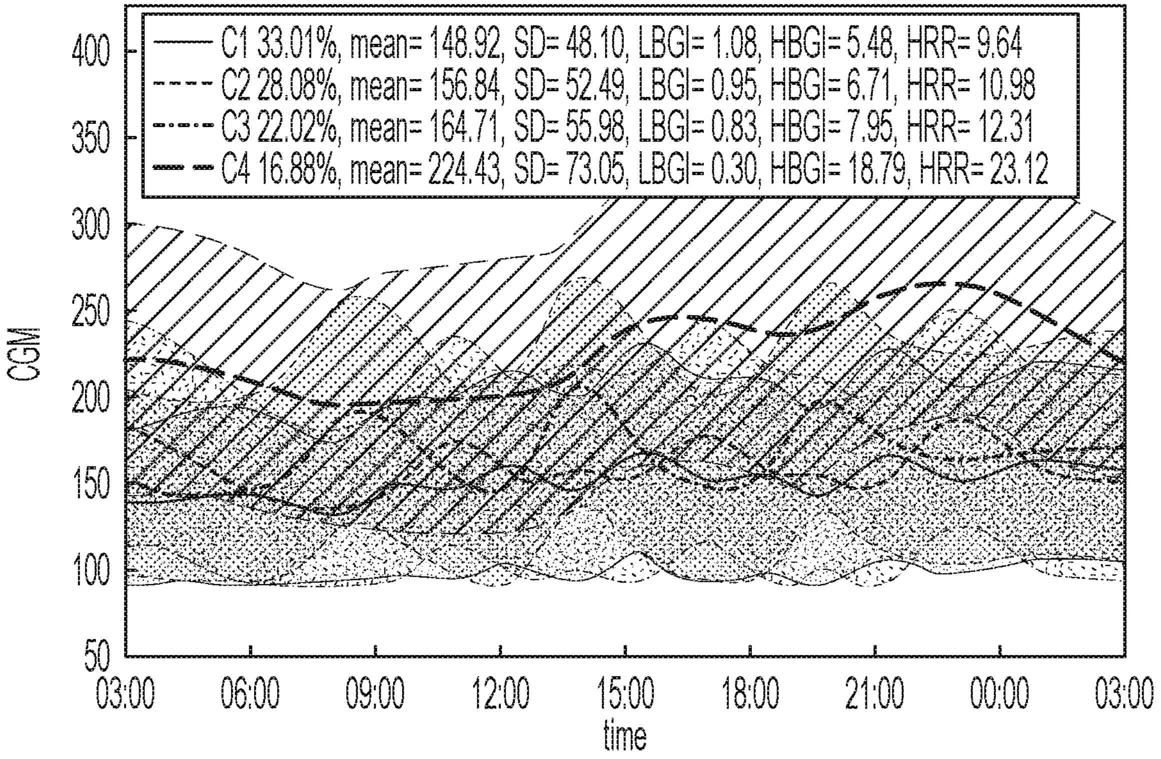
FIG. 14 graphically shows an envelop plot of clusters for the training dataset: data-driven methods.
Figure 14B:
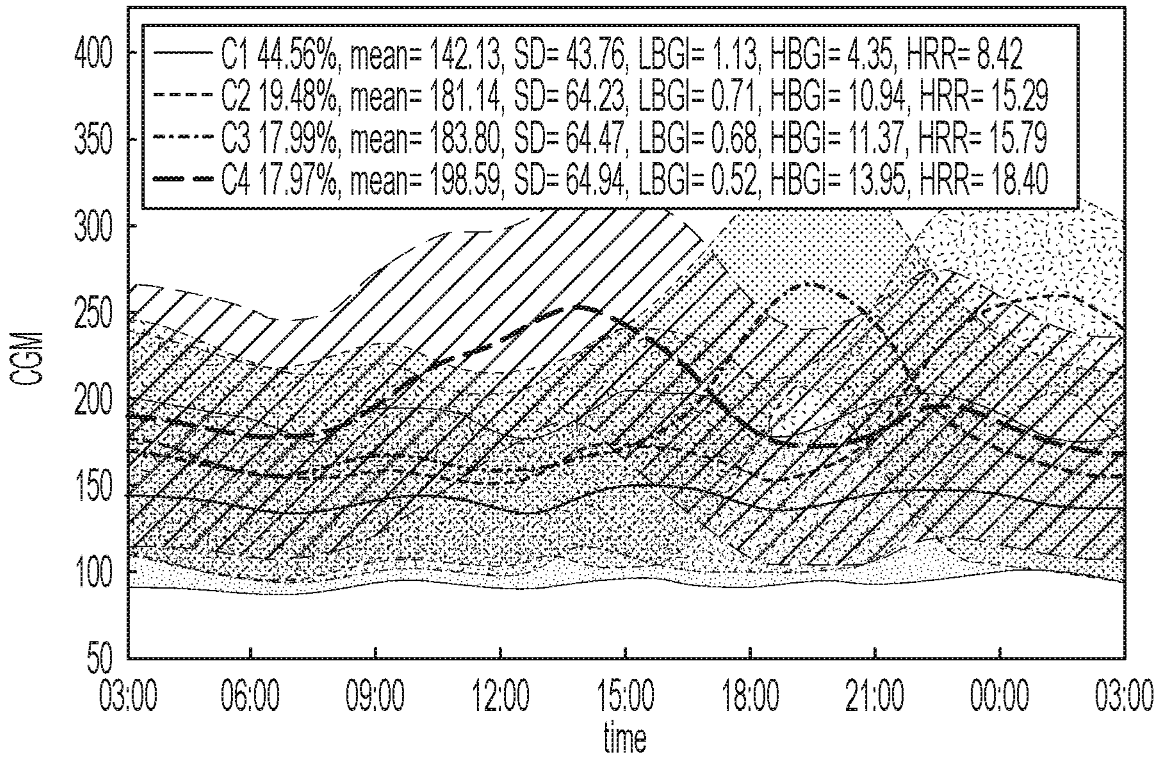
Figure 14C:
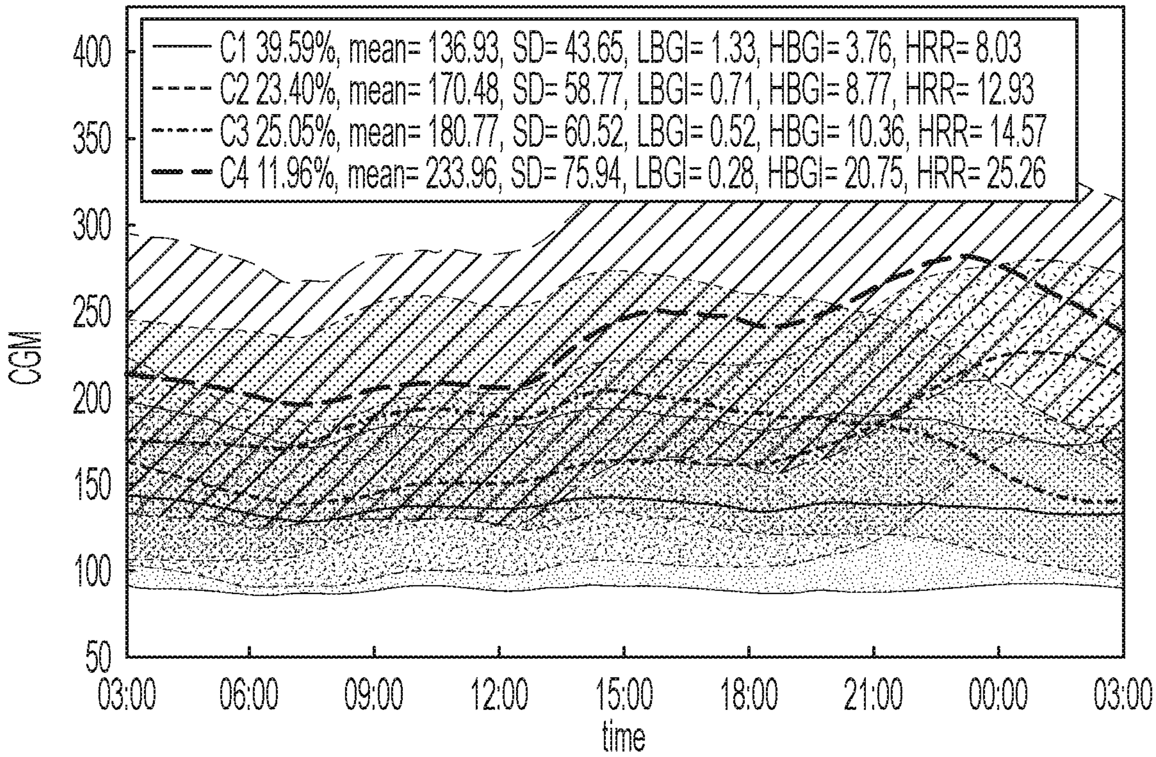
Figure 15A:
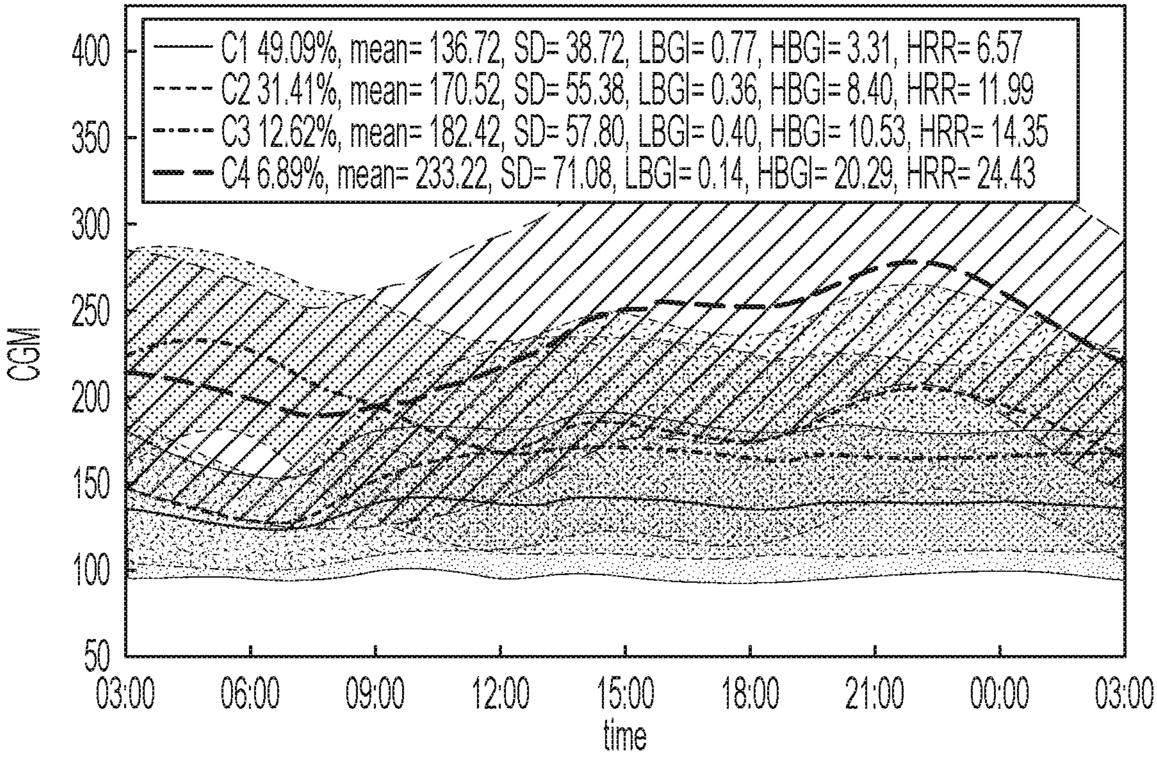
FIG. 15 graphically shows an envelop plot of clusters for the testing dataset: non-data-driven methods.
Figure 15B:
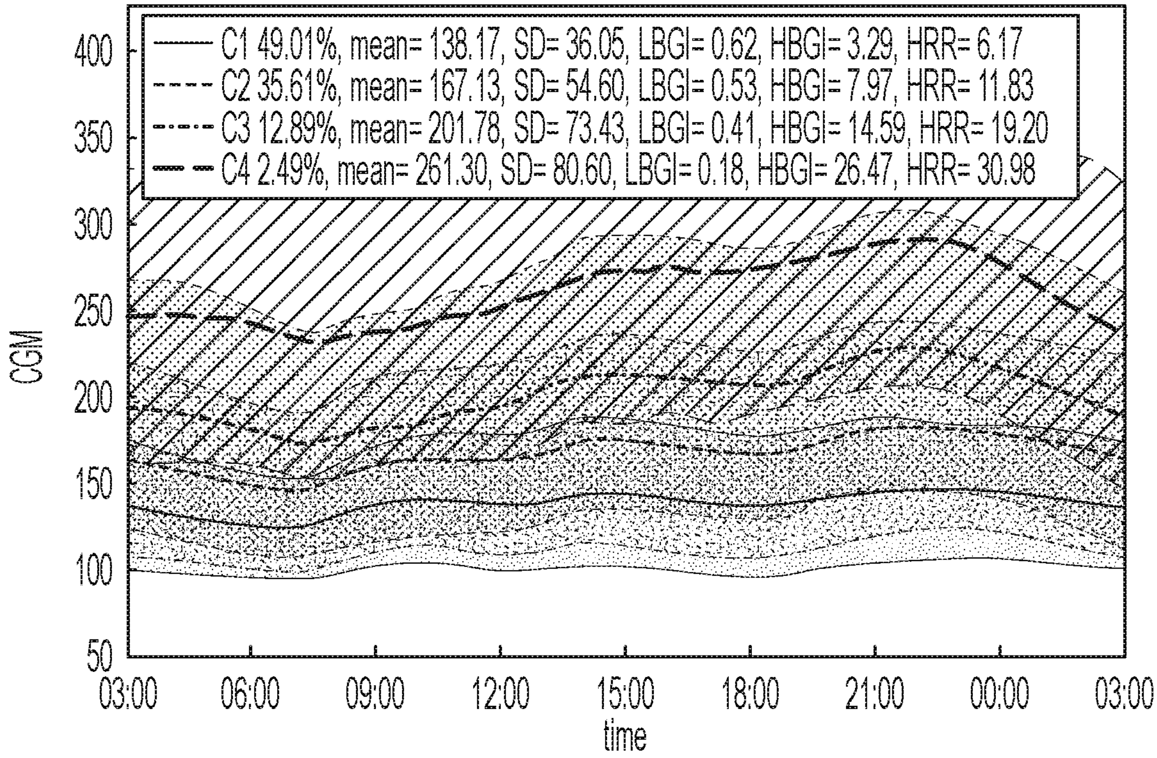
Figure 15C:
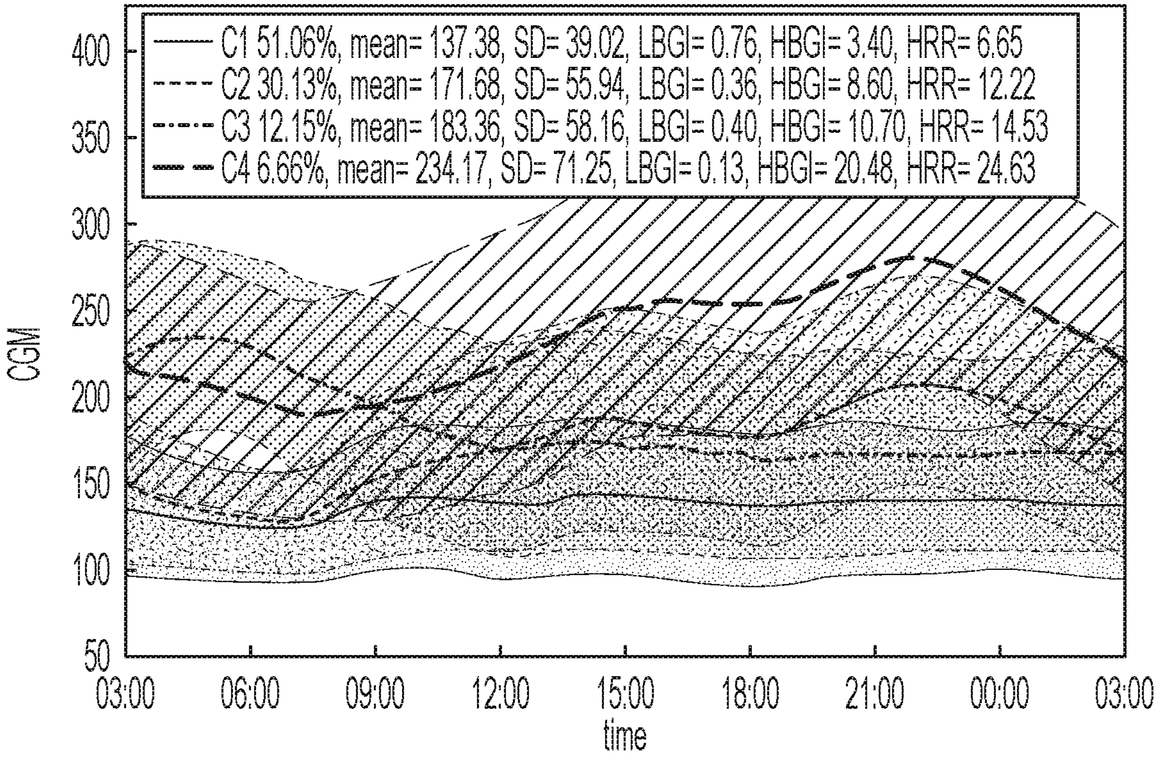
Figure 15D:
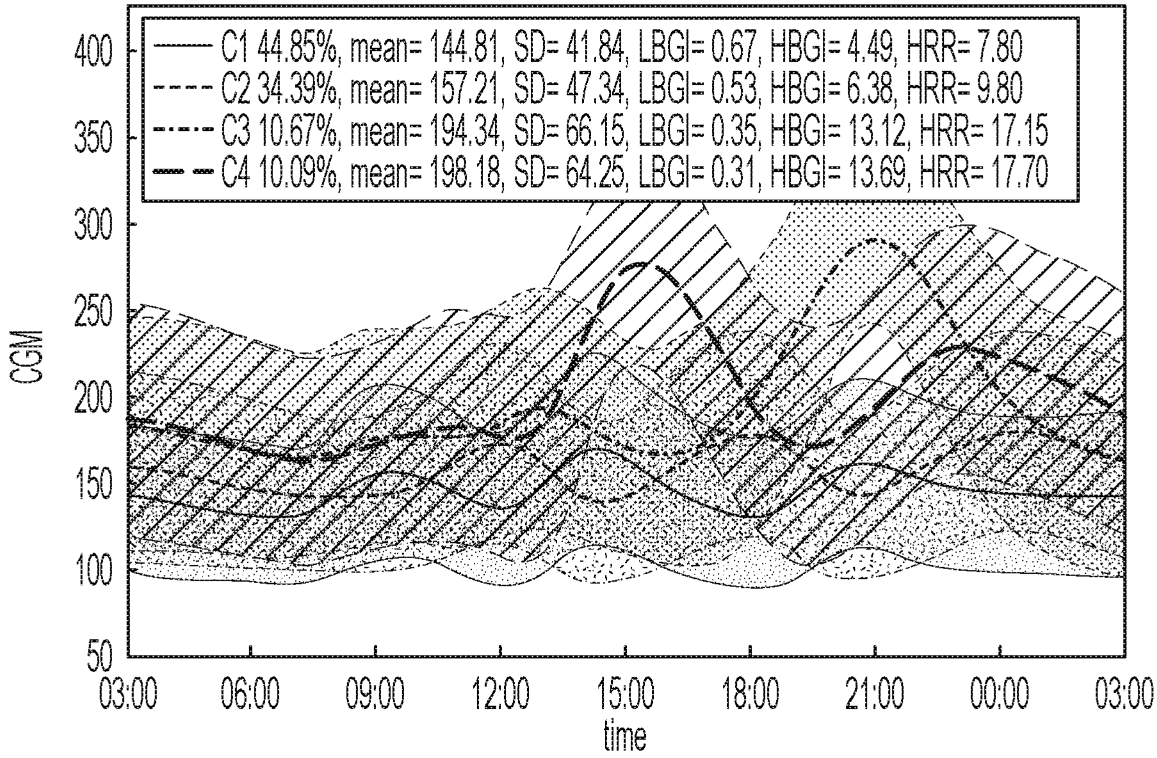
Figure 16A:
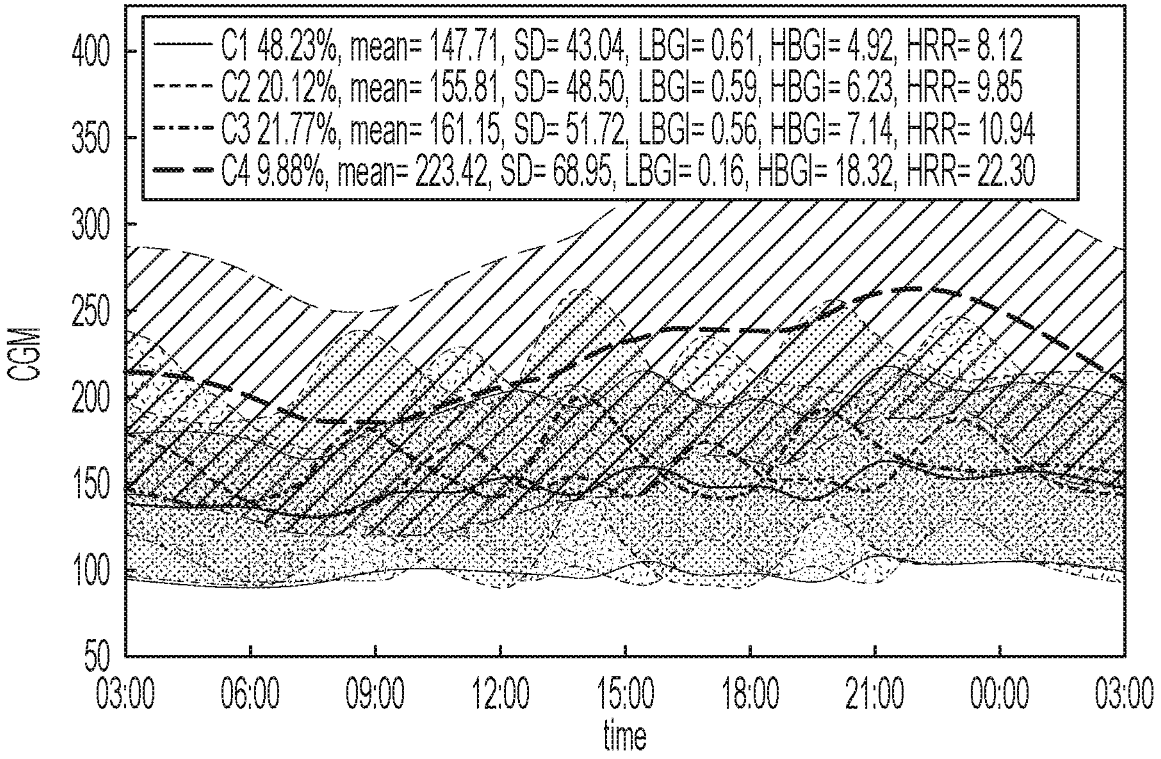
FIG. 16 graphically shows an envelop plot of clusters for the testing dataset: data-driven methods.
Figure 16B:
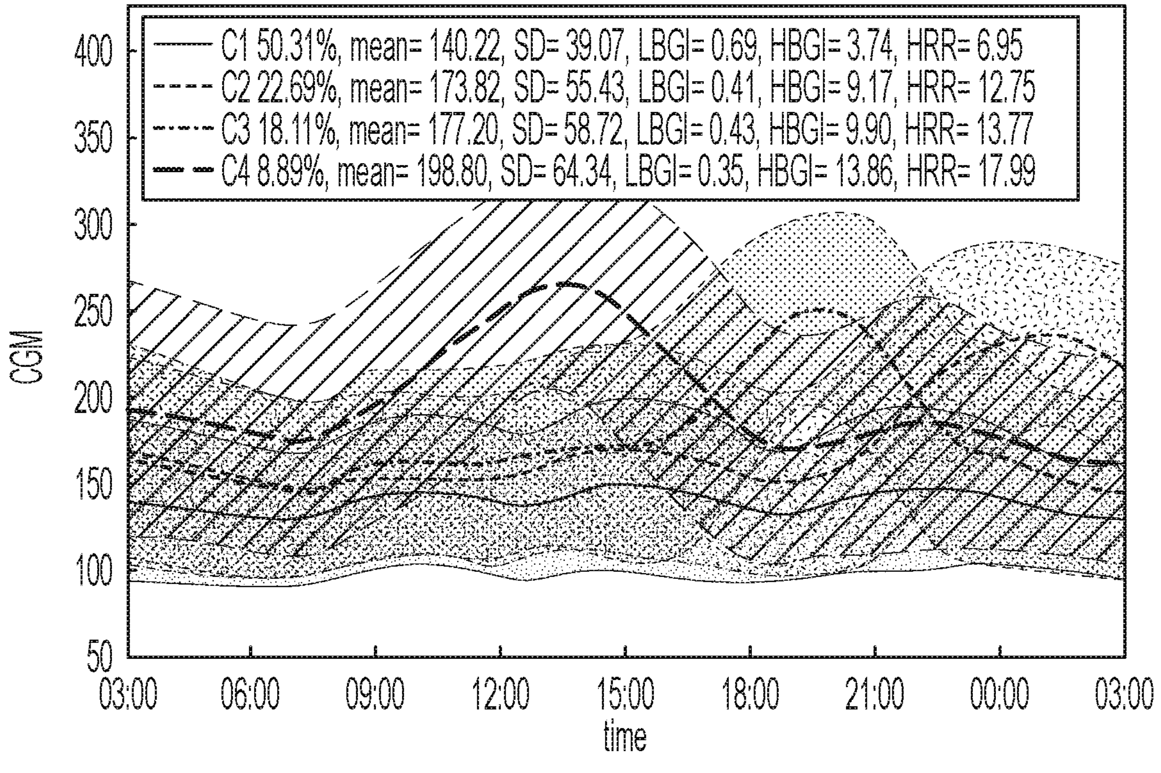
Figure 16C:
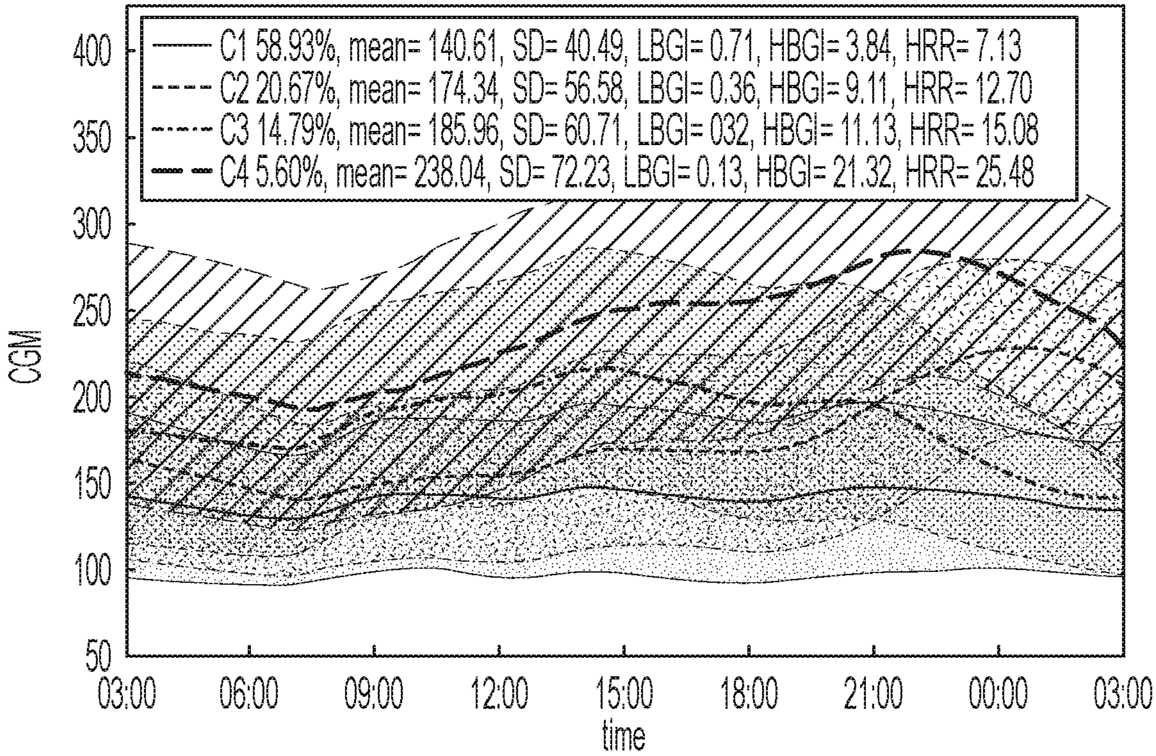
Figure 17A:
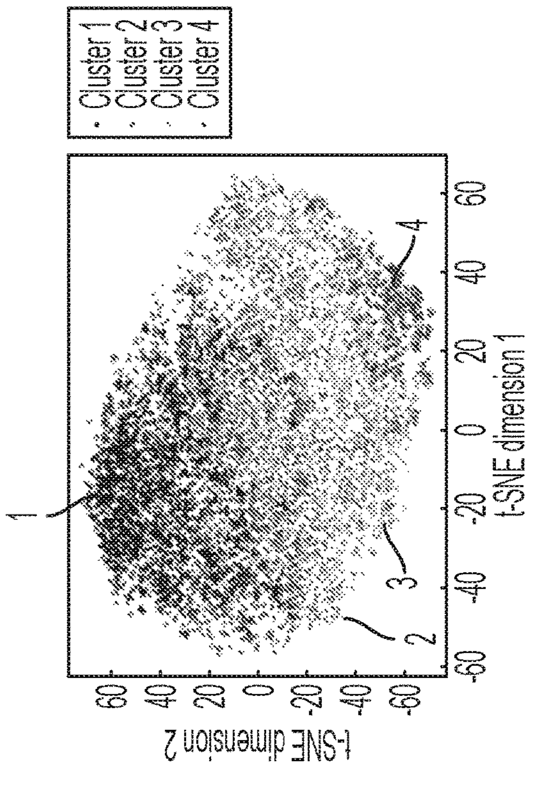
FIG. 17 graphically illustrates a t-SNE view of clusters for the training dataset: non-data-driven methods.
Figure 17B:
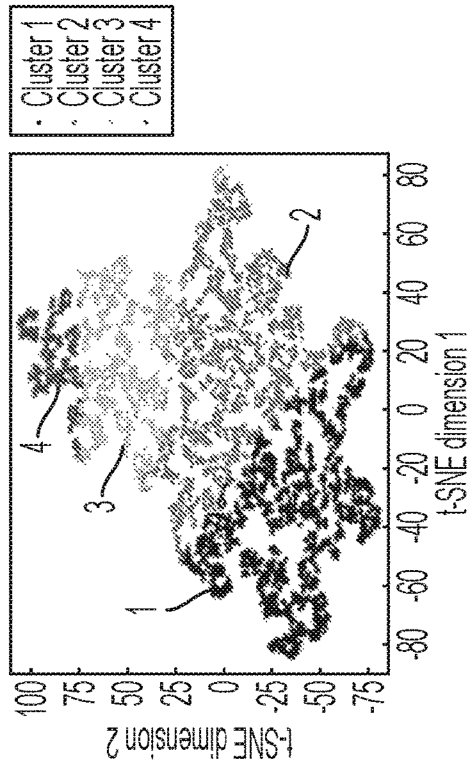
Figure 17C:
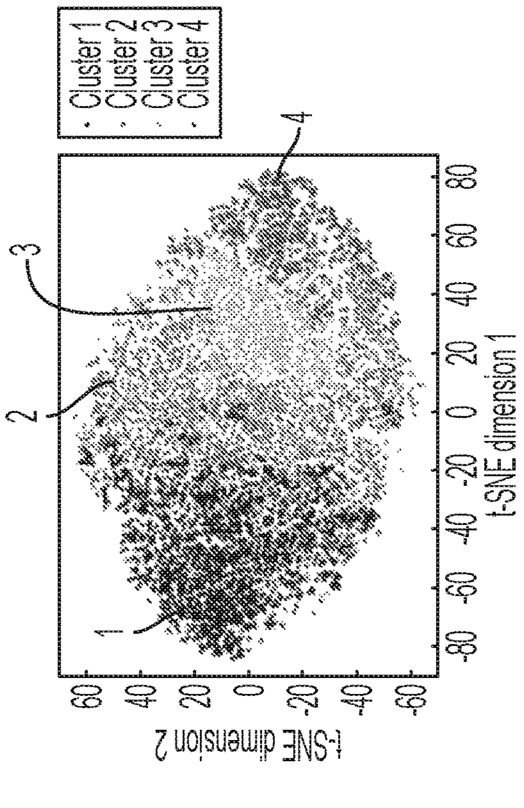
Figure 17D:
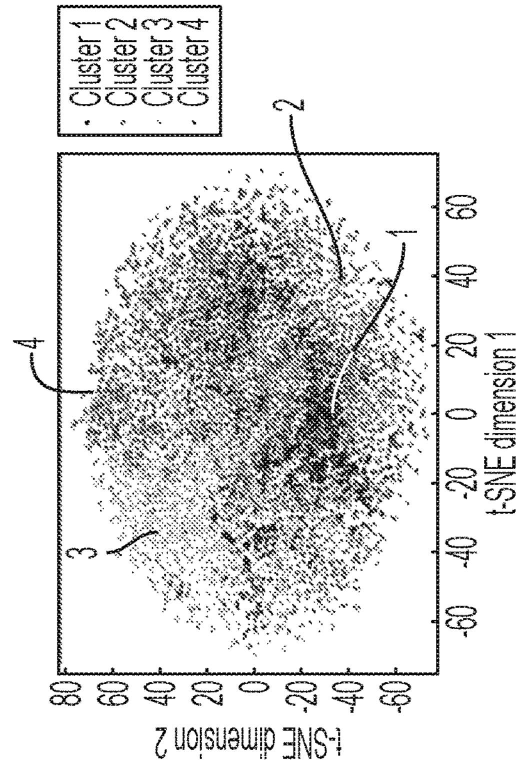
Figure 18B:
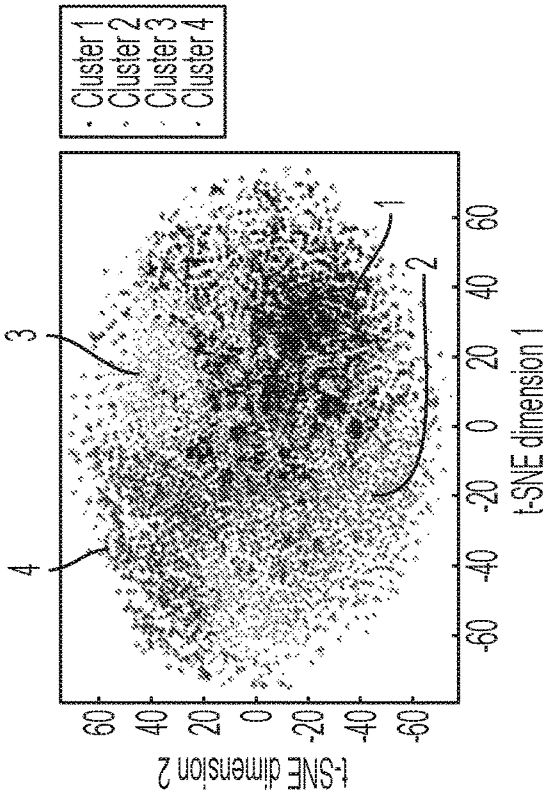
FIG. 18 graphically illustrates a t-SNE view of clusters for the training dataset: data-driven methods.
Figure 18A:
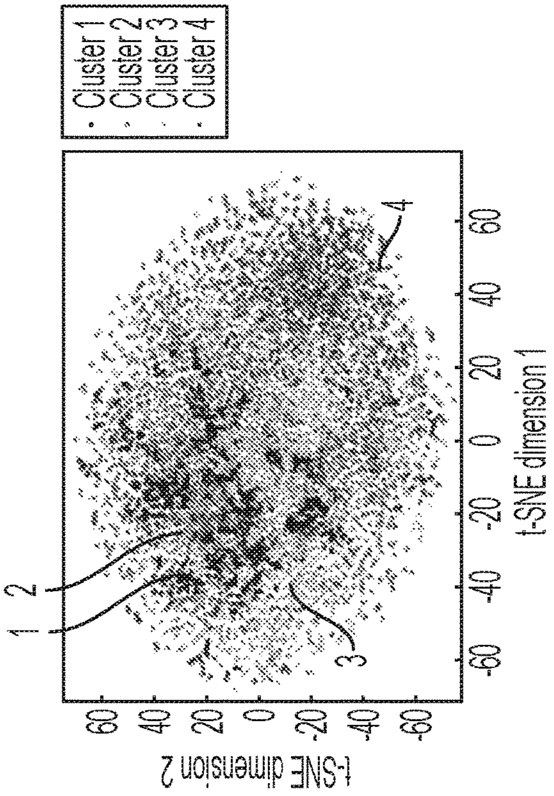
Figure 18C:
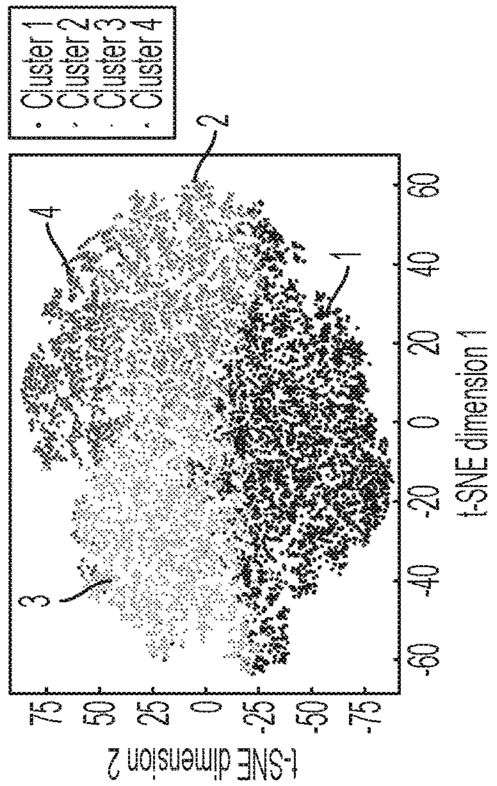
Figure 19B:
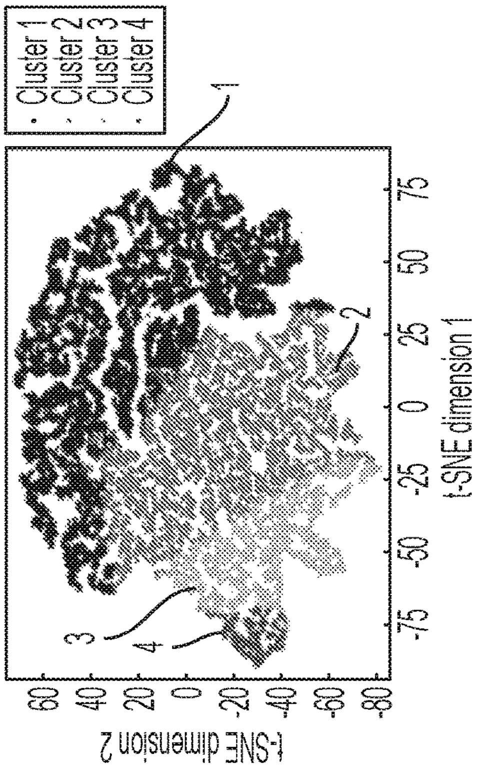
FIG. 19 graphically illustrates a t-SNE view of clusters for the testing dataset: non-data-driven methods.
Figure 19A:
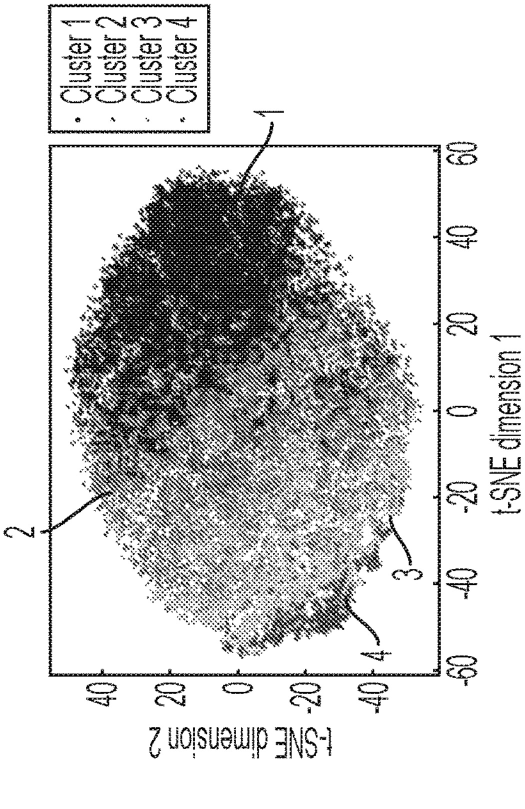
Figure 19D:
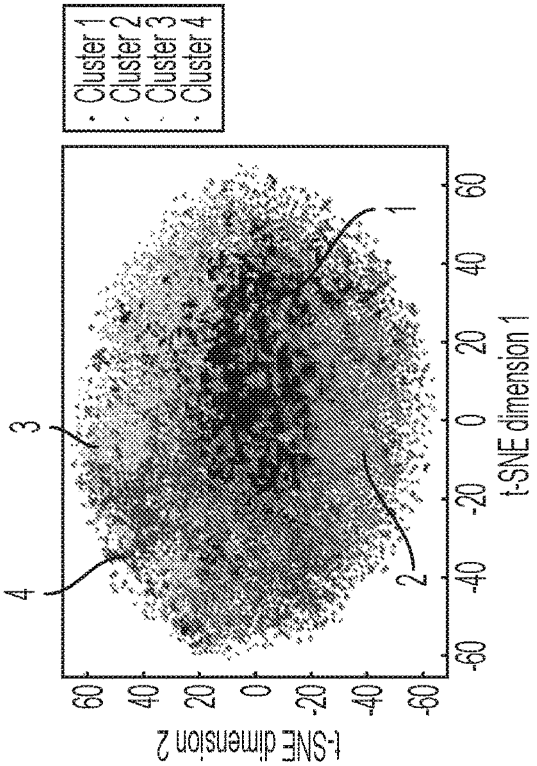
Figure 19C:
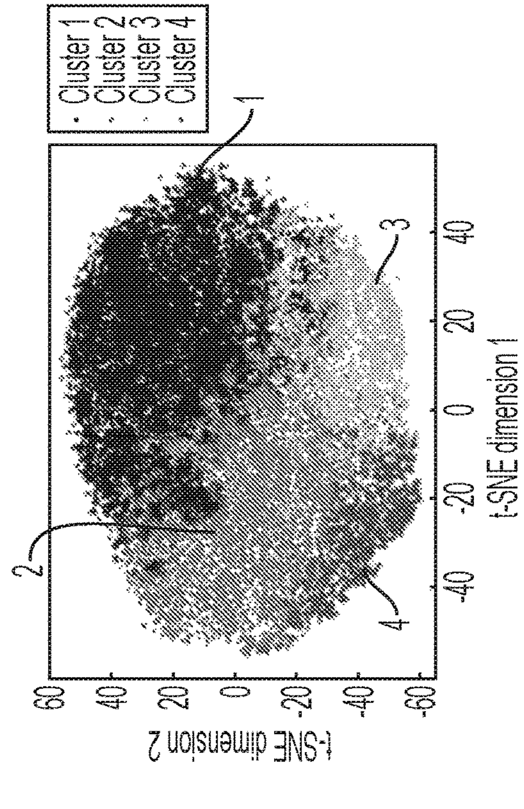
Figure 20B:
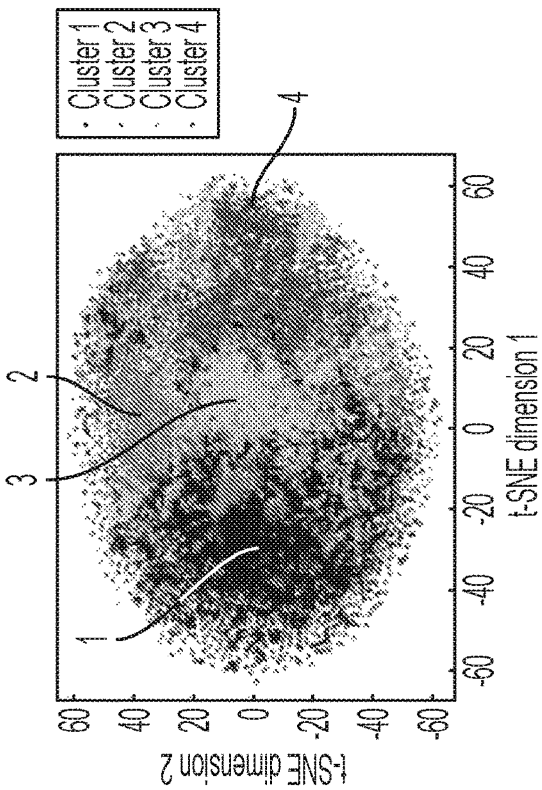
FIG. 20 graphically illustrates a t-SNE view of clusters for testing dataset: data-driven methods.
Figure 20A:
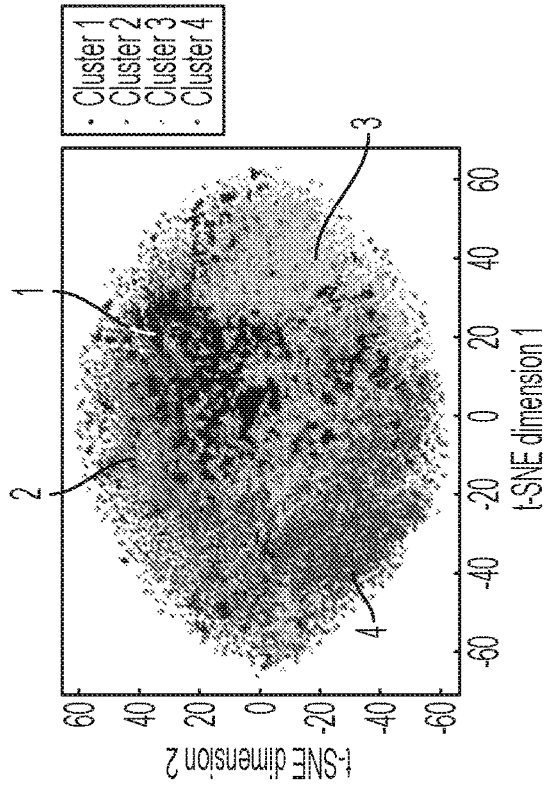
Figure 20C:
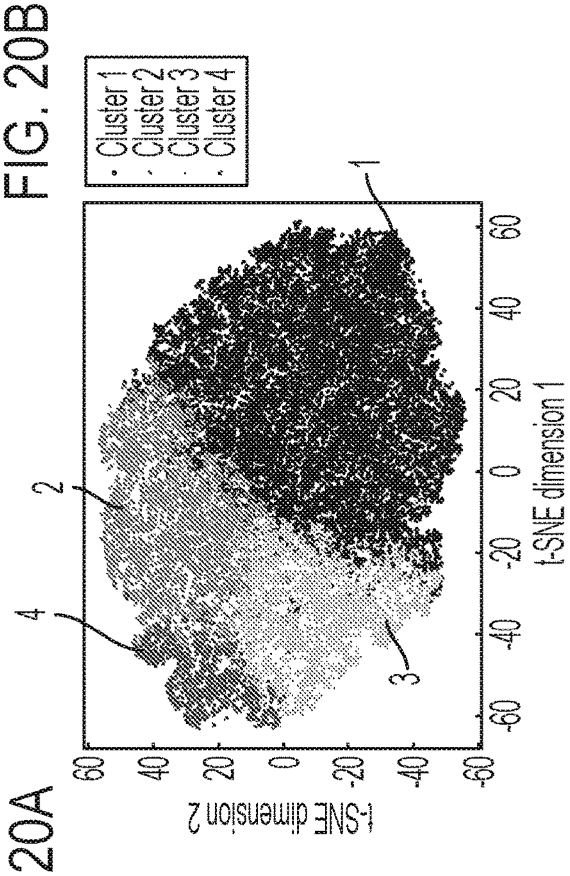
Figure 21:
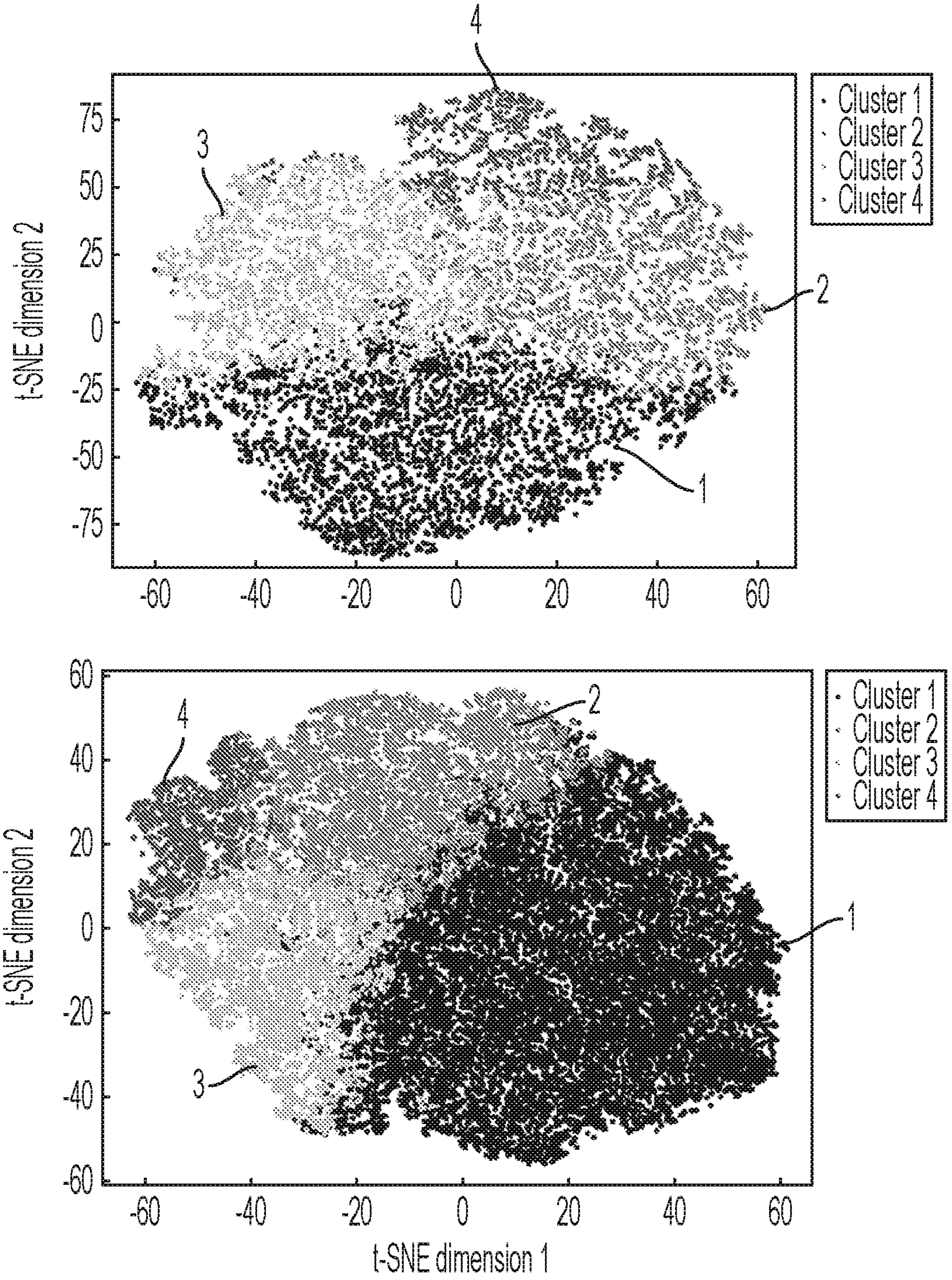
FIG. 21 graphically illustrates t-SNE clustering separation of iDCL-1 (top) and iDCL-3 (bottom).

Clustering and Visualization. In addition to the features obtained from subsampling, TDFA and autoencoder, we also consider the glycemic metrics as a feature set to carry out clustering. FIG. 13 graphically shows an envelop plot of clusters for the training dataset: non-data-driven methods. FIG. 13(A) represent raw CGM method. FIG. 13(B) represent Metrics method. FIG. 13(C) represent Subsampling method. FIG. 13(D) represent DCT method. FIG. 14 graphically shows an envelop plot of clusters for the training dataset: data-driven methods. FIG. 14(A) represent PCA method. FIG. 14(B) represent ICA method. FIG. 14(C) represent Auto-risk075 method. FIG. 15 graphically shows an envelop plot of clusters for the testing dataset: non-data-driven methods. FIG. 15(A) represent raw CGM method. FIG. 15(B) represent Metrics method. FIG. 15(C) represent Subsampling method. FIG. 15(D) represent DCT method. FIG. 16 graphically shows an envelop plot of clusters for the testing dataset: data-driven methods. FIG. 16(A) represent PCA method. FIG. 16(B) represent ICA method. FIG. 16(C) represent Auto-risk075 method. FIG. 17 graphically illustrates a t-SNE view of clusters for the training dataset: non-data-driven methods. FIG. 17(A) represent raw CGM method. FIG. 17(B) represent Metrics method. FIG. 17(C) represent Subsampling method. FIG. 17(D) represent DCT method. FIG. 18 graphically illustrates a t-SNE view of clusters for the training dataset: data-driven methods. FIG. 18(A) represent PCA method. FIG. 18(B) represent ICA method. FIG. 18(C) represent Auto-risk075 method. FIG. 19 graphically illustrates a t-SNE view of clusters for the testing dataset: non-data-driven methods. FIG. 19(A) represent raw CGM method. FIG. 19(B) represent Metrics method. FIG. 19(C) represent Subsampling method. FIG. 19(D) represent DCT method. FIG. 20 graphically illustrates a t-SNE view of clusters for testing dataset: data-driven methods. FIG. 20(A) represent PCA method. FIG. 20(B) represent ICA method. FIG. 20(C) represent Auto-risk075 method. FIG. 21 graphically illustrates t-SNE clustering separation of iDCL-1 (top) and iDCL-3 (bottom).

In conclusion, an aspect of an embodiment of the present invention provides, but is not limited thereto, feature-learning technique for temporal feature extraction trained on iDCL-1 and applied to iDCL-3 data classifies daily CGM profiles into four separable clusters which distinct CGM patterns between different times of the day, 3 am to noon vs. noon to 3 am. The classifier is sensitive to treatment and differentiates between control and experimental group.

Table I shows the root mean square error (RMSE) for each retrieval method for glycemic metrics, during the training of the autoencoder method. Table II shows the root mean square error (RMSE) for each retrieval method for glycemic metrics during the testing of the autoencoder method. Column 1 indicates the retrieval method, including conventional non-data-driven methods (subsampling, DCT), conventional data-driven methods (PCA, ICA), and variations on the claimed method of auto-encoding via a risk-weighted cost function (Auto-orig, Auto-risk050, Auto-risk075, Auto-risk100). Columns 2 and 3 indicate the mean and standard deviation (SD) of blood glucose, respectively. Columns 4 and 5 indicate the root mean square error (RMSE) of the low blood glucose index (LBGI) and high blood glucose index (HBGI) respectively. LBGI and HBGI are risk measures that describe overall daily risk without temporal data on the glucose profiles. Column 6 indicates the RMSE of hypoglycemia risk ratio (HRR) reconstruction for each retrieval method. Column 7 indicates the overall RMSE) for each glycemic metric retrieval method.

TABLE I

Comparison of root mean square error for retrieving metrics

| Method | mean | SD | LBGI | HBGI | HRR | CGM_RMSE |
|---|---|---|---|---|---|---|
| subsample | 0.020 | 54.098 | 0.376 | 0.269 | 7.552 | 14.682 |
| DCT | 0.015 | 2.589 | 0.056 | 0.015 | 1.887 | 10.897 |
| PCA | 0.016 | 2.095 | 0.052 | 0.012 | 1.711 | 10.353 |
| ICA | 0.016 | 2.095 | 0.052 | 0.012 | 1.711 | 10.353 |
| Auto-orig | 6.298 | 6.515 | 0.104 | 0.272 | 3.714 | 12.564 |
| Auto-risk050 | 2.881 | 2.350 | 0.089 | 0.067 | 1.265 | 12.581 |
| Auto-risk075 | 0.537 | 2.133 | 0.092 | 0.020 | 1.147 | 11.338 |
| Auto-risk100 | 6.770 | 3.619 | 0.115 | 0.133 | 0.707 | 12.909 |
| Dataset Average* | 167.368 | 55.278 | 0.858 | 8.620 | 12.879 | 0.000 |

*This row shows the average amplitude of the each metric across the whole dataset.

TABLE II

Comparison of root mean square error for retrieving metrics

| Method | mean | SD | LBGI | HBGI | HRR | CGM_RMSE |
|---|---|---|---|---|---|---|
| subsample | 0.015 | 50.571 | 0.205 | 0.238 | 5.917 | 14.244 |
| DCT | 0.006 | 3.508 | 0.041 | 0.018 | 1.781 | 11.042 |
| PCA | 0.007 | 2.858 | 0.038 | 0.015 | 1.603 | 10.518 |
| ICA | 0.007 | 2.858 | 0.038 | 0.015 | 1.603 | 10.518 |
| Auto-orig | 5.716 | 7.248 | 0.060 | 0.235 | 3.222 | 12.487 |
| Auto-risk050 | 2.988 | 2.517 | 0.059 | 0.056 | 1.136 | 12.536 |
| Auto-risk075 | 0.509 | 2.423 | 0.057 | 0.016 | 1.092 | 11.409 |
| Auto-risk100 | 7.668 | 3.275 | 0.066 | 0.122 | 0.652 | 12.900 |
| Dataset Average* | 159.748 | 48.587 | 0.551 | 6.989 | 10.484 | 0.000 |

*This row shows the average amplitude of the each metric across the whole dataset.

Additional Examples

Example 1. A computer-implemented method for compressing continuous glucose monitor (CGM) data of a subject, comprising:

receiving CGM data profiles of said subject;

extracting glycemic risk profiles from the CGM data profiles;

compressing the CGM data profiles into low-dimensional representations using a trained neural network encoder via a cost function weighted by said extracted glycemic risk profiles;

transmitting said low-dimensional representations of CGM profiles to a secondary source, or reconstructing said low-dimensional representations of CGM profiles to full-dimensional CGM profiles via a trained neural network decoder and transmitting said reconstructed full-dimensional CGM profiles via said trained neural network decoder to a secondary source; and wherein:

said transmitted low-dimensional representations of CGM profiles, which optionally are configured to be reconstructed to full-dimensional CGM profiles, are configured to allow:

a) said subject, a technician, or a clinician to take a physical action in response to receiving said transmission to improve the safety and/or efficacy of therapy for said subject, or b) an interventional device to operationally take action in response to receiving said transmission to improve the safety and/or efficacy of therapy for said subject; or said transmitted reconstructed full-dimensional CGM profiles are configured to allow:

a) said subject, a technician, or a clinician to take a physical action in response to receiving said transmission to improve the safety and/or efficacy of therapy for said subject, or b) an interventional device to operationally take action in response to receiving said transmission to improve the safety and/or efficacy of therapy for said subject.

Example 2. The method of example 1, wherein said interventional device includes one or more of anyone of the following:

insulin pump device;

decision support system;

low glucose suspend system;

connected insulin pens;

automated insulin delivery systems; or intelligent patch or intelligent transplant.

Example 3. The method of example 1 (as well as subject matter in whole or in part of example 2), wherein said secondary source includes one or more of anyone of the following:

local memory;

remote memory; or display or graphical user interface.

Example 4. The method of example 1 (as well as subject matter of one or more of any combination of examples 2-3, in whole or in part), wherein said improvement of the safety and/or efficacy of therapy for said subject may include one or more of the following:

preventing a hypoglycemic event(s) from occurring in said subject;

preventing a hyperglycemic event(s) from occurring in said subject;

reducing excessive glucose variability occurring in said subject;

reducing postprandial glucose excursions occurring in said subject;

reducing the risk for hypoglycemia;

reducing the risk for hyperglycemia;

optimizing delivery of antidiabetic drugs/compounds (including, insulin); or lowering glycated hemoglobin (HbA1c).

Example 5. The method of example 1 (as well as subject matter of one or more of any combination of examples 2-4, in whole or in part), wherein the neural network of the neural network encoder and the neural network of the neural network decoder includes one of the following:

artificial neural network (ANN);

convolutional neural network (CNN); or recurrent neural networks (RNN).

Example 6. The method of example 5, wherein the CNN is an autoencoder.

Example 7. The method of example 1 (as well as subject matter of one or more of any combination of examples 2-6, in whole or in part), wherein the cost function includes one or more of anyone of the following:

maximum likelihood cost function;

absolute deviation cost function; or mean squared error cost function.

Example 8. The method of example 7, wherein said mean squared error cost function is represented by the following formula:

$$\sum_{i=1}^{n} w_i^{[0,1]}\left(Y_i - \hat{Y}_i\right)^2$$

wherein:

$Y_i$=observed result, for any i=1, 2, . . . , n $\hat{Y}_i$=predicted result, for any i=1, 2, . . . , n $w_i$=the weight of the $i^{th}$ glycemic risk profile, such that $0 \le w_i \le 1$, for any i=1, 2, . . . , n n=number of profiles.

whereby:

the mean squared cost function is weighted by the corresponding glycemic risk profile or a function of the corresponding glycemic risk profile.

Example 9. The method of example 8, wherein the sum of weights equals 1, wherein $$\sum_{i=1}^{n} w_i = 1.$$

Example 10. The method of example 1 (as well as subject matter of one or more of any combination of examples 2-9, in whole or in part), further comprising, prior to the extraction, preprocessing the received CGM data profiles.

Example 11. The method of example 10, wherein the preprocessing comprises discarding a specified percentage of incomplete CGM data profiles.

Example 12. The method of example 11, wherein the specified percentage of incomplete CGM data profiles includes one of the following:

range of 0 percent and less than about 50 percent;

range of 0 percent and less than about 40 percent;

range of 0 percent and less than about 30 percent;

range of 0 percent and less than about 20 percent;

range of 0 percent and less than about 10 percent; or about 10 percent.

Example 13. A system configured for compressing continuous glucose monitor (CGM) data of a subject, comprising:

a computer processor;

a memory configured to store instructions that are executable by the computer processor, wherein said processor is configured to execute the instructions to:

receive CGM data profiles of said subject;

extract glycemic risk profiles from the CGM data profiles;

compress the CGM data profiles into low-dimensional representations using a trained neural network encoder via a cost function weighted by said extracted corresponding glycemic risk profiles;

transmit said low-dimensional representations of CGM profiles to a secondary source, or reconstruct said low-dimensional representations of CGM profiles to full-dimensional CGM profiles via a trained neural network decoder and transmit said reconstructed full-dimensional CGM profiles via said trained neural network decoder to a secondary source; and wherein:

said transmitted low-dimensional representations of CGM profiles, which optionally are configured to be reconstructed to full-dimensional CGM profiles, are configured to allow:

a) said subject, a technician, or a clinician to take a physical action in response to receiving said transmission to improve the safety and/or efficacy of therapy for said subject, or b) an interventional device to operationally take action in response to receiving said transmission to improve the safety and/or efficacy of therapy for said subject; or said transmitted reconstructed full-dimensional CGM profiles are configured to allow:

a) said subject, a technician, or a clinician to take a physical action in response to receiving said transmission to improve the safety and/or efficacy of therapy for said subject, or b) an interventional device to operationally take action in response to receiving said transmission to improve the safety and/or efficacy of therapy for said subject.

Example 14. The system of example 13, wherein said interventional device includes one or more of anyone of the following:

insulin pump device;

decision support system;

low glucose suspend system;

connected insulin pens;

automated insulin delivery systems; or intelligent patch or intelligent transplant.

Example 15. The system of example 13 (as well as subject matter in whole or in part of example 14), wherein said secondary source includes one or more of anyone of the following:

local memory;

remote memory; or display or graphical user interface.

Example 16. The system of example 13 (as well as subject matter of one or more of any combination of examples 14-15, in whole or in part), wherein said improvement of the safety and/or efficacy of therapy for said subject may include one or more of the following:

preventing a hypoglycemic event(s) from occurring in said subject;

preventing a hyperglycemic event(s) from occurring in said subject;

reducing excessive glucose variability occurring in said subject;

reducing postprandial glucose excursions occurring in said subject;

reducing the risk for hypoglycemia;

reducing the risk for hyperglycemia;

optimizing delivery of antidiabetic drugs/compounds (including, insulin); or lowering glycated hemoglobin (HbA1c).

Example 17. The system of example 13 (as well as subject matter of one or more of any combination of examples 14-16, in whole or in part), wherein the neural network of the neural network encoder and the neural network of the neural network decoder includes one of the following:

artificial neural network (ANN);

convolutional neural network (CNN); or recurrent neural networks (RNN).

Example 18. The system of example 17, wherein the CNN is an autoencoder.

Example 19. The system of example 13 (as well as subject matter of one or more of any combination of examples 14-18, in whole or in part), wherein the cost function includes one or more of anyone of the following:

maximum likelihood cost function;

absolute deviation cost function; or mean squared error cost function.

Example 20. The system of example 19, wherein said mean squared error cost function is represented by the following formula:

$$\sum_{i=1}^{n} w_i^{[0,1]}\left(Y_i - \hat{Y}_i\right)^2$$

wherein:

$Y_i$=observed result, for any i=1, 2, . . . , n $\hat{Y}_i$=predicted result, for any i=1, 2, . . . , n $w_i$=the weight of the $i^{th}$ glycemic risk profile, such that $0 \leq w_i \leq 1$, for any i=1, 2, . . . , n n=number of profiles.

whereby:

the mean squared cost function is weighted by the corresponding glycemic risk profile or a function of the corresponding glycemic risk profile.

Example 21. The system of example 20, wherein the sum of weights equals 1, wherein $$\sum_{i=1}^{n} w_i = 1.$$

Example 22. The system of example 13 (as well as subject matter of one or more of any combination of examples 14-21, in whole or in part), further comprising, prior to the extraction, preprocessing the received CGM data profiles.

Example 23. The system of example 22, wherein the preprocessing comprises discarding a specified percentage of incomplete CGM data profiles.

Example 24. The system of example 23, wherein the specified percentage of incomplete CGM data profiles includes one of the following:

range of 0 percent and less than about 50 percent;

range of 0 percent and less than about 40 percent;

range of 0 percent and less than about 30 percent;

range of 0 percent and less than about 20 percent;

range of 0 percent and less than about 10 percent; or about 10 percent.

Example 25. A computer program product, comprising a non-transitory computer-readable storage medium containing computer-executable instructions for compressing continuous glucose monitor (CGM) data of a subject, said instructions causing the computer to:

receive CGM data profiles of said subject;

extract glycemic risk profiles from the CGM data profiles;

compress the CGM data profiles into low-dimensional representations using a trained neural network encoder via a cost function weighted by said glycemic risk profiles;

transmit said low-dimensional representations of CGM profiles to a secondary source or reconstruct said low-dimensional representations of CGM profiles to full-dimensional CGM profiles via a trained neural network decoder and transmit said reconstructed full-dimensional CGM profiles via said trained neural network decoder to a secondary source; and wherein:

said transmitted low-dimensional representations of CGM profiles, which optionally are configured to be reconstructed to full-dimensional CGM profiles, are configured to allow:

a) said subject, a technician, or a clinician to take a physical action in response to receiving said transmission to improve the safety and/or efficacy of therapy for said subject, or b) an interventional device to operationally take action in response to receiving said transmission to improve the safety and/or efficacy of therapy for said subject; or said transmitted reconstructed full-dimensional CGM profiles are configured to allow:

a) said subject, a technician, or a clinician to take a physical action in response to receiving said transmission to improve the safety and/or efficacy of therapy for said subject, or b) an interventional device to operationally take action in response to receiving said transmission to improve the safety and/or efficacy of therapy for said subject.

Example 26. The computer program product of example 25, wherein said interventional device includes one or more of anyone of the following:

insulin pump device;

decision support system;

low glucose suspend system;

connected insulin pens;

automated insulin delivery systems; or intelligent patch or intelligent transplant.

Example 27. The computer program product of example 25 (as well as subject matter in whole or in part of example 26), wherein said secondary source includes one or more of anyone of the following:

- local memory;
- remote memory; or
- display or graphical user interface.

Example 28. The computer program product of example 25 (as well as subject matter of one or more of any combination of examples 26-27, in whole or in part), wherein said improvement of the safety and/or efficacy of therapy for said subject may include one or more of the following:

- preventing a hypoglycemic event(s) from occurring in said subject;
- preventing a hyperglycemic event(s) from occurring in said subject;
- reducing excessive glucose variability occurring in said subject;
- reducing postprandial glucose excursions occurring in said subject;
- reducing the risk for hypoglycemia;
- reducing the risk for hyperglycemia;
- optimizing delivery of antidiabetic drugs/compounds (including, insulin); or
- lowering glycated hemoglobin (HbA1c).

Example 29. The computer program product of example 25 (as well as subject matter of one or more of any combination of examples 26-28, in whole or in part), wherein the neural network of the neural network encoder and the neural network of the neural network decoder includes one of the following:

- artificial neural network (ANN);
- convolutional neural network (CNN); or
- recurrent neural networks (RNN).

Example 30. The computer program product of example 29, wherein the CNN is an autoencoder.

Example 31. The computer program of example 25 (as well as subject matter of one or more of any combination of examples 26-30, in whole or in part), wherein the cost function includes one or more of anyone of the following:

- maximum likelihood cost function;
- absolute deviation cost function; or mean squared error cost function.

Example 32. The computer program of example 31, wherein said mean squared error cost function is represented by the following formula:

$$\sum_{i=1}^{n} w_i^{[0,1]}(Y_i - \hat{Y}_i)^2$$

wherein:

- $Y_i$=observed result, for any i=1, 2, . . . , n
- $\hat{Y}_i$=predicted result, for any i=1, 2, . . . , n
- $w_i$=the weight of the $i^{th}$ glycemic risk profile, such that $0 \le w_i \le 1$, for any i=1, 2, . . . , n
- n=number of profiles.

whereby:

- the mean squared cost function is weighted by the corresponding glycemic risk profile or a function of the corresponding glycemic risk profile.

Example 33. The computer program product of example 32, wherein the sum of weights equals 1, wherein $$\sum_{i=1}^{n} w_i = 1.$$

Example 34. The computer program of example 25 (as well as subject matter of one or more of any combination of examples 26-33, in whole or in part), further comprising, prior to the extraction, preprocessing the received CGM data profiles.

Example 35. The computer program product of example 34, wherein the preprocessing comprises discarding a specified percentage of incomplete CGM data profiles.

Example 36. The computer program product of example 35, wherein the specified percentage of incomplete CGM data profiles includes one of the following:

- range of 0 percent and less than about 50 percent;
- range of 0 percent and less than about 40 percent;
- range of 0 percent and less than about 30 percent;
- range of 0 percent and less than about 20 percent;
- range of 0 percent and less than about 10 percent; or about 10 percent.

Example 37. A computer-implemented method for compressing continuous glucose monitor (CGM) data of a subject, comprising:

- receiving CGM data profiles of said subject;
- extracting glycemic risk profiles from the CGM data profiles;
- compressing the CGM data profiles into low-dimensional representations using a trained neural network encoder via a cost function weighted by said extracted glycemic risk profiles;
- analyzing said low-dimensional representations of CGM data profiles to obtain analyzed low-dimensional results;
- transmitting said analyzed results of said low-dimensional representations of CGM data profiles to a secondary source, wherein:

- said transmitted analyzed results of said low-dimensional representations of CGM profiles, which optionally are configured to be reconstructed to full-dimensional CGM profiles, are configured to allow:
  - a) said subject, a technician, or a clinician to take a physical action in response to receiving said transmitted analyzed results to improve the safety and/or efficacy of therapy for said subject, or
  - b) an interventional device to operationally take action in response to receiving said transmitted analyzed results to improve the safety and/or efficacy of therapy for said subject.

Example 38. The method of example 37, wherein said analyzing of said compressed CGM data profiles includes one or more of the following techniques:

- k-means clustering;
- t-distributed stochastic neighbor embedding (t-SNE);
- principal component analysis (PCA); or
- independent component analysis (ICA).

Example 39. The method of example 37 (as well as subject matter in whole or in part of example 38), wherein said interventional device includes one or more of anyone of the following:

- insulin pump device;
- decision support system;

low glucose suspend system;
connected insulin pens;
automated insulin delivery systems; or
intelligent patch or intelligent transplant.

Example 40. The method of example 37 (as well as subject matter of one or more of any combination of examples 38-39, in whole or in part), wherein said secondary source includes one or more of anyone of the following:
local memory;
remote memory; or
display or graphical user interface.

Example 41. The method of example 37 (as well as subject matter of one or more of any combination of examples 38-40, in whole or in part), wherein said improvement of the safety and/or efficacy of therapy for said subject may include one or more of the following:
preventing a hypoglycemic event(s) from occurring in said subject;
preventing a hyperglycemic event(s) from occurring in said subject;
reducing excessive glucose variability occurring in said subject;
reducing postprandial glucose excursions occurring in said subject;
reducing the risk for hypoglycemia;
reducing the risk for hyperglycemia;
optimizing delivery of antidiabetic drugs/compounds (including, insulin); or
lowering glycated hemoglobin (HbA1c).

Example 42. The method of example 37 (as well as subject matter of one or more of any combination of examples 38-41, in whole or in part), wherein the neural network of the neural network encoder and the neural network of the neural network decoder includes one of the following:
artificial neural network (ANN);
convolutional neural network (CNN); or
recurrent neural networks (RNN).

Example 43. The method of example 42, wherein the CNN is an autoencoder.

Example 44. The method of example 37 (as well as subject matter of one or more of any combination of examples 38-43, in whole or in part), wherein the cost function includes one or more of anyone of the following:
maximum likelihood cost function;
absolute deviation cost function; or
mean squared error cost function.

Example 45. The method of example 44, wherein said mean squared error cost function is represented by the following formula:

$$\sum_{i=1}^{n} w_i^{[0,1]}\left(Y_i - \hat{Y}_i\right)^2$$

wherein:
$Y_i$=observed result, for any i=1, 2, . . . , n
$\hat{Y}_i$=predicted result, for any i=1, 2, . . . , n
$w_i$=the weight of the $i^{th}$ glycemic risk profile, such that $0 \le w_i \le 1$, for any i=1, 2, . . . , n
n=number of profiles.
whereby:
the mean squared cost function is weighted by the corresponding glycemic risk profile or a function of the corresponding glycemic risk profile.

Example 46. The method of example 45, wherein the sum of weights equals 1, wherein $$\sum_{i=1}^{n} w_i = 1.$$

Example 47. A system configured for compressing continuous glucose monitor (CGM) data of a subject, comprising:
a computer processor;
a memory configured to store instructions that are executable by the computer processor, wherein said processor is configured to execute the instructions to:
receive CGM data profiles of said subject;
extract glycemic risk profiles from the CGM data profiles;
compress the CGM data profiles into low-dimensional representations using a trained neural network encoder via a cost function weighted by said extracted glycemic risk profiles;
analyze said low-dimensional representations of CGM data profiles to obtain analyzed low-dimensional results;
transmit said analyzed results of said low-dimensional representations of CGM data profiles to a secondary source,
wherein:
said transmitted analyzed results of said low-dimensional representations of CGM profiles, which optionally are configured to be reconstructed to full-dimensional CGM profiles, are configured to allow:
a) said subject, a technician, or a clinician to take a physical action in response to receiving said transmitted analyzed results to improve the safety and/or efficacy of therapy for said subject, or
b) an interventional device to operationally take action in response to receiving said transmitted analyzed results to improve the safety and/or efficacy of therapy for said subject.

Example 48. The system of example 47, wherein said analyzing of said compressed CGM data profiles includes one or more of the following techniques:
k-means clustering;
t-distributed stochastic neighbor embedding (t-SNE);
principal component analysis (PCA); or
independent component analysis (ICA).

Example 49. The system of example 47 (as well as subject matter in whole or in part of example 48), wherein said interventional device includes one or more of anyone of the following:
insulin pump device;
decision support system;
low glucose suspend system;
connected insulin pens;
automated insulin delivery systems; or
intelligent patch or intelligent transplant.

Example 50. The system of example 47 (as well as subject matter of one or more of any combination of examples 48-49, in whole or in part), wherein said secondary source includes one or more of anyone of the following:
local memory;
remote memory; or
display or graphical user interface.

Example 51. The system of example 47 (as well as subject matter of one or more of any combination of examples 48-50, in whole or in part), wherein said improvement of the safety and/or efficacy of therapy for said subject may include one or more of the following:

preventing a hypoglycemic event(s) from occurring in said subject;

preventing a hyperglycemic event(s) from occurring in said subject;

reducing excessive glucose variability occurring in said subject;

reducing postprandial glucose excursions occurring in said subject;

reducing the risk for hypoglycemia;

reducing the risk for hyperglycemia;

optimizing delivery of antidiabetic drugs/compounds (including, insulin); or lowering glycated hemoglobin (HbA1c).

Example 52. The system of example 47 (as well as subject matter of one or more of any combination of examples 48-51, in whole or in part), wherein the neural network of the neural network encoder and the neural network of the neural network decoder includes one of the following:

artificial neural network (ANN);

convolutional neural network (CNN); or recurrent neural networks (RNN).

Example 53. The system of example 52, wherein the CNN is an autoencoder.

Example 54. The method of example 47 (as well as subject matter of one or more of any combination of examples 48-53, in whole or in part), wherein the cost function includes one or more of anyone of the following:

maximum likelihood cost function;

absolute deviation cost function; or mean squared error cost function.

Example 55. The method of example 54, wherein said mean squared error cost function is represented by the following formula:

$$\sum_{i=1}^{n} w_i^{[0,1]}(Y_i - \hat{Y}_i)^2$$

wherein:

$Y_i$=observed result, for any i=1, 2, . . . , n $\hat{Y}_i$=predicted result, for any i=1, 2, . . . , n $w_i$=the weight of the $i^{th}$ glycemic risk profile, such that $0 \le w_i \le 1$, for any i=1, 2, . . . , n n=number of profiles.

whereby:

the mean squared cost function is weighted by the corresponding glycemic risk profile or a function of the corresponding glycemic risk profile.

Example 56. The method of example 55, wherein the sum of weights equals 1, wherein $$\sum_{i=1}^{n} w_i = 1.$$

Example 57. A computer program product, comprising a non-transitory computer-readable storage medium containing computer-executable instructions for compressing continuous glucose monitor (CGM) data of a subject, said instructions causing the computer to:

receive CGM data profiles of said subject;

extract glycemic risk profiles from the CGM data profiles;

compress the CGM data profiles into low-dimensional representations using a trained neural network encoder via a cost function weighted by said extracted glycemic risk profiles;

analyze said low-dimensional representations of CGM data profiles to obtain analyzed low-dimensional results;

transmit said analyzed results of said low-dimensional representations of CGM data profiles to a secondary source, wherein:

said transmitted analyzed results of said low-dimensional representations of CGM profiles, which optionally are configured to be reconstructed to full-dimensional CGM profiles, are configured to allow:

a) said subject, a technician, or a clinician to take a physical action in response to receiving said transmitted analyzed results to improve the safety and/or efficacy of therapy for said subject, or b) an interventional device to operationally take action in response to receiving said transmitted analyzed results to improve the safety and/or efficacy of therapy for said subject.

Example 58. The computer program product of example 57, wherein said analyzing of said compressed CGM data profiles includes one or more of the following techniques:

k-means clustering;

t-distributed stochastic neighbor embedding (t-SNE);

principal component analysis (PCA); or independent component analysis (ICA).

Example 59. The computer program product of example 57 (as well as subject matter in whole or in part of example 58), wherein said interventional device includes one or more of anyone of the following:

insulin pump device;

decision support system;

low glucose suspend system;

connected insulin pens;

automated insulin delivery systems; or intelligent patch or intelligent transplant.

Example 60. The computer program product of example 57 (as well as subject matter of one or more of any combination of examples 58-59, in whole or in part), wherein said secondary source includes one or more of anyone of the following:

local memory;

remote memory; or display or graphical user interface.

Example 61. The computer program product of example 57 (as well as subject matter of one or more of any combination of examples 58-60, in whole or in part), wherein said improvement of the safety and/or efficacy of therapy for said subject may include one or more of the following:

preventing a hypoglycemic event(s) from occurring in said subject;

preventing a hyperglycemic event(s) from occurring in said subject;

reducing excessive glucose variability occurring in said subject;

reducing postprandial glucose excursions occurring in said subject;

reducing the risk for hypoglycemia;

reducing the risk for hyperglycemia;

optimizing delivery of antidiabetic drugs/compounds (including, insulin); or lowering glycated hemoglobin (HbA1c).

Example 62. The computer program product of example 57 (as well as subject matter of one or more of any combination of examples 58-61, in whole or in part), wherein the neural network of the neural network encoder and the neural network of the neural network decoder includes one of the following:

artificial neural network (ANN);

convolutional neural network (CNN); or recurrent neural networks (RNN).

Example 63. The computer program product of example 62, wherein the CNN is an autoencoder.

Example 64. The computer program product of example 57 (as well as subject matter of one or more of any combination of examples 58-63, in whole or in part), wherein the cost function includes one or more of anyone of the following:

maximum likelihood cost function;

absolute deviation cost function; or mean squared error cost function.

Example 65. The computer program product of example 64, wherein said mean squared error cost function is represented by the following formula:

$$\sum_{i=1}^{n} w_i^{[0,1]}\left(Y_i - \hat{Y}_i\right)^2$$

wherein:

$Y_i$=observed result, for any i=1, 2, . . . , n $\hat{Y}_i$=predicted result, for any i=1, 2, . . . , n $w_i$=the weight of the $i^{th}$ glycemic risk profile, such that $0 \le w_i \le 1$, for any i=1, 2, . . . , n n=number of profiles.

whereby:

the mean squared cost function is weighted by the corresponding glycemic risk profile or a function of the corresponding glycemic risk profile.

Example 66. The computer program product of example 65, wherein the sum of weights equals 1, wherein $$\sum_{i=1}^{n} w_i = 1.$$

Example 67. A system configured to perform the method of any one or more of Examples 1-12 or Examples 37-46.

Example 68. A computer program product configured to perform the method of any one or more of Examples 1-12 or Examples 37-46.

Example 69. The method of using any of the elements, components, devices, computer program product and/or systems, or their sub-components, provided in any one or more of examples 13-24, 25-36, 47-56, or 57-66, in whole or in part.

Example 70. The method of manufacturing any of the elements, components, devices, computer program product and/or systems, or their sub-components, provided in any one or more of examples 13-24, 25-36, 47-56, or 57-66, in whole or in part.

REFERENCES

The devices, systems, models, apparatuses, compositions, computer program products, non-transitory computer readable medium, models, algorithms, and methods of various embodiments of the invention disclosed herein may utilize aspects (devices, systems, models, apparatuses, compositions, computer program products, non-transitory computer readable medium, models, algorithms, and methods) disclosed in the following references, applications, publications and patents and which are hereby incorporated by reference herein in their entirety, and which are not admitted to be prior art with respect to the present invention by inclusion in this section:

1. U.S. Pat. No. 10,743,809 B1, Kamousi, et al., “Systems and Methods for Seizure Prediction and Detection”, Aug. 18, 2020.
2. U.S. Pat. No. 10,699,407 B2, Isgum, et al., “Method and System for Assessing Vessel Obstruction Based on Machine Learning”, Jun. 30, 2020.
3. U.S. Pat. No. 10,565,499 B2, Bourdev, et al., “Autoencoding Image Residuals for Improving Upsampled Images”, Feb. 18, 2020.
4. U.S. Pat. No. 10,291,268 B1, Migliori, et al., “Methods and Systems for Performing Radio-Frequency Signal Noise Reduction in the Absence of Noise Models”, May 14, 2019.
5. U.S. Pat. No. 10,176,580 B2, Pauly, “Diagnostic System and Diagnostic Method”, Jan. 8, 2019.
6. U.S. Pat. No. 10,748,448 B2, Knott, et al., “Haptic Communication Using Interference of Haptic Outputs on Skin”, Aug. 18, 2020.
7. U.S. Pat. No. 10,672,504 B2, Kennedy, et al., “Algorithms for Disease Diagnostics”, Jun. 2, 2020.
8. U.S. Pat. No. 10,583,842 B1, Gunaratne, “Driver State Detection Based on Glycemic Condition”, Mar. 10, 2020.
9. U.S. Pat. No. 10,328,204 B2, Davis, et al., “System and Method for Providing Alerts Optimized for a User”, Jun. 25, 2019.
10. International Patent Appl. Publ. No. WO 2020/113128 A1, Dalal, et al., “Systems, Methods, and Devices for Biophysical Modeling and Response Prediction”, Jun. 4, 2020.
11. International Patent Appl. Publ. No. WO 2020/089656 A1, Georgiou, et al., “Predicting Physiological Parameters”, May 7, 2020
12. Makino M, et al., “Artificial Intelligence Predicts the Progression of Diabetic Kidney Disease Using Big Data Machine Learning”, Scientific Reports.
2019; 9: 11862. https://doi.org/10.1038/s41598-019-48263-5.
13. Asiri, N., Hussain M, Al Adel F, Alzaidi N, “Deep Learning Based Computer-Aided Diagnosis Systems for Diabetic Retinopathy: A Survey”, Artificial Intelligence in Medicine. 2019; 99: 101701. https://doi.org/10.1016/j.artmed.2019.07.009
14. Katsuki T, et al., “Risk Prediction of Diabetic Nephropathy via Interpretable Feature Extraction from EHR Using Convolutional Autoencoder”, Building Continents of Knowledge in Oceans of Data: The Future of Co-Created eHealth, A. Ugon, et al. (Eds.). 2018: 106-110. https://doi.org/10.3233/978-1-61499-852-5-106.
15. El Tanboly A, et al., “A Computer-Aided Diagnostic System for Detecting Diabetic Retinopathy in Optical Coherence Tomography Images”, Medical Physics. 2017; 44(3): 914-923. https://doi.org/10.1002/mp.12071.
16. Acciaroli G., et al., “Diabetes and Prediabetes Classification Using Glycemic Variability Indices from Continuous Glucose Monitoring Data”, Journal of Diabetes Science and Technology. 2018; 12 (1): 105-113. https://doi.org/10.1177/1932296817710478.

17. Longato E, et al., “Simple Linear Support Vector Machine Classifier Can Distinguish Impaired Glucose Tolerance Versus Type 2 Diabetes Using a Reduced Set of CGM-Based Glycemic Variability Indices”, Journal of Diabetes Science and Technology. 2020; 14 (2): 297-302. https://doi.org/10.1177/1932296819838856.
18. Oviedo S, et al., “Risk-Based Postprandial Hypoglycemia Forecasting Using Supervised Learning”, International Journal of Medical Informatics. 2019; 126: 1-8. https://doi.org/10.1016/j.ijmedinf.2019.03.008.
19. Kusher T, Breton M D, Sankaranarayanan S, “Multi-Hour Blood Glucose Prediction in T1D: A Patient-Specific Approach Using Shallow Neural Network Models”, Diabetes Technology & Therapeutics. 2020 [preprint]. https://doi.org/10.1089/dia.2020/0061.
20. Kovatchev B P, et al., “Symmetrization of the Blood Glucose Measurement Scale and its Applications”, Diabetes Care. 1997; 20 (11): 1655-1658. https://doi.org/10.2337/diacare.20.11.1655.
21. Kovatchev B P, et al., “Risk Analysis of Blood Glucose Data: A Quantitative Approach to Optimizing the Control of Insulin Dependent Diabetes”, Journal of Theoretical Medicine. 2001; 3 (1): 1-10. https://doi.org/10.1080/1027360008833060. https://www.hindawi.com/journals/cmmm/200/208936/
22. Kovatchev, B P, “Metrics for Glycaemic Control—from HbA1c to Continuous Glucose Monitoring”, Nature Review Endocrinology. 2017; 13 (7): 425-436. http://doi.org/10.1038/nrendo.2017.3.
23. U.S. Utility patent application Ser. No. 12/159,891, entitled “Method, System and Computer Program Product for Evaluation of Blood Glucose Variability in Diabetes from Self-Monitoring Data”, filed Jul. 2, 2008; Publication No. 2009/0171589, Jul. 2, 2009.
24. U.S. Utility patent application Ser. No. 16/588,881, entitled “Tracking the Probability for Imminent Hypoglycemia in Diabetes from Self-Monitoring Blood Glucose (SMBG) Data”, filed Sep. 30, 2019.
25. U.S. Utility patent application Ser. No. 13/394,091, entitled “Tracking the Probability for Imminent Hypoglycemia in Diabetes from Self-Monitoring Blood Glucose (SMBG) Data”, filed Mar. 2, 2012; U.S. Pat. No. 10,431,342, issued Oct. 1, 2019.
26. International Patent Application Serial No. PCT/US2010/047711, entitled “Tracking the Probability for Imminent Hypoglycemia in Diabetes from Self-Monitoring Blood Glucose (SMBG) Data”, filed Sep. 2, 2010; Publication No.
WO 2011/028925, Mar. 10, 2011.
27. U.S. Utility patent application Ser. No. 16/546,335, entitled “System Coordinator and Modular Architecture for Open-Loop and Closed-Loop Control of Diabetes”, filed Aug. 21, 2019.
28. U.S. Utility patent application Ser. No. 13/322,943, entitled “System Coordinator and Modular Architecture for Open-Loop and Closed-Loop Control of Diabetes”, filed Nov. 29, 2011; U.S. Pat. No. 10,420,489, issued Sep. 24, 2019.
29. International Patent Application Serial No. PCT/US2010/036629, entitled “System Coordinator and Modular Architecture for Open-Loop and Closed-Loop Control of Diabetes”, filed May 28, 2010; Publication No. WO 2010/138848, Dec. 2, 2010.
30. U.S. Utility patent application Ser. No. 16/451,766, entitled “TRACKING CHANGES IN AVERAGE GLYCEMIA IN DIABETICS”, filed Jun. 25, 2019; Publication No. US-2019-0318801-A1, Oct. 17, 2019.
31. U.S. Utility patent application Ser. No. 14/769,638, entitled “METHOD AND SYSTEM FOR MODEL-BASED TRACKING OF CHANGES IN AVERAGE GLYCEMIA IN DIABETES”, filed Aug. 21, 2015; U.S. Pat. No. 10,332,615, issued Jun. 25, 2019.
32. International Patent Application Serial No. PCT/US2014/017754, entitled “METHOD AND SYSTEM FOR MODEL-BASED TRACKING OF CHANGES IN AVERAGE GLYCEMIA IN DIABETES”, filed Feb. 21, 2014; Publication No. WO 2014/130841, Aug. 28, 2014.
33. U.S. Utility patent application Ser. No. 16/126,879, entitled “Method, System and Computer Program Product for Evaluation of Insulin Sensitivity, Insulin/Carbohydrate Ratio, and Insulin Correction Factors in Diabetes from Self-Monitoring Data”, filed Sep. 10, 2018; Publication No. US-2019-0019571-A1, Jan. 17, 2019.
34. U.S. Utility patent application Ser. No. 12/665,149, entitled “Method, System and Computer Program Product for Evaluation of Insulin Sensitivity, Insulin/Carbohydrate Ratio, and Insulin Correction Factors in Diabetes from Self-Monitoring Data”, filed Dec. 17, 2009; Publication No. 2010/0198520, Aug. 5, 2010.
35. International Patent Application Serial No. PCT/US2008/069416, entitled “Method, System and Computer Program Product for Evaluation of Insulin Sensitivity, Insulin/Carbohydrate Ratio, and Insulin Correction Factors in Diabetes from Self-Monitoring Data”, filed Jul. 8, 2008; Publication No. WO 2009/009528, Jan. 15, 2009.
36. U.S. Utility patent application Ser. No. 15/958,257, entitled “System, Method and Computer Readable Medium for Dynamical Tracking of the Risk for Hypoglycemia in Type 1 and Type 2 Diabetes”, filed Apr. 20, 2018; Publication No. US-2018-0366223-A1, Dec. 20, 2018.
37. International Patent Application Serial No. PCT/US2016/058234, entitled “System, Method and Computer Readable Medium for Dynamical Tracking of the Risk for Hypoglycemia in Type 1 and Type 2 Diabetes”, filed Oct. 21, 2016; Publication No. WO 2017/070553, Apr. 27, 2017.
38. U.S. Utility patent application Ser. No. 15/866,384, entitled “Method, System and Computer Program Product for Real-Time Detection of Sensitivity Decline in Analyte Sensors”, filed Jan. 9, 2018; Publication No. US-2018-0323882-A1, Nov. 8, 2018.
39. U.S. Utility patent application Ser. No. 14/266,612, entitled “Method, System and Computer Program Product for Real-Time Detection of Sensitivity Decline in Analyte Sensors”, filed Apr. 30, 2014; U.S. Pat. No. 9,882,660, issued Jan. 30, 2018.
40. U.S. Utility patent application Ser. No. 13/418,305, entitled “Method, System and Computer Program Product for Real-Time Detection of Sensitivity Decline in Analyte Sensors”, filed Mar. 12, 2012; U.S. Pat. No. 8,718,958, issued May 6, 2014.
41. International Patent Application Serial No. PCT/US2007/082744, entitled “Method, System and Computer Program Product for Real-Time Detection of Sensitivity Decline in Analyte Sensors”, filed Oct. 26, 2007; Publication No. WO/2008/052199, May 2, 2008.
42. U.S. Utility patent application Ser. No. 11/925,689, entitled “Method, System and Computer Program Product for Real-Time Detection of Sensitivity Decline in Analyte Sensors”, filed Oct. 26, 2007; U.S. Pat. No. 8,135,548, issued Mar. 13, 2012.
43. U.S. Utility patent application Ser. No. 15/580,935, entitled “INSULIN MONITORING AND DELIVERY SYSTEM AND METHOD FOR CGM BASED FAULT DETECTION AND MITIGATION VIA METABOLIC STATE TRACKING", filed Dec. 8, 2017; Publication No. US-2019-0254595-A1, Aug. 22, 2019.

44. International Patent Application Serial No. PCT/US2016/036729, entitled "INSULIN MONITORING AND DELIVERY SYSTEM AND METHOD FOR CGM BASED FAULT DETECTION AND MITIGATION VIA METABOLIC STATE TRACKING", filed Jun. 9, 2016; Publication No. WO 2016/201120, Dec. 15, 2016.
45. U.S. Utility patent application Ser. No. 15/580,915, entitled "System and Method for Tracking Changes in Average Glycemia in Diabetics", filed Dec. 8, 2017; Publication No. US-2018-0313815-A1, Nov. 1, 2018.
46. International Patent Application Serial No. PCT/US2016/036481, entitled "System and Method for Tracking Changes in Average Glycemia in Diabetics", filed Jun. 8, 2016; Publication No. WO2016200970, Dec. 15, 2016.
47. U.S. Utility patent application Ser. No. 15/669,111, entitled "METHOD, SYSTEM AND COMPUTER PROGRAM PRODUCT FOR CGM-BASED PREVENTION OF HYPOGLYCEMIA VIA HYPOGLYCEMIA RISK ASSESSMENT AND SMOOTH REDUCTION INSULIN DELIVERY", filed Aug. 4, 2017; Publication No. US-2017-0337348-A1, Nov. 23, 2017.
48. U.S. Utility patent application Ser. No. 14/015,831, entitled "CGM-Based Prevention of Hypoglycemia Via Hypoglycemia Risk Assessment and Smooth Reduction of Insulin Delivery", filed Aug. 30, 2013; U.S. Pat. No. 9,750,438, issued Sep. 5, 2017.
49. U.S. Utility patent application Ser. No. 13/203,469, entitled "CGM-Based Prevention of Hypoglycemia via Hypoglycemia Risk Assessment and Smooth Reduction Insulin Delivery", filed Aug. 25, 2011; U.S. Pat. No. 8,562,587, issued Oct. 22, 2013.
50. International Patent Application Serial No. PCT/US2010/025405, entitled "CGM-BASED PREVENTION OF HYPOGLYCEMIA VIA HYPOGLYCEMIA RISK ASSESSMENT AND SMOOTH REDUCTION INSULIN DELIVERY", filed Feb. 25, 2010; Publication No. WO 2010/099313 A1, Sep. 2, 2010.
51. U.S. Utility patent application Ser. No. 15/475,819, entitled "DISJUNCTIVE RULE MINING WITH FINITE AUTOMATON HARDWARE", filed Mar. 31, 2017; Publication No. US-2018-0285424-A1, Oct. 4, 2018.
52. U.S. Utility patent application Ser. No. 15/510,878, entitled "ACCURACY CONTINUOUS GLUCOSE MONITORING METHOD, SYSTEM, AND DEVICE", filed Mar. 13, 2017; Publication No. US-2017-0273607-A1, Sep. 28, 2017.
53. International Patent Application Serial No. PCT/US2015/045340, entitled "IMPROVED ACCURACY CONTINUOUS GLUCOSE MONITORING METHOD, SYSTEM, AND DEVICE", filed Aug. 14, 2015; Publication No. WO2016025874, Feb. 18, 2016.
54. U.S. Utility patent application Ser. No. 15/109,682, entitled "Central Data Exchange Node For System Monitoring and Control of Blood Glucose Levels in Diabetic Patients", filed Jul. 5, 2016; Publication No. US-2016-0331310-AI, Nov. 17, 2016.
55. International Patent Application Serial No. PCT/US2015/010167, entitled "Central Data Exchange Node For System Monitoring and Control of Blood Glucose Levels in Diabetic Patients", filed Jan. 5, 2015; Publication No. WO2015103543, Jul. 9, 2015.
56. U.S. Utility patent application Ser. No. 15/198,521, entitled "SEQUENTIAL PATTERN MINING WITH THE MICRON AUTOMATA PROCESSOR", filed Jun. 30, 2016; Publication No. US-2017-0293670-A1, Oct. 12, 2017.
57. U.S. Utility patent application Ser. No. 14/902,731, entitled "SIMULATION OF ENDOGENOUS AND EXOGENOUS GLUCOSE/INSULIN/GLUCAGON INTERPLAY IN TYPE 1 DIABETIC PATIENTS", filed Jan. 4, 2016; U.S. Pat. No. 10,169,544, issued Jan. 1, 2019.
58. International Patent Application Serial No. PCT/US2014/045393, entitled "SIMULATION OF ENDOGENOUS AND EXOGENOUS GLUCOSE/INSULIN/GLUCAGON INTERPLAY IN TYPE 1 DIABETIC PATIENTS", filed Jul. 3, 2014; Publication No. WO2015003124, Jan. 8, 2015.
59. U.S. Utility patent application Ser. No. 14/871,457, entitled "Association Rule Mining with the Micron Automata Processor", filed Sep. 30, 2015; U.S. Pat. No. 10,445,323, issued Oct. 15, 2019.
60. U.S. Utility patent application Ser. No. 14/799,329, entitled "ACCURACY OF CONTINUOUS GLUCOSE SENSORS", filed Jul. 14, 2015; U.S. Pat. No. 10,194,850, issued Feb. 5, 2019.
61. U.S. Utility patent application Ser. No. 12/065,257, entitled "Accuracy of Continuous Glucose Sensors", filed Feb. 28, 2008; Publication No. 2008/0314395, Dec. 25, 2008.
62. International Patent Application Serial No. PCT/US2006/033724, entitled "Method for Improvising Accuracy of Continuous Glucose Sensors and a Continuous Glucose Sensor Using the Same", filed Aug. 29, 2006; Publication No. WO07027691, Mar. 8, 2007.
63. U.S. Utility patent application Ser. No. 14/419,375, entitled "COMPUTER SIMULATION FOR TESTING AND MONITORING OF TREATMENT STRATEGIES FOR STRESS HYPERGLYCEMIA", filed Feb. 3, 2015; U.S. Pat. No. 10,438,700, issued Oct. 8, 2019.
64. International Patent Application Serial No. PCT/US2013/053664, entitled "COMPUTER SIMULATION FOR TESTING AND MONITORING OF TREATMENT STRATEGIES FOR STRESS HYPERGLYCEMIA", filed Aug. 5, 2013; Publication No. WO 2014/022864, Feb. 6, 2014.
65. U.S. Utility patent application Ser. No. 14/241,383, entitled "Method, System and Computer Readable Medium for Adaptive Advisory Control of Diabetes", filed Feb. 26, 2014; Publication No. 2015-0190098, Jul. 9, 2015.
66. International Patent Application Serial No. PCT/US2012/052422, entitled "Method, System and Computer Readable Medium for Adaptive Advisory Control of Diabetes", filed Aug. 26, 2012; Publication No. WO 2013/032965, Mar. 7, 2013.
67. U.S. Utility patent application Ser. No. 14/128,922, entitled "Unified Platform For Monitoring and Control of Blood Glucose Levels in Diabetic Patients", filed Dec. 23, 2013; Publication No. 2015/0018633, Jan. 15, 2015.
68. International Patent Application Serial No. PCT/US2012/043910, entitled "Unified Platform For Monitoring and Control of Blood Glucose Levels in Diabetic Patients", filed Jun. 23, 2012; Publication No. WO 2012/178134, Dec. 27, 2012.
69. U.S. Utility patent application Ser. No. 14/128,811, entitled "Methods and Apparatus for Modular Power Management and Protection of Critical Services in Ambulatory Medical Devices", filed Dec. 23, 2013; U.S. Pat. No. 9,430,022, issued Aug. 30, 2016.

70. International Patent Application Serial No. PCT/US2012/043883, entitled "Methods and Apparatus for Modular Power Management and Protection of Critical Services in Ambulatory Medical Devices", filed Jun. 22, 2012; Publication No. WO 2012/178113, Dec. 27, 2012.
71. U.S. Utility patent application Ser. No. 29/467,039, entitled "Alarm Clock Display of Personal Blood Glucose Level", filed Sep. 13, 2013.
72. International Patent Application Serial No. PCT/US2013/042745, entitled "INSULIN-PRAMLINTIDE COMPOSITIONS AND METHODS FOR MAKING AND USING THEM", filed May 24, 2013; Publication No. WO 2013/177565, Nov. 28, 2013.
73. U.S. Utility patent application Ser. No. 13/637,359, entitled "METHOD, SYSTEM, AND COMPUTER PROGRAM PRODUCT FOR IMPROVING THE ACCURACY OF GLUCOSE SENSORS USING INSULIN DELIVERY OBSERVATION IN DIABETES", filed Sep. 25, 2012; U.S. Pat. No. 9,398,869, issued Jul. 26, 2016.
74. International Patent Application Serial No. PCT/US2011/029793, entitled "METHOD, SYSTEM, AND COMPUTER PROGRAM PRODUCT FOR IMPROVING THE ACCURACY OF GLUCOSE SENSORS USING INSULIN DELIVERY OBSERVATION IN DIABETES", filed Mar. 24, 2011; Publication No. WO 2011/119832, Sep. 29, 2011.
75. U.S. Utility patent application Ser. No. 13/634,040, entitled "Method and System for the Safety, Analysis, and Supervision of Insulin Pump Action and Other Modes of Insulin Delivery in Diabetes", filed Sep. 11, 2012;

Publication No. 2013/0116649, May 9, 2013.

76. International Patent Application Serial No. PCT/US2011/028163, entitled "Method and System for the Safety, Analysis, and Supervision of Insulin Pump Action and Other Modes of Insulin Delivery in Diabetes", filed Mar. 11, 2011; Publication No. WO 2011/112974, Sep. 15, 2011.
77. U.S. Utility patent application Ser. No. 13/393,647, entitled "System, Method and Computer Program Product for Adjustment of Insulin Delivery (AID) in Diabetes Using Nominal Open-Loop Profiles", filed Mar. 1, 2012; Publication No. 2012/0245556, Sep. 27, 2012.
78. International Patent Application Serial No. PCT/US2010/047386, entitled "System, Method and Computer Program Product for Adjustment of Insulin Delivery (AID) in Diabetes Using Nominal Open-Loop Profiles", filed Aug. 31, 2010; Publication No. WO 2011/028731, Mar. 10, 2011.
79. U.S. Utility patent application Ser. No. 13/380,839, entitled "System, Method, and Computer Simulation Environment for In Silico Trials in Pre-Diabetes and Type 2 Diabetes", filed Dec. 25, 2011; Publication No. 2012/0130698, May 24, 2012.
80. International Patent Application Serial No. PCT/US2010/040097, entitled "System, Method, and Computer Simulation Environment for In Silico Trials in Prediabetes and Type 2 Diabetes", filed Jun. 25, 2010; Publication No. WO 2010/151834, Dec. 29, 2010.
81. U.S. Utility patent application Ser. No. 13/131,467, entitled "Method, System, and Computer Program Product for Tracking of Blood Glucose Variability in Diabetes", filed May 26, 2011; U.S. Pat. No. 9,317,657, issued Apr. 19, 2016.
82. International Patent Application Serial No. PCT/US2009/065725, entitled "Method, System, and Computer Program Product for Tracking of Blood Glucose Variability in Diabetes", filed Nov. 24, 2009; Publication No. WO 2010/062898, Jun. 3, 2010.
83. U.S. Utility patent application Ser. No. 12/975,580, entitled "Method, System, and Computer Program Product for the Evaluation of Glycemic Control in Diabetes from Self-Monitoring Data", filed Dec. 22, 2010; Publication No. 2012/0004512, Jan. 5, 2012.
84. U.S. Utility patent application Ser. No. 11/305,946, entitled "Method, System, and Computer Program Product for the Evaluation of Glycemic Control in Diabetes from Self-Monitoring Data", filed Dec. 19, 2005; U.S. Pat. No. 7,874,985, issued Jan. 25, 2011.
85. U.S. Utility patent application Ser. No. 10/240,228, entitled "Method, System, and Computer Program Product for the Evaluation of Glycemic Control in Diabetes from Self-Monitoring Data", filed Sep. 26, 2002; U.S. Pat. No. 7,025,425, issued Apr. 11, 2006.
86. International Patent Application Serial No. PCT/US2001/009884, entitled "Method, System, and Computer Program Product for the Evaluation of Glycemic Control in Diabetes", filed Mar. 29, 2001; Publication No. WO 01/72208, Oct. 4, 2001.
87. U.S. Utility patent application Ser. No. 12/664,444, entitled "Method, System and Computer Simulation Environment for Testing of Monitoring and Control Strategies in Diabetes", filed Dec. 14, 2009; Publication No. 2010/0179768, Jul. 15, 2010.
88. International Patent Application Serial No. PCT/US2008/067725, entitled "Method, System and Computer Simulation Environment for Testing of Monitoring and Control Strategies in Diabetes", filed Jun. 20, 2008; Publication No. WO 2008/157781, Dec. 24, 2008.
89. U.S. Utility patent application Ser. No. 12/516,044, entitled "Method, System, and Computer Program Product for the Detection of Physical Activity by Changes in Heart Rate, Assessment of Fast Changing Metabolic States, and Applications of Closed and Open Control Loop in Diabetes", filed May 22, 2009; U.S. Pat. No. 8,585,593, issued Nov. 19, 2013.
90. International Patent Application Serial No. PCT/US2007/085588, entitled "Method, System, and Computer Program Product for the Detection of Physical Activity by Changes in Heart Rate, Assessment of Fast Changing Metabolic States, and Applications of Closed and Open Control Loop in Diabetes", filed Nov. 27, 2007; Publication No. WO2008/067284, Jun. 5, 2008.
91. International Patent Application Serial No. PCT/US2007/000370, entitled "Method, System and Computer Program Product for Evaluation of Blood Glucose Variability in Diabetes from Self-Monitoring Data", filed Jan. 5, 2007; Publication No. WO07081853, Jul. 19, 2007.
92. U.S. Utility patent application Ser. No. 11/943,226, entitled "Systems, Methods and Computer Program Codes for Recognition of Patterns of Hyperglycemia and Hypoglycemia, Increased Glucose Variability, and Ineffective Self-Monitoring in Diabetes", filed Nov. 20, 2007; Publication No. 2008/0154513, Jun. 26, 2008.
93. U.S. Utility patent application Ser. No. 11/578,831, entitled "Method, System and Computer Program Product for Evaluating the Accuracy of Blood Glucose Monitoring Sensors/Devices", filed Oct. 18, 2006; U.S. Pat. No. 7,815,569, issued Oct. 19, 2010.
94. International Patent Application Serial No. US2005/013792, entitled "Method, System and Computer Program Product for Evaluating the Accuracy of Blood Glucose Monitoring Sensors/Devices", filed Apr. 21, 2005; Publication No. WO05106017, Nov. 10, 2005.

95. U.S. Utility patent application Ser. No. 10/592,883, entitled "Method, Apparatus, and Computer Program Product for Stochastic Psycho-physiological Assessment of Attentional Impairments", filed Sep. 15, 2006; U.S. Pat. No. 7,761,144, issued Jul. 20, 2010.
96. International Patent Application Serial No. US2005/008908, entitled "Method, Apparatus, and Computer Program Product for Stochastic Psycho-physiological Assessment of Attentional Impairments", filed Mar. 17, 2005; Publication No. 2005089431, Sep. 29, 2005.
97. U.S. Utility patent application Ser. No. 10/524,094, entitled "Method, System, And Computer Program Product For The Processing Of Self-Monitoring Blood Glucose (SMBG) Data To Enhance Diabetic Self-Management", filed Feb. 9, 2005; U.S. Pat. No. 8,538,703, issued Sep. 17, 2013.
98. International Patent Application Serial No. PCT/US2003/025053, entitled "Managing and Processing Self-Monitoring Blood Glucose", filed Aug. 8, 2003; Publication No. WO 2004/015539, Feb. 19, 2004.
99. International Patent Application Serial No. PCT/US2002/005676, entitled "METHOD AND APPARATUS FOR THE EARLY DIAGNOSIS OF SUBACUTE, POTENTIALLY CATASTROPHIC ILLNESS", filed Feb. 27, 2002)
100. U.S. Utility patent application Ser. No. 09/793,653, entitled "METHOD AND APPARATUS FOR THE EARLY DIAGNOSIS OF SUBACUTE, POTENTIALLY CATASTROPHIC ILLNESS", filed Feb. 27, 2001; Publication No. 2002/0052557, May 2, 2002.
101. U.S. Utility patent application Ser. No. 10/069,674, entitled "Method and Apparatus for Predicting the Risk of Hypoglycemia", filed Feb. 22, 2002; U.S. Pat. No. 6,923,763, issued Aug. 2, 2005.
102. International Patent Application Serial No. US00/22886, entitled "METHOD AND APPARATUS FOR PREDICTING THE RISK OF HYPOGLYCEMIA", filed Aug. 21, 2000; Publication No. WO01/13786, Mar. 1, 2001.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:

1. A computer-implemented method for compressing continuous glucose monitor (CGM) data of a subject, for use with an interventional device to improve the safety and/or efficacy of therapy for said subject, comprising:

receiving CGM data profiles of said subject;

extracting glycemic risk profiles from said CGM data profiles;

compressing said CGM data profiles into low-dimensional representations using a trained neural network encoder via a cost function weighted by said extracted glycemic risk profiles;

transmitting said low-dimensional encoded representations of CGM profiles to a secondary source;

reconstructing said transmitted low-dimensional encoded representations of CGM profiles to full-dimensional CGM profiles via a trained neural network decoder;

wherein said compressing step and said reconstructing step defines encryption and decryption, respectively;

wherein:

said transmitted reconstructed full-dimensional CGM profiles are configured to allow:

said interventional device to operationally take action on said subject in response to receiving said transmission to improve the safety and/or efficacy of therapy for said subject; and wherein said improvement of the safety and/or efficacy of therapy for said subject may include one or more of the following:

preventing a hypoglycemic event(s) from occurring in said subject;

preventing a hyperglycemic event(s) from occurring in said subject;

reducing excessive glucose variability occurring in said subject;

reducing postprandial glucose excursions occurring in said subject;

reducing the risk for hypoglycemia;

reducing the risk for hyperglycemia;

optimizing delivery of antidiabetic drugs/compounds (including, insulin); or lowering glycated hemoglobin (HbA1c).

2. The method of claim 1, wherein said interventional device includes one or more of anyone of the following:
insulin pump device;
decision support system;
low glucose suspend system;
connected insulin pens;
automated insulin delivery systems; or
intelligent patch or intelligent transplant.

3. The method of claim 1, wherein said secondary source includes one or more of anyone of the following:
local memory;
remote memory; or
display or graphical user interface.

4. The method of claim 1, wherein the neural network of the neural network encoder and the neural network of the neural network decoder includes one of the following:
artificial neural network (ANN);
convolutional neural network (CNN); or
recurrent neural networks (RNN).

5. The method of claim 4, wherein the CNN is an autoencoder.

6. The method of claim 1, wherein the cost function includes one or more of anyone of the following:
maximum likelihood cost function;
absolute deviation cost function; or
mean squared error cost function.

7. The method of claim 6, wherein said mean squared error cost function is represented by the following formula:

$$\sum_{i=1}^{n} w_i^{[0,1]}\left(Y_i - \hat{Y}_i\right)^2$$

wherein:
$Y_i$=observed result, for any i=1, 2, . . . , n
$\hat{Y}_i$=predicted result, for any i=1, 2, . . . , n
$w_i$=the weight of the $i^{th}$ glycemic risk profile, such that $0 \le w_i \le 1$, for any i=1, 2, . . . , n
n=number of profiles,
whereby:
the mean squared cost function is weighted by the corresponding glycemic risk profile or a function of the corresponding glycemic risk profile.

8. The method of claim 7, wherein the sum of weights equals 1, wherein $$\sum_{i=1}^{n} w_i = 1.$$

9. The method of claim 1, further comprising, prior to the extraction, preprocessing the received CGM data profiles.

10. The method of claim 9, wherein the preprocessing comprises discarding a specified percentage of incomplete CGM data profiles.

11. The method of claim 10, wherein the specified percentage of incomplete CGM data profiles includes one of the following:
range of 0 percent and less than about 50 percent;
range of 0 percent and less than about 40 percent;
range of 0 percent and less than about 30 percent;
range of 0 percent and less than about 20 percent;
range of 0 percent and less than about 10 percent; or
about 10 percent.

12. A system configured for compressing continuous glucose monitor (CGM) data of a subject, for use with an interventional device to improve the safety and/or efficacy of therapy for said subject, comprising:
a computer processor;
a memory configured to store instructions that are executable by the computer processor, wherein said processor is configured to execute the instructions to:
receive CGM data profiles of said subject;
extract glycemic risk profiles from said CGM data profiles;
compress said CGM data profiles into low-dimensional representations using a trained neural network encoder via a cost function weighted by said extracted corresponding glycemic risk profiles;
transmit said low-dimensional encoded representations of CGM profiles to a secondary source;
reconstruct said transmitted low-dimensional encoded representations of CGM profiles to full-dimensional CGM profiles via a trained neural network decoder;
wherein said compression and said reconstruction defines encryption and decryption, respectively;
wherein:
said transmitted reconstructed full-dimensional CGM profiles are configured to allow:
said interventional device to operationally take action on said subject in response to receiving said transmission to improve the safety and/or efficacy of therapy for said subject; and
wherein said improvement of the safety and/or efficacy of therapy for said subject may include one or more of the following:
preventing a hypoglycemic event(s) from occurring in said subject;
preventing a hyperglycemic event(s) from occurring in said subject;
reducing excessive glucose variability occurring in said subject;
reducing postprandial glucose excursions occurring in said subject;
reducing the risk for hypoglycemia;
reducing the risk for hyperglycemia;
optimizing delivery of antidiabetic drugs/compounds (including, insulin); or
lowering glycated hemoglobin (HbA1c).

13. The system of claim 12, wherein said interventional device includes one or more of anyone of the following:
insulin pump device;
decision support system;
low glucose suspend system;
connected insulin pens;
automated insulin delivery systems; or
intelligent patch or intelligent transplant.

14. The system of claim 12, wherein said secondary source includes one or more of anyone of the following:
local memory;
remote memory; or
display or graphical user interface.

15. The system of claim 12, wherein the neural network of the neural network encoder and the neural network of the neural network decoder includes one of the following:
artificial neural network (ANN);
convolutional neural network (CNN); or
recurrent neural networks (RNN).

16. The system of claim 15, wherein the CNN is an autoencoder.

17. The system of claim 12, wherein the cost function includes one or more of anyone of the following:

maximum likelihood cost function;

absolute deviation cost function; or mean squared error cost function.

18. The system of claim 17, wherein said mean squared error cost function is represented by the following formula:

$$\sum_{i=1}^{n} w_i^{[0,1]}(Y_i - \hat{Y}_i)^2$$

wherein:

$Y_i$=observed result, for any i=1, 2, . . . , n $\hat{Y}_i$=predicted result, for any i=1, 2, . . . , n $w_i$=the weight of the $i^{th}$ glycemic risk profile, such that $0 \leq w_i \leq 1$, for any i=1, 2, . . . , n n=number of profiles, whereby:

the mean squared cost function is weighted by the corresponding glycemic risk profile or a function of the corresponding glycemic risk profile.

19. The system of claim 18, wherein the sum of weights equals 1, wherein $$\sum_{i=1}^{n} w_i = 1.$$

20. The system of claim 12, further comprising, prior to the extraction, preprocessing the received CGM data profiles.

21. The system of claim 20, wherein the preprocessing comprises discarding a specified percentage of incomplete CGM data profiles.

22. The system of claim 21, wherein the specified percentage of incomplete CGM data profiles includes one of the following:

range of 0 percent and less than about 50 percent;

range of 0 percent and less than about 40 percent;

range of 0 percent and less than about 30 percent;

range of 0 percent and less than about 20 percent;

range of 0 percent and less than about 10 percent; or about 10 percent.

23. A computer program product, comprising a non-transitory computer-readable storage medium containing computer-executable instructions for compressing continuous glucose monitor (CGM) data of a subject, for use with an interventional device to improve the safety and/or efficacy of therapy for said subject, said instructions causing the computer to:

receive CGM data profiles of said subject;

extract glycemic risk profiles from said CGM data profiles;

compress said CGM data profiles into low-dimensional representations using a trained neural network encoder via a cost function weighted by said glycemic risk profiles;

transmit said low-dimensional encoded representations of CGM profiles to a secondary source;

reconstruct said transmitted low-dimensional encoded representations of CGM profiles to full-dimensional CGM profiles via a trained neural network decoder;

wherein said compression and said reconstruction defines encryption and decryption, respectively;

wherein:

said transmitted reconstructed full-dimensional CGM profiles are configured to allow:

said interventional device to operationally take action on said subject in response to receiving said transmission to improve the safety and/or efficacy of therapy for said subject; and wherein said improvement of the safety and/or efficacy of therapy for said subject may include one or more of the following:

preventing a hypoglycemic event(s) from occurring in said subject;

preventing a hyperglycemic event(s) from occurring in said subject;

reducing excessive glucose variability occurring in said subject;

reducing postprandial glucose excursions occurring in said subject;

reducing the risk for hypoglycemia;

reducing the risk for hyperglycemia;

optimizing delivery of antidiabetic drugs/compounds (including, insulin); or lowering glycated hemoglobin (HbA1c).

24. The computer program product of claim 23, wherein said interventional device includes one or more of anyone of the following:

insulin pump device;

decision support system;

low glucose suspend system;

connected insulin pens;

automated insulin delivery systems; or intelligent patch or intelligent transplant.

25. The computer program product of claim 23, wherein said secondary source includes one or more of anyone of the following:

local memory;

remote memory; or display or graphical user interface.

26. The computer program product of claim 23, wherein the neural network of the neural network encoder and the neural network of the neural network decoder includes one of the following:

artificial neural network (ANN);

convolutional neural network (CNN); or recurrent neural networks (RNN).

27. The computer program product of claim 26, wherein the CNN is an autoencoder.

28. The computer program of claim 23, wherein the cost function includes one or more of anyone of the following:

maximum likelihood cost function;

absolute deviation cost function; or mean squared error cost function.

29. The computer program of claim 28, wherein said mean squared error cost function is represented by the following formula:

$$\sum_{i=1}^{n} w_i^{[0,1]}(Y_i - \hat{Y}_i)^2$$

wherein:

$Y_i$=observed result, for any i=1, 2, . . . , n $\hat{Y}_i$=predicted result, for any i=1, 2, . . . , n $w_i$=the weight of the $i^{th}$ glycemic risk profile, such that $0 \leq w_i \leq 1$, for any i=1, 2, . . . , n n=number of profiles, whereby:

the mean squared cost function is weighted by the corresponding glycemic risk profile or a function of the corresponding glycemic risk profile.

30. The computer program product of claim 29, wherein the sum of weights equals 1, wherein $$\sum_{i=1}^{n} w_i = 1.$$

31. The computer program of claim 23, further comprising, prior to the extraction, preprocessing the received CGM data profiles.

32. The computer program product of claim 31, wherein the preprocessing comprises discarding a specified percentage of incomplete CGM data profiles.

33. The computer program product of claim 32, wherein the specified percentage of incomplete CGM data profiles includes one of the following:

range of 0 percent and less than about 50 percent;
range of 0 percent and less than about 40 percent;
range of 0 percent and less than about 30 percent;
range of 0 percent and less than about 20 percent;
range of 0 percent and less than about 10 percent; or
about 10 percent.

34. A computer-implemented method for compressing continuous glucose monitor (CGM) data of a subject, for use with an automated insulin delivery system to improve the safety and/or efficacy of therapy for said subject, comprising:

receiving CGM data profiles of said subject;

extracting glycemic risk profiles from said CGM data profiles;

compressing said CGM data profiles into low-dimensional representations using a trained neural network encoder via a cost function weighted by said extracted glycemic risk profiles;

transmitting said low-dimensional encoded representations of CGM profiles to a secondary source;

reconstructing said transmitted low-dimensional encoded representations of CGM profiles to full-dimensional CGM profiles via a trained neural network decoder;

wherein said compressing step and said reconstructing step defines encryption and decryption, respectively;

configuring said transmitted reconstructed full-dimensional CGM profiles to allow:

said automatic insulin delivery system, configured for delivering insulin to said subject, to operationally take action on said subject in response to receiving said transmission to improve the safety and/or efficacy of therapy for said subject;

wherein said improvement of the safety and/or efficacy of therapy for said subject may include one or more of the following:

predicting a hypoglycemic event for preventing said hypoglycemic event from occurring in said subject; or predicting a hyperglycemic event for preventing said hyperglycemic event from occurring in said subject;

automatically adjusting said insulin delivery by said automated insulin delivery system in response to said predicted hypoglycemic event or hyperglycemic event to prevent said hypoglycemic event or hyperglycemic event from occurring in said subject; and wherein said operational action taken includes delivering said insulin, by said automated insulin delivery system, to said subject according to said adjusted insulin delivery in response to said predicted hypoglycemic event or hyperglycemic event to prevent said hypoglycemic event or hyperglycemic event from occurring in said subject.

35. The method of claim 34, wherein said secondary source includes one or more of anyone of the following:

local memory;
remote memory; or
display or graphical user interface.

36. The method of claim 34, wherein the neural network of the neural network encoder and the neural network of the neural network decoder includes one of the following:

artificial neural network (ANN);
convolutional neural network (CNN); or
recurrent neural networks (RNN).

37. The method of claim 36, wherein the CNN is an autoencoder.

38. The method of claim 34, wherein the cost function includes one or more of anyone of the following:

maximum likelihood cost function;
absolute deviation cost function; or
mean squared error cost function.

39. The method of claim 38, wherein said mean squared error cost function is represented by the following formula:

$$\sum_{i=1}^{n} w_i^{[0,1]}(Y_i - \hat{Y}_i)^2$$

wherein:

$Y_i$=observed result, for any i=1, 2, . . . , n
$\hat{Y}$=predicted result, for any i=1, 2, . . . , n
$w_i$=the weight of the $i^{th}$ glycemic risk profile, such that $0 \le w_i \le 1$, for any i=1, 2, . . . , n
n=number of profiles, whereby:

the mean squared cost function is weighted by the corresponding glycemic risk profile or a function of the corresponding glycemic risk profile.

40. The method of claim 39, wherein the sum of weights equals 1, wherein $$\sum_{i=1}^{n} w_i = 1.$$

41. The method of claim 34, further comprising, prior to the extraction, preprocessing said received CGM data profiles.

42. The method of claim 41, wherein said preprocessing comprises discarding a specified percentage of incomplete CGM data profiles.

43. The method of claim 42, wherein the specified percentage of incomplete CGM data profiles includes one of the following:

range of 0 percent and less than about 50 percent;
range of 0 percent and less than about 40 percent;
range of 0 percent and less than about 30 percent;
range of 0 percent and less than about 20 percent;
range of 0 percent and less than about 10 percent; or
about 10 percent.

44. A system configured for compressing continuous glucose monitor (CGM) data of a subject, for use with an automated insulin delivery system to improve the safety and/or efficacy of therapy for said subject, comprising:

a computer processor;

a memory configured to store instructions that are executable by the computer processor, wherein said processor is configured to execute the instructions to:

receive CGM data profiles of said subject;

extract glycemic risk profiles from said CGM data profiles;

compress said CGM data profiles into low-dimensional representations using a trained neural network encoder via a cost function weighted by said extracted corresponding glycemic risk profiles;

transmit said low-dimensional encoded representations of CGM profiles to a secondary source;

reconstruct said transmitted low-dimensional encoded representations of CGM profiles to full-dimensional CGM profiles via a trained neural network decoder;

wherein said compression and said reconstruction defines encryption and decryption, respectively;

configure said transmitted reconstructed full-dimensional CGM profiles to allow:

said automatic insulin delivery system, configured for delivering insulin to said subject, to operationally take action on said subject in response to receiving said transmission to improve the safety and/or efficacy of therapy for said subject;

wherein said improvement of the safety and/or efficacy of therapy for said subject may include one or more of the following:

predicting a hypoglycemic event for preventing said hypoglycemic event from occurring in said subject; or predicting a hyperglycemic event for preventing said hyperglycemic event from occurring in said subject;

automatically adjust said insulin delivery by said automated insulin delivery system in response to said predicted hypoglycemic event or hyperglycemic event to prevent said hypoglycemic event or hyperglycemic event from occurring in said subject; and wherein said operational action taken includes delivery of said insulin, by said automated insulin delivery system, to said subject according to said adjusted insulin delivery in response to said predicted hypoglycemic event or hyperglycemic event to prevent said hypoglycemic event or hyperglycemic event from occurring in said subject.

45. The system of claim 44, wherein said secondary source includes one or more of anyone of the following:

local memory;

remote memory; or display or graphical user interface.

46. The system of claim 44, wherein the neural network of the neural network encoder and the neural network of the neural network decoder includes one of the following:

artificial neural network (ANN);

convolutional neural network (CNN); or recurrent neural networks (RNN).

47. The system of claim 46, wherein the CNN is an autoencoder.

48. The system of claim 44, wherein the cost function includes one or more of anyone of the following:

maximum likelihood cost function;

absolute deviation cost function; or mean squared error cost function.

49. The system of claim 48, wherein said mean squared error cost function is represented by the following formula:

$$\sum_{i=1}^{n} w_i^{[0,1]}\left(Y_i - \hat{Y}_i\right)^2$$

wherein:

$Y_i$=observed result, for any i=1, 2, . . . , n $\hat{Y}_i$=predicted result, for any i=1, 2, . . . , n $w_i$=the weight of the $i^{th}$ glycemic risk profile, such that $0 \le w_i \le 1$, for any i=1, 2, . . . , n n=number of profiles, whereby:

the mean squared cost function is weighted by the corresponding glycemic risk profile or a function of the corresponding glycemic risk profile.

50. The system of claim 49, wherein the sum of weights equals 1, wherein $$\sum_{i=1}^{n} w_i = 1.$$

51. The system of claim 44, further comprising, prior to the extraction, preprocessing the received CGM data profiles.

52. The system of claim 51, wherein the preprocessing comprises discarding a specified percentage of incomplete CGM data profiles.

53. The system of claim 52, wherein the specified percentage of incomplete CGM data profiles includes one of the following:

range of 0 percent and less than about 50 percent;

range of 0 percent and less than about 40 percent;

range of 0 percent and less than about 30 percent;

range of 0 percent and less than about 20 percent;

range of 0 percent and less than about 10 percent; or about 10 percent.

54. A computer program product, comprising a non-transitory computer-readable storage medium containing computer-executable instructions for compressing continuous glucose monitor (CGM) data of a subject, for use with an automated insulin delivery system to improve the safety and/or efficacy of therapy for said subject, said instructions causing the computer to:

receive CGM data profiles of said subject;

extract glycemic risk profiles from said CGM data profiles;

compress said CGM data profiles into low-dimensional representations using a trained neural network encoder via a cost function weighted by said glycemic risk profiles;

transmit said low-dimensional encoded representations of CGM profiles to a secondary source;

reconstruct said transmitted low-dimensional encoded representations of CGM profiles to full-dimensional CGM profiles via a trained neural network decoder;

wherein said compression and said reconstruction defines encryption and decryption, respectively;

configure said transmitted reconstructed full-dimensional CGM profiles to allow:

said automatic insulin delivery system, configured for delivering insulin to said subject, to operationally take action on said subject in response to receiving said transmission to improve the safety and/or efficacy of therapy for said subject;

wherein said improvement of the safety and/or efficacy of therapy for said subject may include one or more of the following:

predicting a hypoglycemic event for preventing said hypoglycemic event from occurring in said subject; or predicting a hyperglycemic event for preventing said hyperglycemic event from occurring in said subject;

automatically adjust said insulin delivery by said automated insulin delivery system in response to said predicted hypoglycemic event or hyperglycemic event to prevent said hypoglycemic event or hyperglycemic event from occurring in said subject; and said operational action taken includes delivery of said insulin, by said automated insulin delivery system, to said subject according to said adjusted insulin delivery in response to said predicted event to prevent said hypoglycemic event or hyperglycemic event from occurring in said subject.

55. The computer program product of claim 54, wherein said secondary source includes one or more of anyone of the following:

local memory;

remote memory; or display or graphical user interface.

56. The computer program product of claim 54, wherein the neural network of the neural network encoder and the neural network of the neural network decoder includes one of the following:

artificial neural network (ANN);

convolutional neural network (CNN); or recurrent neural networks (RNN).

57. The computer program product of claim 56, wherein the CNN is an autoencoder.

58. The computer program of claim 54, wherein the cost function includes one or more of anyone of the following:

maximum likelihood cost function;

absolute deviation cost function; or mean squared error cost function.

59. The computer program of claim 58, wherein said mean squared error cost function is represented by the following formula:

$$\sum_{i=1}^{n} w_i^{[0,1]}\left(Y_i - \hat{Y}_i\right)^2$$

wherein:

$Y_i$=observed result, for any i=1, 2, . . . , n $\hat{Y}_i$=predicted result, for any i=1, 2, . . . , n $w_i$=the weight of the $i^{th}$ glycemic risk profile, such that $0 \le w_i \le 1$, for any i=1, 2, . . . , n n=number of profiles, whereby:

the mean squared cost function is weighted by the corresponding glycemic risk profile or a function of the corresponding glycemic risk profile.

60. The computer program product of claim 59, wherein the sum of weights equals 1, wherein $$\sum_{i=1}^{n} w_i = 1.$$

61. The computer program of claim 54, further comprising, prior to the extraction, preprocessing the received CGM data profiles.

62. The computer program product of claim 61, wherein the preprocessing comprises discarding a specified percentage of incomplete CGM data profiles.

63. The computer program product of claim 62, wherein the specified percentage of incomplete CGM data profiles includes one of the following:

range of 0 percent and less than about 50 percent;

range of 0 percent and less than about 40 percent;

range of 0 percent and less than about 30 percent;

range of 0 percent and less than about 20 percent;

range of 0 percent and less than about 10 percent; or about 10 percent.

* * * * *